(12) United States Patent
Bürger et al.

(10) Patent No.: US 12,298,282 B2
(45) Date of Patent: May 13, 2025

(54) NEEDLE ASSEMBLY AND A NEEDLE RECEIVING ASSEMBLY WITH INTEGRATED ALIGNMENT, A CAPILLARY INJECTION ASSEMBLY, SYSTEM AND METHOD

(71) Applicants: Dionex Softron GmbH, Gemering (DE); Thermo Finnigan LLC, San Jose, CA (US)

(72) Inventors: Daniel Bürger, Raisting (DE); Gary Schultz, Ithaca, NY (US); Jeff Henderson, Campbell, CA (US)

(73) Assignees: Thermo Finnigan LLC, San Jose, CA (US); Dionex Softron GmbH, Germering (DE)

(*) Notice: Subject to any disclaimer, the term of this patent is extended or adjusted under 35 U.S.C. 154(b) by 991 days.

(21) Appl. No.: 17/013,155

(22) Filed: Sep. 4, 2020

(65) Prior Publication Data

US 2021/0077747 A1     Mar. 18, 2021

(30) Foreign Application Priority Data

Sep. 12, 2019   (DE) ...................... 10 2019 124 622.9

(51) Int. Cl.
  *G01N 30/22*     (2006.01)
  *A61M 5/31*      (2006.01)
  *G01N 30/18*     (2006.01)

(52) U.S. Cl.
  CPC .............. *G01N 30/22* (2013.01); *G01N 30/18* (2013.01); *A61M 2005/312* (2013.01);
  (Continued)

(58) Field of Classification Search
  CPC ......... A61M 2005/312; A61M 2205/02; B01L 2200/025; B01L 2200/0689;
  (Continued)

(56) References Cited

U.S. PATENT DOCUMENTS 9,134,335 B2   9/2015  Dehmer
9,314,794 B2   4/2016  Yamazaki
(Continued)

FOREIGN PATENT DOCUMENTS

CN    108601910 A  *  9/2018  .......... A61M 5/3202
CN    208953548 U  *  6/2019  .............. B01L 3/502
(Continued)

*Primary Examiner* — David L Singer

(57) ABSTRACT

A needle receiving assembly includes a fluid conducting element housing, a sealing element configured to receive a needle, and a fluid conducting element. The needle receiving assembly is configured to connect to a needle of a needle assembly. The fluid conducting element housing comprises an aligning component configured to contact a needle housing of the needle assembly and to increase alignment between the needle and the needle receiving assembly. The fluid conducting element housing comprises a lateral protruding portion including an inner lateral surface that laterally surrounds a cavity of the fluid conducting element housing and a central protruding portion protruding beyond a base of the fluid conducting element housing and the central protruding portion. The aligning component comprises an aligning inner surface formed by a portion of the inner lateral surface of the lateral protruding portion.

12 Claims, 28 Drawing Sheets

(52) U.S. Cl.
CPC .... *A61M 2205/02* (2013.01); *B01L 2200/025* (2013.01); *B01L 2200/0689* (2013.01); *B01L 2300/0681* (2013.01); *G01N 2030/185* (2013.01)

(58) Field of Classification Search
CPC ............. B01L 2300/0681; B01L 3/563; G01N 2030/185; G01N 30/16; G01N 30/18; G01N 35/1011; G01N 35/1095
See application file for complete search history.

(56) References Cited

U.S. PATENT DOCUMENTS

| | | | |
|---|---|---|---|
| 10,077,859 | B2 | 9/2018 | Van Pelt |
| 2004/0002684 | A1* | 1/2004 | Lopez ..................... A61M 5/14 604/411 |
| 2005/0118068 | A1* | 6/2005 | Kahl ................. B01L 3/502715 422/400 |
| 2011/0247405 | A1 | 10/2011 | Yasunaga |
| 2012/0164026 | A1* | 6/2012 | Dehmer .................. B01L 3/021 422/68.1 |
| 2014/0088514 | A1* | 3/2014 | Nzike .................... A61M 5/344 29/432 |
| 2016/0023212 | A1* | 1/2016 | Dawes .................. B01L 3/5635 422/546 |
| 2016/0209376 | A1* | 7/2016 | Yamazaki ............... B01L 3/563 |
| 2016/0325043 | A1* | 11/2016 | Fisher ..................... B01L 3/508 |
| 2018/0339105 | A1* | 11/2018 | Schader ............... A61M 5/3204 |
| 2020/0171245 | A1* | 6/2020 | Zucchelli ............ A61M 5/3134 |

FOREIGN PATENT DOCUMENTS

| | | | |
|---|---|---|---|
| DE | 10 2011 075 146 A1 | 11/2012 | |
| DE | 10 2014 109 538 A1 | 1/2016 | |
| WO | WO-2008063070 A1 * | 5/2008 | .......... B01J 19/0046 |

* cited by examiner

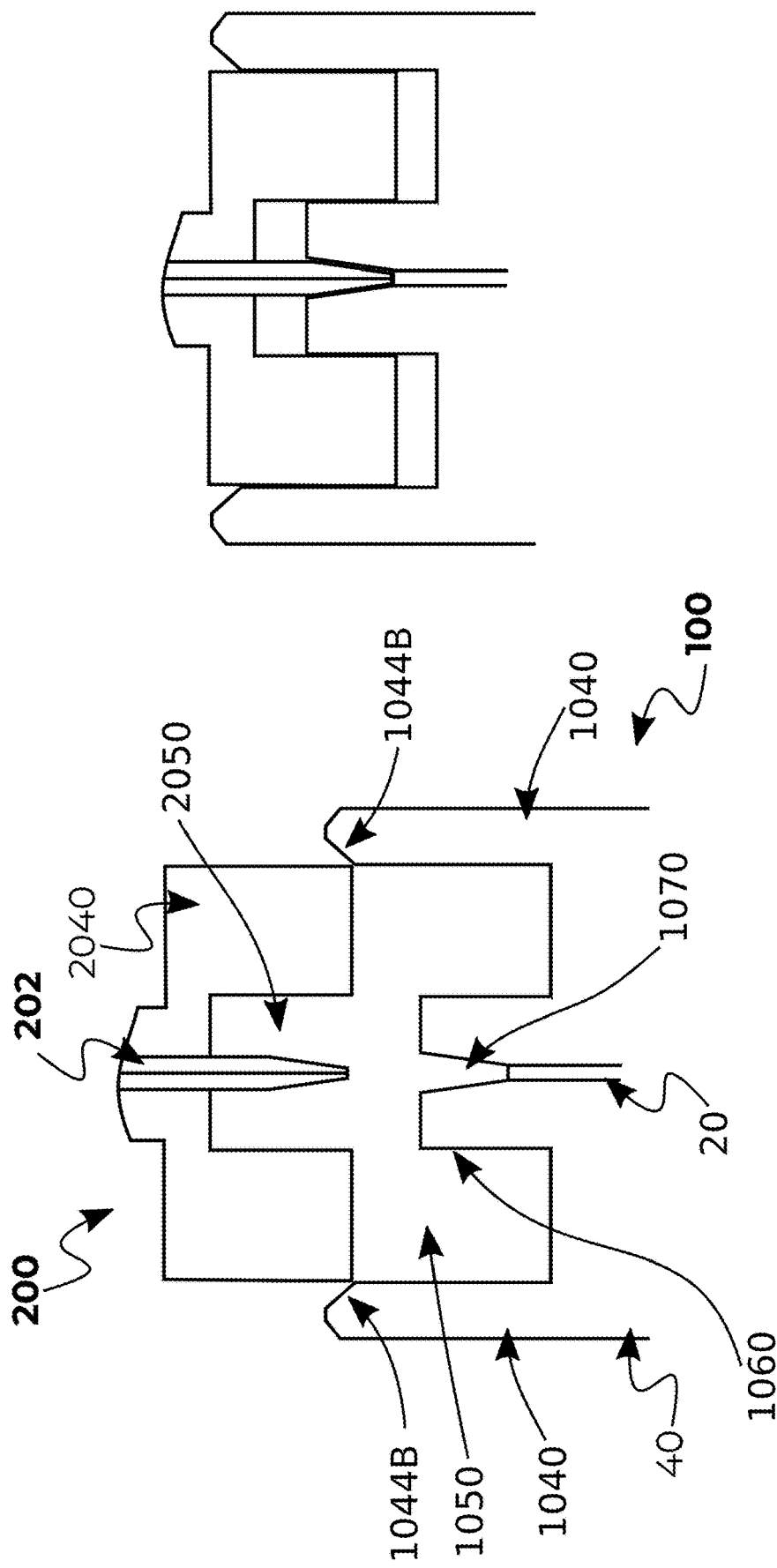

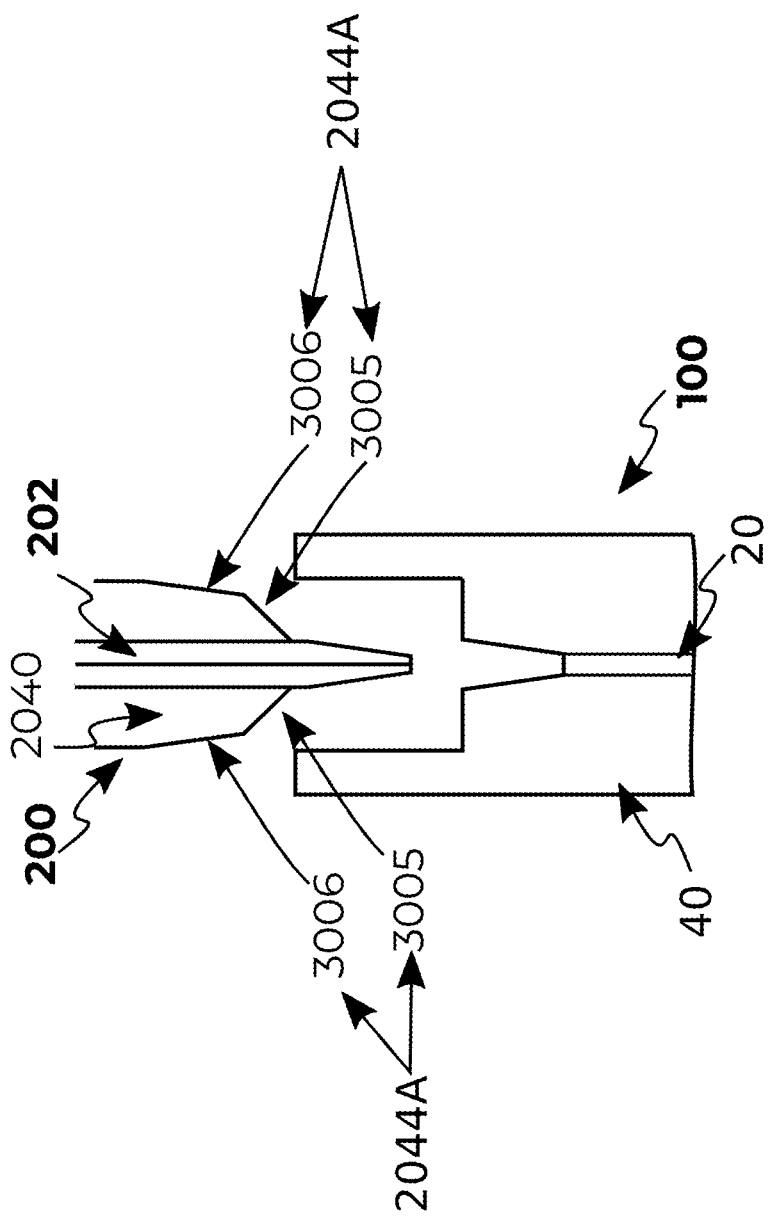

NEEDLE ASSEMBLY AND A NEEDLE RECEIVING ASSEMBLY WITH INTEGRATED ALIGNMENT, A CAPILLARY INJECTION ASSEMBLY, SYSTEM AND METHOD

CROSS-REFERENCE TO RELATED APPLICATIONS

This application claims the priority benefit under 35 U.S.C. § 119 to German Patent Application No. 10 2019 124 622.9, filed on Sep. 12, 2019, which application is hereby incorporated herein by references in its entirety.

FIELD OF THE INVENTION

The present invention generally relates to the injection of a sample into a system. The invention lies in the field of chromatography, such as liquid chromatography (LC) and particularly in the field of samplers for High-Performance Liquid Chromatography (HPLC). HPLC is a method of separating samples into their constituent parts. The sample can be separated for subsequent use, or the portions of the sample can be detected and quantified. More particularly, the present invention relates to a liquid chromatography system, a method performed in such a system and corresponding use of the system.

BACKGROUND

LC systems are based on chromatographic separation, where a sample may be separated into a characteristic separation pattern by pumping the sample together with an elution solvent, i.e., the mobile phase, through a chromatographic column which contains a solid, i.e., a stationary phase. Analytes in the mobile phase interact with the stationary phase and depending on the intensity of interaction between the mobile phase and the stationary phase, the analytes are retained to a characteristic degree. As a result, components of the sample exit the separation column after different times depending on the strength of interaction, which time may be referred to as a retention time (RT). In simple words, components of a sample may be separated by means of a separation column whose content interacts differently with the different components of the sample. This determines the time that the components are retained in the separation column, which means that the RT is a characteristic for each component of a sample under given chromatographic conditions.

In HPLC, the separation of compounds can be influenced by adjusting the composition of the mobile phase over time, and by adjusting the properties of the stationary phase. For instance, the separation accuracy of the column depends on the grain size of the packing material. Even though smaller grain sizes may achieve a better separation, it may result in a large resistance within a fluidic system, which may result in a decreased throughput. To counteract this, the trend in HPLC analyses is towards ever higher pressures. As such, all components of the HPLC system must withstand these higher pressures. In HPLC, a sampler may have the task of managing samples and introducing a defined quantity of a sample into the fluidics of a column at a defined point in time. In some instances, the sampler may use a needle which may be adapted to pick the sample up and then move it into a needle seat, which may subsequently be sealed at high pressures at a needle seat. Thereafter, a valve may switch the sample via the needle and the needle seat into the fluid path to the column.

In the state of the art, a conical needle may be sealed by locating it into a conical needle seat. The angle of the needle is usually more acute than the angle of the needle seat seal. On the opposite side a capillary may be sealed by means of a cutting ring.

US2011247405 refers a sample injection port for injecting a sample into a chromatograph or other devices which is composed of a body made of an inelastic material, a first seal member made of an elastic material and attached to one end of the body, and a second seal member made of an elastic material and attached to the other end of the body. A first through hole formed in the first seal member, a second through hole formed in the second seal member and a third through hole formed in the body part are coaxially connected to form an introduction hole for sample injection. FIG. 15 is based on FIG. 3 of this prior art document.

As can be seen in FIG. 15, a needle P9 can be received in a seal member P14, which may be made of a PEEK resin. Further, there is depicted a housing P11, and a cap P16. If the seal member P14 is not completely chambered, there will be air gaps P20 into which material can be extruded. As soon as the sealing material begins to flow away, the seal member P14 becomes leaky as there is no back pressure on the seal member P14. In addition, the sealing member P14 presses axially on the tube P12, so that the fluid-carrying bore can be very easily blocked. The opening angle of the needle seat is very large (see P21), so that material can also flow here. Furthermore, in US2011247405, the needle P9 and the seal member P14 may be misaligned in the process of connecting the needle P9 and the seal member P14, which may lead to damages, e.g., on the needle.

DE102011075146 refers to a seat device for releasably receiving a sample injection needle of a sample injection device for injecting a fluid sample into a fluidic path, wherein the seat device comprises a housing and a capillary arranged at least partially in the housing, the end portion of which capillary forms a seat for the sample injection needle and which can be brought into fluid communication with the fluidic path. FIG. 16 corresponds to FIG. 3 of this prior art document.

Here a PEEK hose 308 is provided with a metal sheath 310 to achieve a higher-pressure stability. Then the end has to be formed into a needle seat. However, the wall of the pipe could buckle as well as lead to sealing problems when forming the needle seat geometry due to inaccuracies. The sealing material is also not completely chambered. Generally, a thin PEEK valve seat is thus provided which is supported on its outer surface by a supporting sleeve 318. Moreover, the needle is centered in the seat device 300 by means of a centering sleeve 320. More particularly, the needle can contact the centering sleeve 320 (if misaligned) and can be centered by the centering sleeve 320. That is, the centering sleeve 320 can center the needle only upon contact with the needle. However, during contact the needle may sting the centering sleeve 320 which may cause damages and blockages to the needle. Additionally, during contact with the centering sleeve, the needle may produce abrasion which can block the fluidic paths, particularly in a Nano HPLC system. Further still, when the needle receives the sample, part of the outer surface of the needle may be covered by the sample which can then be deposited on the centering sleeve 320, particularly if the needle stings on the centering sleeve 320. As such, future samples can be contaminated by previous samples which can lead to inferior analysis.

Thus, the state of the art seals a conical needle into a conical needle seat. The needle is either moved freely without a direction to the needle seat or by means of centering in the direction of the needle seat.

While the prior art solutions may be satisfactory to some extent, they still have certain drawbacks and limitations. The needle seat of US2011247405 may not allow for a stable, high pressure tight operation with a long service life, and it may cause blockage of downstream sections. In addition, components may be misaligned during the process of connecting the components to one another. The needle seat of DE102011075146 may be prone to buckling, and may generally be delicate, also impacting its service life. In addition, DE102011075146 provides needle centering means that require contact of the needle with other elements. This may lead to blockages, needle damages and contamination of new samples by previous samples.

That is, if the needle is not properly centered, the needle may sting next to the needle seat, causing the needle seat to wear more or even damage the needle. Moreover, the needle may produce abrasion and can lead to blockage, especially with Nano H PLC. If the centering of the needle takes place via a centering sleeve, the sample may be on the outer edge of the needle when the sample is drawn by the needle; this can then be deposited on the centering sleeve. The next time samples are injected, the sample previously deposited on the centering sleeve could mix with the new sample and falsify the analysis.

SUMMARY

In light of the above, it is an object of the present invention to overcome or at least alleviate at least some of the shortcomings and disadvantages of the prior art. That is, it is an object of the present invention to provide an improved assembly that is adapted to receive a liquid from a needle, a corresponding sampler, system, method and use. In particular, it may be an object of the present invention to provide an assembly for receiving a liquid from a needle that is improved as regards its pressure tightness, has a relatively small dead volume, and a long service life. Furthermore, it may also be an object of the present invention to provide assemblies which are less prone to blockage, damages and/or contamination by previous runs.

It can also be an object of the present invention to provide a high-pressure resistant needle seat with a low dead volume. This should have a long service life and therefore little wear.

At least some of these objects are met by the present invention.

In a first aspect, the present invention relates to a needle assembly for facilitating connecting a needle and a needle receiving assembly. The needle assembly can comprise a needle and a needle housing. The needle defines an axial direction and a radial direction perpendicular to the axial direction. Moreover, along the axial direction a tip of the needle is more proximal than the rest of the needle. The needle housing comprises a cavity, which is occupied in part by the needle. In addition, the needle housing comprises at least one aligning component configured to increase alignment in the radial direction between the needle and the needle receiving assembly upon contact between the at least one aligning component and the needle receiving assembly.

Thus, the present invention provides a needle assembly with at least one aligning component for facilitating the alignment of the needle with the needle receiving assembly. This has multiple advantages over prior art solutions, e.g., not providing aligning means at all or providing a centering sleeve which can align the needle upon contact with the needle.

As an initial matter, the present invention facilitates bringing the needle into proper alignment with a needle receiving assembly. This can prevent or at least alleviate blockages of the flow path between the needle and the needle receiving assembly. Moreover, the present invention can particularly be advantageous in applications where precise alignment of the needle with the needle receiving assembly is desirable. Typically, a precise alignment of the needle may advantageous if the needle comprises a small diameter. For example, in some application, such as HPLC, the needle may comprise a very small inner diameter, such as, 50 μm. Thus, a deviation of 50 μm or more from the aligned position can completely block the needle, e.g. the needle would face a wall of the needle receiving assembly instead of an opening configured to receive the needle. Typically, in the above example, the deviation should be at most 20 μm, or even better at most 10 μm, best of all 0 μm.

Such precise alignments are generally challenging to be achieved. Alternatively, they may require dedicated and complex actuators for automatically guiding the needle into proper alignment. The present invention can alleviate these issues by providing a needle housing with at least one aligning component. Thus, even if the needle and the needle receiving assembly are misaligned, the at least one aligning component can bring them into proper alignment during the connection between the two. Hence, the needle assembly can make the process of connecting the needle with the needle receiving assembly more ergonomic and manageable for a human user. In addition, the need of precise and complex actuators (e.g. in application wherein the needle is handled automatically) can be alleviated.

Moreover, in many applications, the dead volume following the needle when connected to the needle receiving assembly should be as small as possible. This is particularly advantageous when a high-pressure fluid is expected to flow through the needle, such as, in HPLC systems. As such, to achieve a small dead volume, the needle may also comprise a very small diameter. The smaller the needle and its diameter, the more precise the alignment of the needle with the needle receiving assembly should be. Thus, by facilitated the alignment of the needle, the present invention can allow for the use of small needles, which in turn can facilitate having a small dead volume after the needle. Again, this is particularly advantageous for high-pressure systems, such as, H PLC.

Furthermore, alignment of the needle with the needle receiving assembly is increased upon contact between the at least one aligning component and the needle receiving assembly. Thus, there is no need for the needle to contact other components for aligning purposes. Even more, by providing a needle housing with at least one aligning component, the present invention decreases the likelihood of the needle bumping, stinging, colliding, or pricking on the needle receiving assembly. This can be advantageous because it can avoid damages or abrasion of the needle and/or of the needle receiving assembly which can lead to blockages of the fluid path if not prevented. As such, the present invention may increase the durability of the needle and/or needle receiving assembly.

Further still, aligning the needle using the at least one aligning component of the needle housing, instead of using the needle itself, can be advantageous as it can reduce contamination. This is particularly the case if the needle is used to draw up a sample. In such cases, the tip of the needle is immersed in the sample. As such, a part of the sample can remain on the outer walls of the needle, even after the sample is drawn. If the needle contacts other components, the part of the sample remaining on the walls of the needle can be deposited on the contacted components. This can cause contamination of future samples. In many applications, this is a non-desired effect. The present invention avoids this by instead providing a needle housing with at least one aligning component which decreases the likelihood of the needle bumping, stinging, colliding, or pricking on other components, such as, the needle receiving assembly.

In some embodiments, the needle housing can comprise an outer lateral surface. In such embodiments, the aligning component of the needle housing can comprise an aligning outer surface that can be formed by at least a portion of the outer lateral surface of the needle housing. In other words, an aligning component (i.e. the aligning outer surface) can be provided on the outer surface of the needle housing. This can be advantageous if a portion of the needle housing can be received by the needle receiving assembly, i.e., if the needle receiving assembly can surround the needle housing, when connected. Thus, during the connection, the needle receiving assembly can contact the outer surface of the needle housing and more particularly the aligning outer surface, which can increase alignment in the radial direction between the needle and the needle receiving assembly.

In some embodiments, a diameter of cross sections of the aligning outer surface can decrease continuously along the axial direction such that for any two cross sections of the aligning outer surface wherein a first cross section is more proximal than a second cross section, the diameter of the first cross section can be smaller than the diameter of the second cross section. Each cross section of the aligning outer surface is an intersection between the aligning outer surface and a plane perpendicular to the axial direction. In other words, the diameter of the aligning outer surface can be expressed as a function of the position along the axial direction, which function is a strictly decreasing function along the downstream direction. This (i.e. the continuous decrease of the diameter) can facilitate a sliding motion between the needle housing and the needle receiving assembly during the connection. In other words, there can be no section of the aligning outer surface which can resist the needle to be received in the needle receiving assembly. For example, there can be no surface of the aligning outer surface being perpendicular to the axial direction. This can be achieved by the diameter of cross sections of the aligning outer surface decreasing continuously.

The aligning outer surface can comprise a most distal cross-section, which is more distal than the rest of the aligning outer surface, and a most proximal cross section, which is more proximal than the rest of the aligning outer surface. In some embodiments, the diameter of the most distal cross-section of the aligning outer surface can be larger than the diameter of the rest of the cross-sections of the aligning outer surface. Thus, the diameter of the aligning outer surface can continuously increase from the most proximal cross section to the most distal cross section. Hence, the needle housing can comprise more freedom of movement along the radial direction when the most proximal cross section is received in the needle receiving assembly. As the needle housing is received in the needle receiving assembly, its freedom of movement along the radial direction can be decreased. At the same time, alignment in the radial direction can be increased. When the most distal section is received, the freedom of movement can be at minimum, while alignment in the radial direction can be at maximum. For example, if the diameter of the most distal section of the needle housing matches an inner diameter of the needle receiving assembly (wherein the needle housing is received), the freedom of movement along the radial direction of the needle housing can be reduced almost completely.

In some embodiments, the diameter of the most proximal cross-section of the aligning outer surface can be at least 30%, preferably at least 40%, more preferably at least 60% and at most 90%, such as 80% to 85% of the diameter of the most distal cross-section of the aligning outer surface. Typically, the smaller the diameter of the most proximal cross-section relative to the most distal cross-section, the larger the deviation in the radial direction that can be corrected by the aligning outer surface. On the other hand, the larger the diameter of the most proximal cross-section relative to the most distal cross-section, the smaller the force parallel to the axial direction opposing the insertion of the needle housing in the needle receiving assembly can be. In other words, the diameter of the most proximal cross-section and the most distal cross-section can determine the slope of the aligning outer surface. Moreover, determining the slope of the aligning outer surface may involve a trade-off between tolerable deviation in the radial direction and ease of slide between the needle housing and needle receiving assembly. The above dimensions generally provide a good trade-off between the two.

In some embodiments, the diameter of the distal cross-section of the aligning outer surface can correspond to the largest extension of the needle housing along the radial direction.

The diameter of the distal cross-section of the aligning outer surface can be in the range of 2 mm to 50 mm, preferably 4 mm to 20 mm, more preferably 5 mm to 10 mm, such as 7.5 mm. Typically, a large diameter of the distal cross-section of the aligning outer surface can allow for larger deviations of the needle in the radial direction to be corrected. However, this may lead to a bulky needle housing. Thus, there can be a tradeoff between the size of the needle housing and the tolerable misalignment that can be corrected.

In some embodiments, the diameter of the cross sections of the aligning outer surface can decrease linearly with at least one rate.

In some embodiments, the diameter of the cross sections of the aligning outer surface can decrease linearly with a constant rate. That is, the aligning outer surface can resemble the surface of a conical frustum. This can provide a particularly simple aligning component.

Alternatively, the diameter of the cross sections of the aligning outer surface can decrease linearly with two distinct rates. That is the aligning outer surface can comprise the shape of two joined conical frustums, such that, a top of a distal conical frustum corresponds to a base of a proximal conical frustum and wherein the proximal conical frustum is more proximal than the distal conical frustum. This can allow alignment of the needle with the needle receiving assembly at different rates, while the needle is received in the needle receiving assembly.

Thus, in some embodiments, the aligning outer surface can comprise a proximal aligning outer surface and a distal aligning outer surface, wherein the proximal aligning outer surface is more proximal than the distal aligning outer surface. The diameter of the cross sections of the proximal aligning outer surface can decrease with a different rate than the diameter of the cross sections of the distal aligning outer surface.

In some embodiments, the diameter of the cross sections of the proximal aligning outer surface can decrease with a higher rate than the diameter of the cross sections of the distal aligning outer surface. That is, the taper angle of the proximal aligning outer surface can be larger than the taper angle of the distal aligning outer surface. Thus, the aligning outer surface can be a convex surface, instead of a concave one, which can be particularly advantageous for reducing the forces opposing the reception of the needle in the needle receiving assembly.

Moreover, the diameter of the cross-sections of the proximal aligning outer surface may not exceed the diameter of the cross-sections of the distal aligning outer surface.

In some embodiments, the aligning outer surface can amount to at least 5% and at most 60%, such as, 30% of the extension along the axial direction of the needle housing. For example, the aligning outer surface can comprise a length along the axial direction of at least 0.5 mm and at most 20 mm, preferably at most 10 mm, more preferably at most 5 mm, such as 1 mm.

It will be understood, that aligning outer surface can also comprise at least one curved section along the axial direction, preferably forming a convex surface along the axial direction. In some embodiments, the curved section can be provided more proximal than the rest of the aligning outer surface. Alternatively or additionally, the curved section can be provided on the proximal aligning outer surface and/or on the distal aligning outer surface. Alternatively or additionally, the curved section can be provided on the transition between the proximal aligning outer surface and the distal aligning outer surface. In some embodiments, the entire aligning outer surface can be curved.

The needle housing can comprise a distal portion wherein the distal portion can be more distal than the rest of the needle housing.

In some embodiments, a plurality of cross sections of the distal portion can comprise the same outer diameter, wherein a cross section of the distal portion is an intersection between the distal portion and a plane perpendicular to the axial direction. That is, in some embodiments, the distal cross section of a portion of the distal cross section can comprise a cylindrical shape.

The distal portion can comprise a width along the radial direction that can correspond to the largest extension along the radial direction of the needle housing.

For example, the distal portion can comprise a width along the radial direction in the range of 2 mm to 50 mm, preferably 4 mm to 20 mm, more preferably 5 mm to 10 mm, such as 7.5 mm.

Moreover, the distal portion can amount to at least 40% and at most 80%, such as, 65% of the extension along the axial direction of the needle housing. For example, the distal portion can comprise a length along the axial direction in the range of 0.5 mm to 40 mm, preferably 1 mm to 10 mm, more preferably 2 mm to 5 mm, such as 2.3 mm.

In some embodiments, the aligning outer surface can be provided more proximal than the distal portion. For example, the aligning outer surface may directly follow the distal portion.

The diameters of the cross sections of the aligning outer surface do not exceed the width along the radial direction of the distal portion, wherein each cross section of the aligning outer surface is an intersection between the aligning outer surface and a plane perpendicular to the axial direction. That is, the aligning outer surface may not extend more than the distal portion in the radial direction. In some embodiments, the outer diameter of the distal portion may match the maximum diameter of the aligning outer surface.

The needle housing can further comprise a proximal portion wherein the proximal portion can be more proximal than the rest of the needle housing.

The proximal portion can amount to at least 1% and at most 20%, preferably 5% to 8% of the extension along the axial direction of the needle housing.

In some embodiments, wherein the needle housing comprises the distal portion, aligning outer surface and the proximal portion, as discussed above, the aligning outer surface can be between the distal portion and the proximal portion. For example, the aligning outer surface may directly follow the distal portion and the proximal portion may directly follow the proximal portion.

The extension along the radial direction of the proximal portion may not exceed the extension along the radial direction of the aligning outer surface. This can allow the aligning outer surface to contact the needle receiving assembly.

In some embodiments, the aligning outer surface can extend along the axial direction up to and including the proximal portion.

The proximal portion can protrude proximally beyond the tip of the needle.

That is, the needle can be mounted in a needle holder which can centers itself over the outer contour in the needle seat holder (i.e. needle receiving assembly). For example, a metallic needle can be welded to a metallic needle holder. A needle made of quartz glass (fused silica) can be pressed into a holder made of PEEK. The needle "stands back" behind the holder (i.e. the needle holder protrudes proximally beyond the needle), so that the needle tip and the user of the needle can be protected. As such, the needle housing can serve as needle protection, so that the needle cannot bump or be demolished when the needle assembly is handled and/or when the needle is changed. At the same time, the needle housing comprising the proximal portion that protrudes proximally beyond the tip of the needle, can protect the user or handler of the needle assembly from being accidentally pricked by the needle.

As such, the present invention can provide needle alignment, needle protection and user protection in one component. That is, on the one hand the needle housing may comprise at least one aligning component which can be configured to increase alignment between the needle and the needle receiving assembly. Thus, the needle can be guided and protected from shocks (i.e. collisions) as the at least one aligning component can be configured to avoid contact of the needle with other components. On the other hand, the needle housing may extend proximally beyond the needle tip, which can provide protection to the needle and to a handler or user of the needle.

All in all, aspects of the present invention may comprise the following advantages: Needle can be guided through construction. The needle tip can be protected which can lead to longer durability. Additionally, this can reduce the risk of injury when changing the needle. Moreover, a simple needle assembly is provided which can lead to fewer assembly errors.

It should be understood that this feature, i.e., the proximal portion of the needle housing protruding proximally beyond the tip of the needle, may also be employed independently from the aligning component. That is, there are also embodiments of the present invention, wherein the needle housing does not necessarily comprise at least one aligning component as discussed above. Instead, the proximal protrusion beyond the tip of the needle may also be employed independently from the aligning component.

In other words, in a second aspect the present invention may relate to a needle assembly for facilitating connecting a needle and a needle receiving assembly, wherein the needle assembly comprises the needle, wherein the needle defines an axial direction and wherein a tip of the needle is more proximal than the rest of the needle and a radial direction perpendicular to the axial direction. In addition, the needle assembly comprises a needle housing comprising a cavity and wherein the cavity is occupied in part by the needle. The needle housing further comprises a proximal portion wherein the proximal portion is more proximal than the rest of the needle housing. The proximal portion protrudes proximally beyond the tip of the needle.

Thus, whenever such a feature, i.e., the proximal portion of the needle housing protruding proximally beyond the tip of the needle, is discussed, it should be understood that such discussions relate to the needle assembly according to the first aspect comprising said feature in addition to the aligning component and to the needle assembly according to the second aspect comprising said feature independently from the aligning component.

In some embodiments, the proximal portion protruding proximally beyond the tip of the needle is in the range of 0.1 mm to 2 mm, preferably 0.2 mm to 1 mm, such as 0.25 mm. Such dimensions can provide sufficient protection, while still limiting the bulkiness of the needle housing.

In some embodiments the needle housing can comprise an in an inner surface that laterally encloses the cavity of the needle housing.

Furthermore, the aligning component can comprise an aligning inner surface that can be formed by at least a portion of the inner surface that laterally encloses the cavity.

That is, in some embodiments, the needle housing can be configured to receive a portion of the needle receiving assembly (e.g. a central protruding portion of the needle receiving assembly). More particularly, a portion of the cavity of the needle housing can be occupied by a portion of the needle receiving assembly that can be received therein. Thus, during the connection the needle receiving assembly can contact the needle housing and more particularly the inner surface that laterally surrounds the cavity of the needle housing. As such, to facilitate the connection an aligning inner surface can be provided on the inner surface that laterally encloses the cavity. That is, the inner surface that laterally encloses the cavity of the inner housing can be configured to form an aligning inner surface.

A diameter of the cross sections of the aligning inner surface can increases continuously along the axial direction. More particularly, for any two cross sections of the aligning inner surface, wherein a first cross section is more proximal than a second cross section, the diameter of the first cross section can be larger than the diameter of the second cross section. It will be understood that each cross section of the aligning inner surface is an intersection between the aligning inner surface and a plane perpendicular to the axial direction. In other words, the diameter of the aligning inner surface can be expressed as a function of the position along the axial direction, which function is a strictly increasing function along the downstream direction. This (i.e. the continuous increase of the diameter) can facilitate a sliding motion between the needle housing and the needle receiving assembly during the connection. In other words, there can be no section of the aligning inner surface which can resist the needle to be received in the needle receiving assembly. For example, there can be no surface of the aligning inner surface being perpendicular to the axial direction. This can be achieved by a continuous increase of the diameter of cross sections of the aligning inner surface.

In some embodiments, the diameter of the cross sections of the aligning inner surface can increases linearly with at least one rate.

In some embodiments, the diameter of the cross sections of the aligning inner surface can increases linearly with a constant rate. That is, the aligning inner surface can comprise a conical frustum shape. This can provide a particularly simple aligning component.

Alternatively, the diameter of the cross sections of the aligning inner surface can increase linearly with two distinct rates. That is, the aligning inner surface can comprise the shape of two joined conical frustums, such that, a base of the distal conical frustum can correspond to a top of the proximal conical frustum. This can allow alignment of the needle with the needle receiving assembly at different rates, while the needle is received in the needle receiving assembly.

The aligning inner surface can comprise a proximal aligning inner surface and a distal aligning inner surface, wherein the proximal aligning inner surface is more proximal than the distal aligning inner surface. Moreover, the diameter of the cross sections of the proximal aligning inner surface can increase with a different rate than the diameter of the cross sections of the distal aligning inner surface.

In some embodiments, the diameter of the cross sections of the proximal aligning inner surface can increase with a higher rate than the diameter of the cross sections of the distal aligning inner surface. That is, the taper angle of the proximal aligning inner surface can be larger than the taper angle of the distal aligning inner surface. Thus, the aligning inner surface can be a convex surface, instead of a concave one, which can be particularly advantageous for reducing the forces opposing the reception of the needle in the needle receiving assembly.

Moreover, in some embodiments, the diameter of the cross-sections of the distal aligning inner surface may not exceed the diameter of the cross-sections of the proximal aligning inner surface.

In some embodiments, the aligning inner surface can be positioned in the proximal portion of the needle housing. In such embodiments, the aligning inner surface may extend along at least 30%, preferably at least 60%, more preferably at least 80% of the length along the axial direction of the proximal portion.

It will be understood, that aligning inner surface can also comprise at least one curved section along the axial direction, preferably forming a convex surface along the axial direction. In some embodiments, the curved section can be provided more proximal than the rest of the aligning inner surface. Alternatively or additionally, the curved section can be provided on the proximal aligning inner surface and/or on the distal aligning inner surface. Alternatively or additionally, the curved section can be provided on the transition between the proximal aligning inner surface and the distal aligning inner surface. In some embodiments, the entire aligning inner surface can be curved.

The needle can comprise a metallic, quartz glass and/or fused silica material.

The needle housing can comprise a metallic or polymetric material, such as, poly-ether-ether-ketone (PEEK), polyether-ketone (PEK), poly-ether-ether-ether-ketone (PEEEK) and a polyphenylene sulfide (PPS).

The needle can be unreleasably mounted on the needle housing. This can be advantageous as the attachment between the needle and the needle housing can be maintained even under high pressures.

As discussed, the needle and the needle housing may comprise a metallic material. In such embodiments, the needle can be welded to the needle housing. This can provide a simple and secure (preferably, even under high pressure) attachment between the needle and the needle housing.

Alternatively or additionally, the needle can be pressed into the needle housing, thus rendering an unreleasable connection between the two.

It will be understood that the above are only some exemplary means of mounting the needle housing into the needle (or vice versa). The person skilled in the art will appreciate that other connection means can be used as well.

The needle housing may comprise an extension along the radial direction between 2 times to 100 times, preferably 5 times to 20 times, more preferably 8 times to 12 times the outer diameter of the needle.

For example, the needle housing can comprise an extension along the radial direction in the range of 2 mm to 50 mm, preferably 4 mm to 20 mm, more preferably 5 mm to 10 mm, such as 7.5 mm.

Moreover, the needle housing can comprise an extension along the axial direction in the range of 1 mm to 50 mm, preferably 2 mm to 10 mm.

It will be understood that the above are only some exemplary dimensions of the needle housing. The person skilled in the art will appreciate that the needle housing may comprise other dimensions as well. Generally, dimensions of the needle housing may depend on (and can thus be respectively adapted to) the dimensions of the needle and/or needle receiving assembly and/or size limitations that can be imposed by the system wherein the needle assembly can be used. The same holds also for the other dimensions provided throughout the description of the present invention.

The outer diameter of the needle can be in the range of 0.1 mm to 2 mm, preferably 0.3 mm to 1.8 mm, more preferably between 0.5 mm to 1.6 mm.

The inner diameter of the needle can be in the range of 5 µm to 500 µm, preferably 30 µm to 400 µm, more preferably 50 µm to 300 µm. That is, the needle can comprise a hollow shape. More particularly, the needle may comprise a bore with a diameter, which diameter corresponds to the inner diameter of the needle. A fluid may flow through the needle (i.e. through the bore of the needle) and out of the needle. Generally, needles with a smaller inner diameter can be advantageous for applications wherein a fluid need to flow through the needle with a high-pressure. The smaller inner diameter of the needle not only can facilitate achieving a high-pressure of the fluid but can also facilitate maintaining a small dead volume following the needle (e.g. between the needle and a component downstream the needle). However, as discussed, the smaller the needle, the higher the precision for aligning the needle with a downstream component. As discussed, the present invention can be particularly advantageous as it may facilitate the use of small needles, by providing a needle housing with an aligning component for facilitating the alignment of the needle with a downstream component, such as the needle receiving assembly.

The needle can be configured for a fluid to flow through it, wherein the fluid can be pressurized to a pressure exceeding the ambient pressure by at least 100 bar, preferably by at least 500 bar, further preferably by at least 1000 bar.

The needle can be part of a liquid chromatography system.

The needle can be part of a sampler configured to provide a sample to the chromatography system.

The at least one aligning component can be configured to increase alignment in the radial direction between the needle and the needle receiving assembly upon contact between the at least one aligning component and the needle receiving assembly if the misalignment in the radial direction between the needle and the needle receiving assembly is up to 1 mm. That is, the aligning component can be configured to correct a deviation of up to 1 mm between the needle and the needle receiving assembly in the radial direction. A person skilled in the art will appreciate that the needle housing and the aligning component can be configured to correct larger or smaller misalignments, as well. However, configuring the needle housing and the aligning component to correct larger misalignments may require increasing the size of the needle housing, which may lead to a bulkier needle housing. The above (i.e. 1 mm) may provide a good tradeoff between the maximum deviation that can be corrected and the bulkiness of the needle housing.

While in the above, the needle receiving assembly is discussed as a general component that can be provided downstream the needle, below a particular example of a needle receiving assembly will be described.

In a further aspect, the present invention relates to a needle receiving assembly for receiving a fluid (e.g., a liquid) from a needle. The needle receiving assembly comprises a fluid conducting element comprising a fluid conducting element proximal section and a fluid conducting element proximal end. Furthermore, the needle receiving assembly comprises a sealing element, wherein the sealing element is configured to receive the needle.

When reference is herein made to a needle receiving assembly, it should be understood that this term merely denotes that the assembly is configured to receive a fluid from a needle. That is, this term should not be construed to have any other requirement going beyond this configuration. In particular, the term "needle receiving assembly" is merely used in this specification to clearly differentiate this assembly from the needle assemblies which are also discussed in this specification. For sake of simplicity, the needle receiving assembly may also be referred to as a receiving assembly to simply as an assembly.

Further, when referring to the needle receiving assembly, the terms proximal and distal are used in this specification. In the context of the needle receiving assembly, when the needle is inserted, the closer an element is to the needle, the more proximal it is, and the more distanced an element is from the needle, the more distal it is. Further still, it will be understood that a sample (or a fluid) may be introduced from the needle into the needle receiving assembly. That is, the more distal an element (of the needle receiving assembly) is, the further "downstream" it is.

It will be understood that the sealing element seals the needle when the needle is received in the needle receiving assembly. However, in some embodiments, the sealing element also seals the fluid conducting element.

The fluid conducting element may be configured so that fluid (e.g., liquid) can flow through the fluid conducting element. Thus, the fluid conducting element may also be referred to as, e.g., flow element.

In some embodiments, the fluid conducting element may be, e.g., a capillary that may be used so that fluid can flow to downstream elements.

However, the fluid conducting element may also be a chromatographic column. This may be advantageous, as a volume between the needle and the chromatographic column may thus be reduced.

That is, overall, the present invention may provide a sealing element that may fulfil two different functions simultaneously. The sealing element may receive the needle, i.e., it may function as a needle seat, and furthermore, it may seal the assembly, i.e., it may function as a sealing component. Therefore, in the approach of the present invention, only one sealing component may be required.

Furthermore, the sealing element of the present invention may be advantageous, as it may allow to reduce air gaps in the assembly as a result of fewer components, which may contribute to reduce the occurrence of cavities, i.e., it may allow to reduce empty spaces or openings where fluid can flow to.

For instance, it may allow to reduce or eliminate air gaps between the sealing element and the needle as well as between the sealing element and the fluid conducting element. Reducing or eliminating air gaps may be particularly advantageous, as it may further allow to reduce dead volumes, which may in turn contribute to chromatographic improvements such as separation of analytes, separation and quantification of peaks, etc.

Moreover, the approach of the present invention may facilitate to reduce errors in assembling the components as a result of supplying a simpler assembly. In more simple words, the present invention comprises fewer components to fulfil all features of an effective sealing, with particular improvements over the prior art.

In some embodiments, the sealing element can extend along the capillary proximal section and proximally beyond the capillary proximal end.

The fluid conducting element may define an axial direction and a radial direction perpendicular to the axial direction.

The sealing element may comprise a distal portion, which may comprise a constant inner diameter.

The distal portion of the sealing element may comprise an outer diameter, which may be constant along the axial direction.

The distal portion of the sealing element may extend along the fluid conducting element proximal section and may receive the fluid conducting element proximal section.

The sealing element may comprise a proximal portion, which may comprise an outer diameter that may be greater than the outer diameter of the distal portion of the sealing element.

The change of the outer diameter of the sealing element can be advantageous as it can facilitate compressing the sealing element. More particularly, it can facilitate exerting an axial force to the sealing element, thus, compressing the sealing element. For example, the sealing element can be pressed against an inner wall of the housing of the needle receiving assembly. This contributes to better sealing it against the needle. In other words, the proximal portion having a greater outer diameter than the distal portion of the sealing element may create a shoulder surface of the sealing element that can allow exerting an axial force to the sealing element in the upstream direction and thus compressing the sealing element.

In addition, the change of the outer diameter of the sealing element can be advantageous as it can facilitate stopping or limiting the motion of the sealing element along the axial direction. In other words, the proximal portion having a greater outer diameter than the distal portion of the sealing element facilitates arranging the sealing element such that its axial motion can be limited and even blocked by another element of the needle receiving assembly (e.g. the thrust piece and securing member). This can be particularly advantageous when the needle can be received in the needle seat created by the sealing element. The needle can be pressed into the sealing element, thus exerting an axial force to the sealing element along the downstream direction. Hence, by limiting the motion of the sealing element in the axial direction the creating of a tight and non-leaking connection between the needle and the sealing element can be facilitated.

A quotient of the outer diameter of the proximal portion of the sealing element and the outer diameter of the distal portion of the sealing element may be greater than 1.2, preferably greater than 1.5, further preferably greater than 1.8, and smaller than 10, preferably smaller than 5, and further preferably smaller than 3.

Furthermore, a length of the distal portion of the sealing element along the axial direction may exceed a length of the proximal portion of the sealing element in the axial direction. That is, the distal portion of the sealing element can be provided relatively lengthy. This can be particularly advantageous in embodiments wherein the distal portion of the sealing element extends along the fluid conducting element proximal section. As such, the contact surface area between the sealing element and the fluid conducting element can be larger, hence facilitating a better sealing between the sealing element and the fluid conducting element.

A quotient of the length of the distal portion of the sealing element along the axial direction and the length of the proximal portion of the sealing element in the axial may be greater than 1.3, preferably greater than 1.5, further preferably greater than 2, and smaller than 10, preferably smaller than 5, and further preferably smaller than 3.

The proximal portion of the sealing element may comprise an inner diameter and a section with a constant inner diameter along the axial direction. The proximal portion may comprise a first section with an inner diameter tapering along the axial direction. In one embodiment, the first section with the tapering inner diameter may be more proximal than the section with the constant inner diameter.

The proximal portion may comprise a second section with an inner diameter tapering along the axial direction, wherein a taper angle may be different between the first section and second section with a tapering inner diameter.

The taper angle may be greater in the first section than in the second section. Furthermore, the second section may be the most proximal section of the sealing element.

The fluid conducting element may comprise an inner diameter and an outer diameter. The inner diameter of the fluid conducting element may be constant along the axial direction. The outer diameter of the fluid conducting element may also be constant along the axial direction.

Moreover, a quotient of the outer diameter of the fluid conducting element and the inner diameter of the fluid conducting element may be greater than 10, preferably greater than 50, further preferably greater than 100, and smaller than 500, preferably smaller than 200, and further preferably smaller than 300.

The assembly may comprise a thrust piece, which may be advantageous, as it may, for example, be plastically deformed towards the sealing element and the fluid conducting element (e.g., by crimping), which may further allow transmitting a mechanical force to the sealing element and the fluid conducting element, and therefore, further enhancing the sealing of the assembly.

The thrust piece may comprise a constant inner diameter.

The thrust piece may comprise a section with a constant outer diameter.

Moreover, the thrust piece may comprise a thrust proximal section and/or a thrust distal section The thrust distal section may comprise a thrust distal end, which may also comprise an outer diameter.

A quotient of the outer diameter of the thrust distal end and the outer diameter of the section of the thrust piece may be greater than 1.2, preferably greater than 1.5, further preferably greater than 2, and smaller than 8, preferably smaller than 6, and further preferably smaller than 4.

The assembly may comprise a fluid conducting element housing, which may comprise a housing proximal portion and/or a housing distal portion. For the sake of brevity, the fluid conducting element housing may also be referred to simply as housing.

The housing may comprise an opening arranged concentric to the sealing element and the fluid conducting element.

The housing may comprise a housing cavity accommodating the sealing element, the fluid conducting element and the thrust piece.

The assembly may comprise a securing member, which may comprise a securing member proximal section and/or a securing member distal section.

The securing member proximal section may comprise a protruding section, e.g., a thread.

Furthermore, the securing member may comprise an outer diameter at the securing member proximal section different from an outer diameter of the securing member at the securing member distal section.

The protruding section may comprise an outer diameter defined by the outer diameter of the securing member proximal section, and wherein the outer diameter of the protruding section may be greater than the outer diameter of the securing member distal section.

A quotient of the outer diameter of the protruding section and the outer diameter of the securing member distal section may be greater than 1.05, preferably greater than 1.1, further preferably greater than 1.2, and smaller than 2, preferably smaller than 1.5, and further preferably smaller than 1.4.

The securing member proximal section may comprise a securing member cavity with a diameter matching or exceeding the outer diameter of the thrust distal end to accommodate the thrust piece in the securing member.

A length of the thrust distal section of the thrust piece along the axial direction may be arranged in the securing member cavity.

The thrust piece may comprise a length in the axial direction in the range of 1 to 20 mm, preferably 2 to 15 mm, further preferably 4 to 8 mm, such as 6 mm.

A quotient of the length of the thrust distal section arranged in the securing member cavity and the length of the thrust piece may be between 0.1 and 0.8, more preferably between 0.2 and 0.6, further preferably between 0.3 and 0.5.

The securing member distal section may comprise an inner diameter to accommodate the fluid conducting element.

Furthermore, the sealing element may comprise a material with a compressive strength lower than 250 MPa, preferably lower than 150 MPa, further preferably lower than 100 MPa, wherein the sealing element may be formed of said material.

The sealing element may comprise a polymeric material, such as a high-performance plastic material comprising at least one of: a poly-ether-ether-ketone (PEEK), a poly-ether-ketone (PEK), a poly-ketone (PK), a poly-ether-ketone-ether-ether-ketone (PEKEEK), and a polyphenylene sulfide (PPS).

The sealing element can withstand an axial force exerted by the needle in the range of 5 N to 80 N, more preferably 10 N to 60 N, most preferably 20 N to 50 N.

The fluid conducting element may comprise an inner tube, which may be a fused silica tube.

As discussed, in some embodiments the fluid conducting element can be a capillary. Typically, the capillary may comprise a narrow fused silica tube. For example, the fused silica tube may comprise a constant inner diameter in the range of 1 µm to 300 µm, preferably 5 µm to 200 µm, most preferably 10 µm to 150 µm. Furthermore, the fused silica tube may comprise a constant outer diameter in the range of 150 µm to 600 µm, preferably 200 µm to 500 µm, most preferably 280 µm to 450 µm.

Alternatively, the fluid conducting element may be a chromatographic column. In such embodiments, the fused silica tube may comprise a constant inner diameter in the range of 5 µm to 10 mm, preferably 50 µm to 1 mm.

The fluid conducting element may comprise a metal or plastic fluid conducting element.

In embodiments, wherein the fluid conducting element is configured as a capillary, the metal or plastic fluid conducting element may comprise a constant inner diameter in the range of 150 µm to 700 µm, preferably 250 µm to 600 µm, most preferably 350 µm to 500 µm. Furthermore, in such embodiments, the metal or plastic fluid conducting element may comprise a constant outer diameter in the range of 0.3 mm to 1.5 mm, preferably 0.6 mm to 1.0 mm, further preferably 0.75 mm to 0.85 mm, such as 0.79 mm Alternatively, in embodiments wherein the fluid conducting element is configured as a chromatographic column, the metal or plastic fluid conducting element may comprise a constant inner diameter in the range of 150 µm to 10 mm, preferably 250 µm to 1 mm, most preferably 350 µm to 500 µm.

The fluid conducting element may comprise a sheathing layer, which comprise a sheathing proximal section and a sheathing proximal end.

In some instances, the presence of a sheathing layer may be advantageous, as it may strengthen the walls of the capillary, which may be of particular benefits for withstanding higher pressures as well as for avoiding damage of the capitally during manipulations such as, for example, mounting of the capillary in the assembly. Furthermore, the sheathing layer may supply additional means for an improved sealing of the capillary in the assembly.

The sheathing layer may comprise a polymeric material such as: a poly-ether-ether-ketone (PEEK), a poly-ether-ketone (PEK), a poly-ketone (PK), a poly-ether-ketone-ether-ether-ketone (PEKEEK), and a polyphenylene sulfide (PPS).

The sheathing layer may comprise a thickness in the range of 50 µm to 500 µm, preferably 100 µm to 300 µm, such as such as 180 µm to 200 µm.

The assembly further may comprise a filtering element, which may be arranged at the fluid conducting element proximal end.

The filtering element may be particularly advantageous, as it may allow to ensure the "quality" of the fluid (e.g. liquid) that enters the analytical device. For instance, a small portion of fluid may appear to be totally clear for a direct injection in analytical device. However, there may still be remaining small particles, e.g. particles in the micro size range, that could enter the analytical device if a filtering element were not present.

In more simple words, the filtering element may supply means to reduce or eliminate the presence of particles in the fluid to be injected in the analytical device. The presence of particles in the mobile phase may otherwise result in a plurality of undesired effects such as build-ups inside the analytical device (e.g. the fluid conducting element, the analytical columns, etc.), which may in turn affect, inter alia, the flow rate or even cause damages in other components such as pumps. Moreover, the filtering element may supply means to ensure that, e.g. air bubbles, do not enter components further downstream.

The filtering element may comprise a sintered material, synthetic material or may be formed of metal.

The synthetic material may comprise a polymeric material comprising at least one of: a poly-ether-ether-ketone (PEEK), a poly-ether-ketone (PEK), a poly-ketone (PK), a poly-ether-ketone-ether-ether-ketone (PEKEEK), and a polyphenylene sulfide (PPS).

The filtering element may be formed of stainless-steel.

The filtering element may be formed of titanium.

The filtering element may comprise pores with a pore size in the range of 0.05 $\mu m^2$ to 1,000 $\mu m^2$, preferably 0.1 $\mu m^2$ to 500 $\mu m^2$, further preferably 0.25 $\mu m2$ to 100 $\mu m2$. It should be understood that the term "pore size" is intended to refer to the area of an individual pore, and that this area is perpendicular to the flow direction of the fluid that enters the assembly. Furthermore, it should be understood that the size of a plurality of individual pores may be irregular, however, the range mentioned above is intended to refer to an average to give a mean pore size.

The sealing element may be attached to the fluid conducting element. That is, the sealing element can be firmly attached to the fluid conducting element irrespective of whether the sealing element and the fluid conducting element are arranged or secured or assembled into the needle receiving assembly. Thus, a better connection between the sealing element and the fluid conducting element can be achieved, hence decreasing the likelihood of leakage. Moreover, the needle seat attached to the fluid conducting element may be completely exchangeable (i.e. as one piece), which allows easy service and maintenance. That is, the sealing element and the fluid conducting element can be handled as one piece. Thus, the needle receiving assembly can be assembled and maintained more easily. In addition, the likelihood of a misconfiguration of the needle receiving assembly (e.g. by forgetting to provide the sealing element) is reduced.

The sealing element may surround the fluid conducting element.

The sealing element may comprise inner walls extending along the axial direction.

The sealing element may be a monolithic sealing element.

In some instances, a monolithic sealing element may be advantageous, as it may supply a better connectivity between components of the assembly, which allow to implement, for instance, higher pressures. Furthermore, it will also be understood that such a monolithic element may be a particularly simple design.

The thrust piece may surround the distal portion or the sealing element.

The thrust piece, the sealing element and the fluid conducting element can be secured to one another.

For example the thrust piece, the sealing element and the fluid conducting element can be secured to one another by crimping.

For example, the thrust piece, the sealing element and the fluid conducting element can be secured to one another by an adhesive.

Providing the thrust piece, the sealing element and the fluid conducting element can be secured to one another can facilitate servicing, maintenance, handling and/or assembling the needle receiving assembly. This may be facilitated by the fact that the thrust piece, the sealing element and the fluid conducting element secured to one another can be handled as a single piece.

The sealing element and the fluid conducting element may be secured to one another.

The sealing element and the fluid conducting element may be secured to one another by crimping.

The sealing element and the fluid conducting element may be secured to one another by an adhesive.

The thrust piece may be formed of metal.

The sealing element may surround the fluid conducting element in a section proximal to the sheathing proximal end.

An outer diameter of the sheathing layer may equal the outer diameter of the distal portion of the sealing element.

The housing cavity may comprise a cavity distal section and a cavity proximal section, wherein the cavity distal section has a distal cavity inner diameter and the cavity proximal section has a proximal cavity inner diameter.

The proximal cavity inner diameter may be smaller than the distal cavity inner diameter.

The proximal cavity inner diameter may be smaller than an outer diameter of the securing member.

The thrust piece may extend into the cavity proximal section.

The sealing element may contact an inner wall of the cavity proximal section.

The housing cavity further may comprise a proximal abutment surface, and wherein a proximal end of the sealing element may abut the proximal abutment surface.

The housing cavity further may comprise an intermediate section between the cavity distal section and the cavity proximal section.

The cavity proximal section may comprise a chamfered section adjacent to the proximal abutment surface.

The sealing element may comprise a chamfered section corresponding to the chamfered section of the cavity proximal section.

The constant outer diameter of the section of the thrust piece may equal the outer diameter of the proximal portion of the sealing element.

The securing member may be formed of metal.

The housing may be formed of metal.

An axial length of the sealing element extending proximally beyond the fluid conducting element proximal end may be greater than 0.5 mm, preferably larger than 1 mm, such as larger than 1.5 mm, and preferably smaller than 10 mm, further preferably smaller than 5 mm, such as smaller than 3 mm.

In some embodiments, the needle receiving assembly can be configured to facilitate connecting a needle of a needle assembly with the needle receiving assembly. In such embodiments, the fluid conducting element housing can comprise at least one aligning component configured to increase alignment in the radial direction between the needle and the needle receiving assembly upon contact between the at least one aligning component and the needle assembly. That is, similarly to the above discussion with respect to the needle assembly, the needle receiving assembly may also comprise at least one aligning component. It will be understood that the aligning component of the needle receiving assembly leads to similar advantages as discussed above with respect to the needle assembly. For the sake of brevity, a repetitive discussion of such advantages is omitted herein.

Moreover, in the following, different embodiments of the aligning component of the needle receiving assembly will be discussed. It will be understood that, generally, the aligning component of the needle receiving assembly may comprise a similar structure or shape as the aligning component of the needle assembly. Typically, embodiments of the aligning component of the needle receiving assembly may comprise a mirrored shape of respective embodiments of the aligning component of the needle assembly. As such, they may lead to similar advantages.

In some embodiments, the fluid conducting element housing can comprise an outer lateral surface. In such embodiments, the aligning component of the needle receiving assembly may comprise an aligning outer surface formed by at least a portion of the outer lateral surface of the fluid conducting element housing. This can be particularly advantageous if a portion of the needle receiving assembly surrounded by the lateral surface can be received in the needle assembly. This can allow the outer lateral surface of the fluid conducting element housing (wherein the aligning outer surface can be formed) to contact a surface of the needle assembly, thus, increasing alignment in the radial direction between the needle and the needle receiving assembly.

A diameter of cross sections of the aligning outer surface of the needle receiving assembly can increase continuously along the axial direction such that for any two cross sections of the aligning outer surface wherein a first cross section is more proximal than a second cross section, the diameter of the first cross section can be smaller than the diameter of the second cross section. Each cross section of the aligning outer surface can be an intersection between the aligning outer surface and a plane perpendicular to the axial direction. In other words, the diameter of the aligning outer surface can be expressed as a function of the position along the axial direction, which function is a strictly increasing function along the downstream direction. This (i.e. the continuous increase of the diameter) can facilitate a sliding motion between the needle assembly and the needle receiving assembly during the connection. In other words, there can be no section of the aligning outer surface which can resist the needle to be received in the needle receiving assembly. For example, there can be no surface of the aligning outer surface being perpendicular to the axial direction. This can be achieved by the requirement that the diameter of cross sections of the aligning outer surface can increase continuously.

The aligning outer surface can comprise a most proximal cross-section, which is more proximal than the rest of the aligning outer surface, and a most distal cross section, which is more distal than the rest of the aligning outer surface. In some embodiments, the diameter of the most proximal cross-section of the aligning outer surface can be smaller than the diameter of the rest of the cross-sections of the aligning outer surface. Thus, the diameter of the aligning outer surface can continuously increase from the most proximal cross section to the most distal cross section. The diameter of the most proximal cross-section of the aligning outer surface can be at least 30%, preferably at least 40%, more preferably at least 60% and at most 90%, such as 80% to 85% of the diameter of the most distal cross-section of the aligning outer surface.

For example, the diameter of the distal cross-section of the aligning outer surface can be at least 2 mm and at most 10 mm, preferably at most 5 mm, such as 2.5 mm to 3 mm.

The diameter of the cross sections of the aligning outer surface can decrease linearly with at least one rate.

The diameter of the cross sections of the aligning outer surface can increase linearly with a constant rate. That is, the aligning outer surface can resemble the surface of a conical frustum, wherein the base of the frustum can be more distal than the rest of the frustum. This can provide a particularly simple aligning component.

Alternatively, the diameter of the cross sections of the aligning outer surface can increase linearly with two distinct rates. That is, the aligning outer surface can comprise the shape of two joined conical frustums, such that, a top of a distal conical frustum corresponds to a base of a proximal conical frustum, wherein the proximal conical frustum is more proximal than the distal conical frustum.

The aligning outer surface can comprise a proximal aligning outer surface and a distal aligning outer surface wherein the proximal aligning outer surface can be more proximal than the distal aligning outer surface. Moreover, the diameter of the cross sections of the proximal aligning outer surface can increase with a different rate than the diameter of the cross sections of the distal aligning outer surface.

In some embodiments, the diameter of the cross sections of the proximal aligning outer surface can increase with a higher rate than the diameter of the cross sections of the distal aligning outer surface. That is, in some embodiments, the taper angle of the proximal aligning outer surface can be larger than the taper angle of the distal aligning outer surface. Thus, the aligning outer surface can be a convex surface, instead of a concave one, which can be particularly advantageous for reducing the forces opposing the reception of the needle in the needle receiving assembly.

The diameters of the cross-sections of the proximal aligning outer surface may not exceed the diameters of the cross-sections of the distal aligning outer surface.

The aligning outer surface may comprise a length along the axial direction of at least 0.1 mm and at most 10 mm, preferably at most 5 mm, more preferably at most 1 mm, such as 0.5 mm.

It will be understood, that aligning outer surface of the needle receiving assembly can also comprise at least one curved section along the axial direction, preferably forming a convex surface along the axial direction. In some embodiments, the curved section can be provided more proximal than the rest of the aligning outer surface. Alternatively or additionally, the curved section can be provided on the proximal aligning outer surface and/or on the distal aligning outer surface. Alternatively or additionally, the curved section can be provided on the transition between the proximal aligning outer surface and the distal aligning outer surface. In some embodiments, the entire aligning outer surface can be curved.

In some embodiments, the fluid conducting element housing may comprise a lateral protruding portion protruding proximally beyond the rest of the fluid conducting element housing. Thus, the fluid conducting element housing may comprise a cavity which can be laterally surrounded by the lateral protruding portion.

The lateral protruding portion may comprise a length along the axial direction in the range of 1 mm to 50 mm, preferably 2 mm to 10 mm, more preferably 3 mm to 5 mm, such as 4 mm.

The lateral protruding portion may protrude proximally beyond the rest of the fluid conducting element housing. For example, the lateral protruding portion can protrude proximally beyond the rest of the fluid conducting element housing by at least 0.5 mm and at most 10 mm, preferably by at least 1 mm and at most 5 mm, more preferably by at least 1.2 mm and at most 1.8 mm, such as 1.5 mm. This can be advantageous as it can provide sufficient distance along the axial direction for the needle and the needle receiving assembly to be aligned such that the needle can be properly received by the needle receiving assembly.

The lateral protruding portion may comprise an outer diameter in the range of 3 mm to 51 mm, more preferably 5 to 21 mm, more preferably 6 mm to 15 mm, such as, 10 mm.

The lateral protruding portion may comprise an inner diameter in the range of 2 mm to 50 mm, preferably 4 mm to 20 mm, more preferably 5 mm to 10 mm, such as 8 mm.

The lateral protruding portion may comprise an inner lateral surface that laterally surrounds a cavity of the fluid conducting element housing. That is, the lateral protruding portion protruding may form a cavity of the needle receiving assembly. Thus, an inner lateral surface of the lateral protruding portion may laterally surround the cavity.

The aligning component of the needle receiving assembly may comprise an aligning inner surface which can be formed by at least a portion of the inner lateral surface of the lateral protruding portion. This can be particularly advantageous if a portion of the needle assembly can be received in the cavity of the needle receiving assembly. This can allow the inner lateral surface of the lateral protruding portion to contact a surface of the needle assembly, thus, increasing alignment in the radial direction between the needle and the needle receiving assembly.

A diameter of the cross sections of the aligning inner surface may decrease continuously along the axial direction such that for any two cross sections of the aligning inner surface, wherein a first cross section is more proximal than a second cross section, the diameter of the first cross section can be larger than the diameter of the second cross section. Each cross section of the aligning inner surface can be an intersection between the aligning inner surface and a plane perpendicular to the axial direction.

The diameter of the cross sections of the aligning inner surface may decrease linearly with at least one rate.

In some embodiments, the diameter of the cross sections of the aligning inner surface may decrease linearly with a constant rate. That is, the aligning inner surface may comprise a conical frustum shape, wherein the base of the frustum is more proximal than the rest of the frustum.

Alternatively, the diameter of the cross sections of the aligning inner surface may decrease linearly with two distinct rates. That is, the aligning inner surface can comprise the shape of two joined conical frustums, such that, a base of the distal conical frustum corresponds to a top of the proximal conical frustum.

The aligning inner surface may comprise a proximal aligning inner surface and a distal aligning inner surface, wherein the proximal aligning inner surface is more proximal than the distal aligning inner surface and the diameter of the cross sections of the proximal aligning inner surface can decrease with a different rate than the diameter of the cross sections of the distal aligning inner surface.

The diameter of the cross sections of the proximal aligning inner surface can decrease with a higher rate than the diameter of the cross sections of the distal aligning inner surface. That is, a taper angle of the proximal aligning inner surface can be larger than a taper angle of the distal aligning inner surface.

The diameter of the cross-sections of the distal aligning inner surface may not exceed the diameter of the cross-sections of the proximal aligning inner surface.

The aligning inner surface can be positioned in a most proximal portion of the inner lateral surface of the lateral protruding portion.

The aligning inner surface can comprise at least one curved section along the axial direction, preferably forming a convex surface along the axial direction.

In some embodiments, the fluid conducting element housing may comprise a central protruding portion. The central protruding portion can be positioned more centrally than other portions of the fluid conducting element housing. For example, the central protruding portion can be concentrically aligned with the fluid conducting element. The central protruding portion can protrude proximally beyond a base of the fluid conducting element housing. The central protruding portion may comprise a length along the axial direction which can be in the range of 0.2 mm to 50 mm, preferably 1 mm to 10 mm, more preferably 1.5 to 3 mm, such as 2 mm.

The central protruding portion may comprise a length along the axial direction in the range of 20% to 100%, preferably 30% to 80%, more preferably 40% to 60% of the length of lateral protruding portion along the axial direction. In other words, the lateral protruding portion may protrude proximally beyond the central protruding portion. That is, typically (though not necessarily) the central protruding portion can protrude less than the lateral protruding portion. This can be advantageous, as it can allow the needle to be aligned with the central protruding portion (wherein it is typically received), thus, avoiding collisions between the needle and the central protruding portion.

The cavity of the needle receiving assembly can surrounds the central protruding portion. Again, as discussed, the central protruding portion can be provided in a center position of the fluid conducting element housing, thus, allowing other components of the fluid conducting element housing, such as, the cavity and the lateral protruding portion to surround it.

The central protruding portion may comprise an outer lateral surface and wherein the portion of the outer aligning surface of the fluid conducting element housing wherein the aligning outer surface can be formed, may comprise a portion of the outer lateral surface of the central protruding portion of the fluid conducting element housing. That is, the aligning outer surface of the needle receiving assembly can be formed on a portion of the outer lateral surface of the central protruding portion. This can be particularly advantageous in embodiments wherein the central protruding portion of the needle receiving assembly can be received in a cavity of the needle assembly.

In some embodiments, the aligning outer surface can be formed entirely by a portion of the outer lateral surface of the central protruding portion.

In some embodiments, the portion of the outer lateral surface of the central protruding portion wherein the aligning outer surface can be formed, can be more proximal than the rest of the central protruding portion.

The portion of the outer lateral surface of the central protruding portion wherein the aligning outer surface can be formed, can amount to at least 10%, preferably at least 20% and at most 100%, preferably at most 50%, more preferably at most 30%, such as 25% of the total extension of the central protruding portion along the axial direction.

The extension of the fluid conducting element housing in the radial direction can be in the range 3 mm to 51 mm, more preferably 5 to 21 mm, more preferably 6 mm to 15 mm, such as, 10 mm. It will be understood that these are only some typical exemplary dimensions of the fluid conducting element housing. Such dimensions may be larger (particularly in embodiments wherein the fluid conducting element is a chromatography column) or smaller.

In some embodiments, the needle can be part of the needle assembly according to the first aspect of the present invention. In such embodiments, the extension of the fluid conducting element housing in the radial direction can be 1.01 times and at most 2 times, preferably at least 1.1 times and at most 1.5 times, such as, 1.3 times the extension of the needle housing in the radial direction. This can allow the needle housing to be received in the fluid conducting element housing.

The capillary may comprise an inner diameter in the range of 5 μm to 5 mm, preferably in the range of 10 μm to 2 mm, further preferably in the range of 10 μm to 500 μm, such as in the range of 10 μm to 200 μm.

The capillary may comprise an outer diameter, which may be constant along an axial direction of the capillary.

The outer diameter may be in the range of 0.1 mm to 10 mm, preferably in the range of 0.5 mm to 4 mm, such as in the range of 0.5 mm to 2 mm.

The capillary may have a wall thickness in the range of 50 μm to 1000 μm, preferably in the range of 100 μm to 500 μm, such as in the range of 300 μm to 700 μm.

The capillary may comprise an axial length exceeding 5 cm, preferably exceeding 10 cm, such as exceeding 30 cm. Thus, the capillary may be connected to other elements being located as a substantial distance from the sealing element, without there being the necessity of providing another connecting element, such as another capillary, which would require an additional seal.

The capillary be flexible. Put differently, a user may elastically deform the capillary. This may facilitate to connect the capillary to another element.

Generally, the capillary of the present technology may omit the necessity of additional sealing point(s). This nay prevent possible leakages and reduce complexity Below, further needle assembly embodiments will be discussed.

In some embodiments, the needle assembly can be configured to connect the needle to the needle receiving assembly according to the preceding needle receiving assembly embodiments.

In some embodiments, the needle assembly can be configured such that at least a portion of the fluid conducting element housing of the needle receiving assembly can be received in the cavity of the needle assembly. Again, this can allow an aligning outer surface of the needle receiving assembly to contact the needle assembly and/or an aligning inner surface of the needle assembly to contact the needle receiving assembly.

As discussed, this can increase central alignment between the needle and the needle receiving assembly.

In such embodiments, the needle assembly can be configured such that a diameter of the cavity of the needle housing can match to an outer diameter of the portion of the fluid conducting element housing received in the cavity. Thus, the needle housing can abut the portion of the fluid conducting element housing received therein. This can reduce or eliminate motion in the radial direction between the needle receiving assembly and the needle assembly, thus, maintaining a more robust connection. At the same time, this can ensure that the alignment between the needle and the needle receiving assembly can be maintained.

In embodiments wherein the fluid conducting element housing may comprise a central protruding portion, the portion of the fluid conducting element housing received in the cavity of the needle assembly can be the central protruding portion.

The portion of the fluid conducting element housing received in the cavity of the needle assembly can comprise an outer lateral surface and the aligning inner surface of the needle housing can be configured to contact at least a portion of the outer lateral surface of the portion of the fluid conducting element housing received in the cavity during the connection.

The needle assembly can be configured such that the inner surface of the needle housing may contact the aligning outer surface of the needle receiving assembly during the connection. In some embodiments, the needle assembly can be configured such that a portion of the needle housing can be received in the cavity of the needle receiving assembly formed by the lateral protruding portion.

In such embodiments, an outer diameter of the needle housing may not exceed an inner diameter of the lateral protruding portion. Thus, the lateral protruding portion of the needle receiving assembly may surround the needle housing.

As a portion of the needle housing can be received in the cavity of the needle receiving assembly, the aligning outer surface can contact the inner lateral surface of the lateral protruding portion during the connection.

More particularly, the needle housing can comprise an outer lateral surface and the aligning inner surface of the needle receiving assembly can contact the outer lateral surface of the needle housing during the connection.

In further aspect, the present invention relates to connection assembly configured to facilitate introducing a fluid from a needle to a fluid conducting element. The connection assembly comprises the needle assembly according to any of the preceding needle assembly embodiments and the needle receiving assembly according to any of the preceding needle receiving assembly embodiments.

In a further aspect, the present invention relates to a sampler for picking up a fluid (e.g., a liquid), wherein the sampler comprises a fluid conducting element and a needle. In addition, the sampler comprises at least one of the needle receiving assembly according to any of the preceding needle receiving assembly embodiments, wherein the fluid conducting element of the sampler is the fluid conducting element of the needle receiving assembly, and the needle assembly according to any of the preceding needle assemblies, wherein the needle of the sampler is the needle of the needle assembly.

The needle may comprise a needle tip.

The needle may comprise an outer diameter in the range of 0.1 mm to 2 mm, preferably 0.3 mm to 1.8 mm, most preferably 0.5 mm to 1.6 mm.

The needle may comprise a constant inner diameter in the range of 5 μm to 500 μm, preferably 30 μm to 400 μm, most preferably 50 μm to 300 μm.

The needle may exert an axial force in the range of 5 N to 80 N, more preferably 10 N to 60 N, most preferably 20 N to 50 N.

The axial force exerted by the needle may pre-tension the material of the sealing element, which may in some instances be of particular benefit, as a pre-tensioned material may withstand high pressures in comparison to non-pretensioned materials. For instance, a pre-tensioned material may exhibit an improved resilience, which may allow the sealing element to bear higher pressures without undergoing failure. Furthermore, the pre-tension of the material of the sealing element may increase the compression of the material, which may result in less and/slower wear of the material.

The needle may mechanically deform the inner walls at the proximal portion of the sealing element forming a deformation contour, which may be beneficial, as it may supply a better, e.g., more "complete", sealing between the sealing element and the needle.

The needle tip may comprise a needle tip angle and wherein this needle tip angle may be more acute than a taper angle of the proximal portion of the sealing element.

In a further aspect, the present invention relates to a system for analyzing a liquid, the system comprising an analytical device to analyze the liquid, and the sampler as recited herein.

The analytical device may be a chromatography device.

The analytical device may be a liquid chromatography device.

The analytical device may be a high-performance liquid chromatography device.

The analytical device may be configured to be pressurized to a pressure exceeding the ambient pressure by at least 100 bar, preferably by at least 500 bar, further preferably by at least 1,000 bar.

The present invention also relates to the use of the needle assembly, the needle receiving assembly, the sampler or the system as recited herein in a chromatography system.

The chromatography system may be a liquid chromatography system.

The chromatography system may be a high-performance liquid chromatography system.

The present invention also relates to a method comprising the use of the assembly, the sampler or the system as recited herein.

The method may comprise forming the sealing element via an injection molding mechanism, which may be particularly advantageous, as it may allow to implement sealing elements with as diverse and detailed geometries as a plurality of different applications may require for a successful performance.

Furthermore, the injection molding of the sealing element may allow to implement sealing elements with enhanced properties such as, for example, a sealing element comprising materials with lower density and greater strength. Additionally or alternatively, this approach may allow forming sealing elements comprising a combination of any of the synthetic material mentioned above, i.e., the sealing element would not necessarily be formed only of one material.

The method may comprise applying on the sealing element an axial pressure greater than 50 MPa, more preferably greater than 100 MPa, further preferably greater than 150 MPa, such as 200 MPa.

The axial pressure may be exerted on the sealing element by means of screwing in the securing member in the housing and an axial force being transmitted from the securing member to the thrust piece and from the thrust piece to the sealing element.

The axial force may pre-tension the material of the sealing element, so that the sealing element can withstands pressures greater than 500 bar, more preferably higher 1000 bar, such as 1500 bar.

The method may comprise crimping the thrust piece at least to the fluid conducting element.

The thrust piece may be crimped to the fluid conducting element and to the sealing element. Crimping the fluid conducting element and the sealing element may allow to reduce or completely eliminate any gaps between the fluid conducting element and the sealing element, therefore, crimping may also contribute to reduce the dead volume.

The method may comprise connecting the thrust piece to at least the fluid conducting element via an adhesive method, such as gluing. An adhesive method may provide an additional sealing means, which may contribute to a better sealing of the assembly.

Furthermore, the adhesive may supply a more even distribution of stress, excellent cohesive strength and a better resistance to degrading processes such as corrosion. Moreover, adhesives may be tuned to exhibit a plurality of different properties that may be advantageous for the assembly, for example, adhesive may be designed to be electrical conductors or electrical insulators, exhibit enhanced sealing functions, and/or to reduce vibrations.

The securing member may be arranged in the housing via a screwing-in mechanism.

The securing member may be arranged in the housing via a direct pressing-in mechanism.

The securing member may be arranged in the housing via caulking.

The securing member may be arranged in the housing via a sliding mechanism.

The method may comprise the use of the sampler as recited herein, wherein the method may comprise pressing the needle into the sealing element with a force resulting in a pressure at the needle tip exceeding a compressive strength of the material of the sealing element.

The method may comprise the use of the needle assembly according to any of the preceding needle assembly embodiments. In such embodiments, method may comprise mounting the needle unreleasably to the needle housing of the needle assembly.

The method can comprise the use of the needle assembly according to any of the preceding needle assembly embodiments. In such embodiments, the method may comprise welding the needle to the needle housing of the needle assembly.

The method can comprise the use of the needle assembly according to any of the preceding needle assembly embodiments. In such embodiments, the method may comprise mounting the needle to the needle housing of the needle assembly via an adhesive method, such as, gluing.

The method can comprise the use of the needle assembly according to any of the preceding needle assembly embodiments. In such embodiments, the method may comprise mounting the needle to the needle housing of the needle assembly by pressing the needle against the needle housing.

The needle assembly can be configured for the use according to any of the preceding use embodiments or the method according to any of the preceding method embodiments.

The needle receiving assembly can be configured for the use according to any of the preceding use embodiments or the method according to any of the preceding method embodiments.

The present technology is also defined by the following numbered embodiments.

Below, needle assembly embodiments will be discussed. These embodiments are abbreviated by a number. When reference is herein made to needle assembly embodiments, these embodiments are meant.

1. A needle assembly (200) for facilitating connecting a needle (202) and a needle receiving assembly (100), wherein the needle assembly (200) comprises:
    the needle (202), wherein the needle defines an axial direction and wherein a tip of the needle (202) is more proximal than the rest of the needle (202) and a radial direction perpendicular to the axial direction;
    a needle housing (2040) comprising a cavity (2050) and wherein the cavity is occupied in part by the needle (202);
    wherein the needle housing (2040) comprises at least one aligning component (2044) configured to increase alignment in the radial direction between the needle (202) and the needle receiving assembly (100) upon contact between the at least one aligning component (2044) and the needle receiving assembly (100).

Aligning Outer Surface of the Needle Housing

2. The needle assembly (200) according to the preceding embodiment,
    wherein the needle housing (2040) comprises an outer lateral surface and
    wherein the aligning component (2044) of the needle housing (2040) comprises an aligning outer surface (2044A) formed by at least a portion of the outer lateral surface of the needle housing (2040).

3. The needle assembly (200) according to the preceding embodiment, wherein a diameter of cross sections of the aligning outer surface (2044A) decreases continuously along the axial direction such that
    for any two cross sections of the aligning outer surface (2044A) wherein a first cross section is more proximal than a second cross section, the diameter of the first cross section is smaller than the diameter of the second cross section,
    wherein each cross section of the aligning outer surface (2044A) is an intersection between the aligning outer surface (2044A) and a plane perpendicular to the axial direction.

4. The needle assembly (200) according to the preceding embodiment, wherein the aligning outer surface (2044A) comprises a most distal cross-section, which is more distal than the rest of the aligning outer surface (2044A), and a most proximal cross section, which is more proximal than the rest of the aligning outer surface (2044A) and wherein
    the diameter of the most distal cross-section of the aligning outer surface (2044A) is larger than the diameter of the rest of the cross-sections of the aligning outer surface (2044A) and wherein
    the diameter of the most proximal cross-section of the aligning outer surface (2044A) is at least 30%, preferably at least 40%, more preferably at least 60% and at most 90%, such as 80% to 85% of the diameter of the most distal cross-section of the aligning outer surface (2044A).

5. The needle assembly (200) according to the preceding embodiment, wherein the diameter of the distal cross-section of the aligning outer surface (2044A) corresponds to the largest extension of the needle housing (2040) along the radial direction.

6. The needle assembly (200) according to any of the 2 preceding embodiments, wherein the diameter of the distal cross-section of the aligning outer surface (2044A) is in the range of 2 mm to 50 mm, preferably 4 mm to 20 mm, more preferably 5 mm to 10 mm, such as 7.5 mm.

7. The needle assembly (200) according to any of the 4 preceding embodiments, wherein the diameter of the cross sections of the aligning outer surface (2044A) decreases linearly with at least one rate.

8. The needle assembly (200) according to any of the 5 preceding embodiments, wherein the diameter of the cross sections of the aligning outer surface (2044A) decreases linearly with a constant rate.

9. The needle assembly (200) according to the preceding embodiment, wherein the aligning outer surface (2044A) comprises a conical frustum shape.

10. The needle assembly (200) according to any of the embodiments 3 to 7, wherein the diameter of the cross sections of the aligning outer surface (2044A) decreases linearly with two distinct rates.

11. The needle assembly (200) according to the preceding embodiment, wherein the aligning outer surface (2044A) comprises the shape of two joined conical frustums, such that, a top of a distal conical frustum corresponds to a base of a proximal conical frustum,
    wherein the proximal conical frustum is more proximal than the distal conical frustum.

12. The needle assembly (200) according to any of the 2 the preceding embodiments, wherein the aligning outer surface (2044A) comprises a proximal aligning outer surface (3005) and a distal aligning outer surface (3006) wherein
    the proximal aligning outer surface (3005) is more proximal than the distal aligning outer surface (3006) and
    the diameter of the cross sections of the proximal aligning outer surface (3005) decreases with a different rate than the diameter of the cross sections of the distal aligning outer surface (3006).

13. The needle assembly (200) according to the preceding embodiment, wherein the diameter of the cross sections of the proximal aligning outer surface (3005) decreases with a higher rate than the diameter of the cross sections of the distal aligning outer surface (3006).

That is, in some embodiments, the taper angle of the proximal aligning outer surface is larger than the taper angle of the distal aligning outer surface.

14. The needle assembly (200) according to any of the 2 preceding embodiments, wherein the diameter of the cross-sections of the proximal aligning outer surface (3005) do not exceed the diameter of the cross-sections of the distal aligning outer surface (3006).

15. The needle assembly (200) according to any of the 13 preceding embodiments, wherein the aligning outer surface (2044A) amounts to at least 5% and at most 60%, such as, 30% of the extension along the axial direction of the needle housing (2040).

16. The needle assembly (200) according to any of the 14 preceding embodiments, wherein the aligning outer surface (2044) comprises a length along the axial direction of at least 0.5 mm and at most 20 mm, preferably at most 10 mm, more preferably at most 5 mm, such as 1 mm.

17. The needle assembly (200) according to any of the embodiments 3 to 6, wherein the aligning outer surface (2044A) comprises at least one curved section (2044AC) along the axial direction, preferably forming a convex surface (2044AC) along the axial direction.

Distal Portion of the Needle Housing

18. The needle assembly (200) according to any of the preceding embodiments, wherein the needle housing (2040) comprises a distal portion (2042) wherein the distal portion (2042) is more distal than the rest of the needle housing (2040).

19. The needle assembly (200) according to the preceding embodiment, wherein a plurality of cross sections of the distal portion (2042) comprise the same outer diameter wherein a cross section of the distal portion (2042) is an intersection between the distal portion (2042) and a plane perpendicular to the axial direction.

20. The needle assembly (200) according to any of the 2 preceding embodiments, wherein the distal portion (2042) comprises a width along the radial direction that corresponds to the largest extension along the radial direction of the needle housing (2040).

21. The needle assembly (200) according to any of the 3 preceding embodiments, wherein the distal portion (2042) comprises a width along the radial direction in the range of 2 mm to 50 mm, preferably 4 mm to 20 mm, more preferably 5 mm to 10 mm, such as 7.5 mm.

22. The needle assembly (200) according to any of the 4 preceding embodiments, wherein the distal portion (2042) amounts to at least 40% and at most 80%, such as, 65% of the extension along the axial direction of the needle housing (2040).

23. The needle assembly (200) according to any of the 5 preceding embodiments, wherein the distal portion (2042) comprises a length along the axial direction in the range of 0.5 mm to 40 mm, preferably 1 mm to 10 mm, more preferably 2 mm to 5 mm, such as 2.3 mm.

24. The needle assembly (200) according to any of the 6 preceding embodiments and with the features of embodiment 2, wherein the aligning outer surface (2044A) is provided more proximal than the distal portion (2042).

25. The needle assembly (200) according to the preceding embodiment, wherein the diameters of the cross sections of the aligning outer surface (2044A) do not exceed the width along the radial direction of the distal portion (2042) wherein each cross section of the aligning outer surface (2044A) is an intersection between the aligning outer surface (2044A) and a plane perpendicular to the axial direction.

Proximal Portion and Protrusion of the Needle Housing

26. The needle assembly (200) according to any of the preceding embodiments, wherein the needle housing (2040) further comprises a proximal portion (2046) wherein the proximal portion (2046) is more proximal than the rest of the needle housing (2040).

27. The needle assembly (200) according to the preceding embodiment wherein the proximal portion (2046) amounts to at least 1% and at most 20%, preferably 5% to 8% of the extension along the axial direction of the needle housing (2040).

28. The needle assembly (200) according to any of the 2 preceding embodiments and with the features of embodiments 2 and 18, wherein the aligning outer surface (2044A) is between the distal portion (2042) and the proximal portion (2046).

29. The needle assembly (200) according to the preceding embodiment, wherein the extension along the radial direction of the proximal portion (2046) does not exceed the extension along the radial direction of the aligning outer surface (2044A).

30. The needle assembly (200) according to any of the 4 preceding embodiments and with the features of embodiment 2, wherein the aligning outer surface (2044A) extends along the axial direction up to and including the proximal portion (2046).

31. The needle assembly (200) according to any of the 5 preceding embodiments, wherein the proximal portion (2046) protrudes proximally beyond the tip of the needle (202).

It should be understood that this feature, i.e., the proximal portion of the needle housing protruding proximally beyond the tip of the needle, may also be employed independently from the aligning component. That is, there are also embodiments of the present invention, wherein the needle housing does not necessarily comprise an aligning components as discussed above. Instead, the proximal protrusion beyond the tip of the needle may also be employed independently from the aligning component.

32. The needle assembly (200) according to the preceding embodiment, wherein the length along the axial direction of the proximal portion (2046) protruding proximally beyond the tip of the needle (202) is in the range of 0.1 mm to 2 mm, preferably 0.2 mm to 1 mm, such as 0.25 mm.

Aligning Inner Surface of the Needle Housing

33. The needle assembly (200) according to any of the preceding embodiments,
wherein the needle housing (2040) comprises an inner surface that laterally encloses the cavity (2050).

34. The needle assembly (200) according to the preceding embodiment wherein the aligning component (2044) comprises an aligning inner surface (2044B) formed by at least a portion of the inner surface that laterally encloses the cavity (2050).

35. The needle assembly (200) according to the preceding embodiment, wherein a diameter of the cross sections of the aligning inner surface (2044B) increases continuously along the axial direction such that
for any two cross sections of the aligning inner surface (2044B), wherein a first cross section is more proximal than a second cross section, the diameter of the first cross section is larger than the diameter of the second cross section,
wherein each cross section of the aligning inner surface (2044B) is an intersection between the aligning inner surface (2044B) and a plane perpendicular to the axial direction.

36. The needle assembly (200) according to the preceding embodiment, wherein the diameter of the cross sections of the aligning inner surface (2044B) increases linearly with at least one rate.

37. The needle assembly (200) according to any of the 2 preceding embodiments, wherein the diameter of the cross sections of the aligning inner surface (2044B) increases linearly with a constant rate.

38. The needle assembly (200) according to the preceding embodiment, wherein the aligning inner surface (2044B) comprises a conical frustum shape.

39. The needle assembly (200) according to any of the embodiments 35 and 36, wherein the diameter of the cross sections of the aligning inner surface (2044B) increases linearly with two distinct rates. 40. The needle assembly (200) according to the preceding embodiment, wherein the aligning inner surface (2044B) comprises the shape of two joined conical frustums, such that, a base of the distal conical frustum corresponds to a top of the proximal conical frustum.

41. The needle assembly (200) according to any of the 2 the preceding embodiments, wherein the aligning inner surface (2044B) comprises a proximal aligning inner surface (3001) and a distal aligning inner surface (3002) wherein
the proximal aligning inner surface (3001) is more proximal than the distal aligning inner surface (3002) and
the diameter of the cross sections of the proximal aligning inner surface (3001) increases with a different rate than the diameter of the cross sections of the distal aligning inner surface (3002).

42. The needle assembly (200) according to the preceding embodiment, wherein the diameter of the cross sections of the proximal aligning inner surface (3001) increases with a higher rate than the diameter of the cross sections of the distal aligning inner surface (3002).

43. The needle assembly (200) according to any of the 2 preceding embodiments, wherein the diameter of the cross-sections of the distal aligning inner surface (3002) do not exceed the diameter of the cross-sections of the proximal aligning inner surface (3001).

44. The needle assembly (200) according to any of the 10 preceding embodiments and with the features of embodiment 26, wherein the aligning inner surface (2044B) is positioned in the proximal portion (2046) of the needle housing (2040).

45. The needle assembly (200) according to the preceding embodiment, wherein the aligning inner surface (2044B) extends along at least 30%, preferably at least 60%, more preferably at least 80% of the length along the axial direction of the proximal portion (2046).

46. The needle assembly (200) according to embodiment 35, wherein the aligning inner surface (2044B) comprises at least one curved section (2044BC) along the axial direction, preferably forming a convex surface (2044BC) along the axial direction.

Materials

47. The needle assembly (200) according to any of the preceding embodiments, wherein the needle (202) comprises a metallic, quartz glass and/or fused silica material.

48. The needle assembly (200) according to any of the preceding embodiments, wherein the needle housing (2040) comprises a metallic or polymetric material, such as, poly-ether-ether-ketone (PEEK), poly-ether-ketone (PEK), poly-ether-ether-ether-ketone (PEEEK) and a polyphenylene sulfide (PPS).

Mounting of Needle

49. The needle assembly (200) according to any of the preceding embodiments, wherein the needle (202) is unreleasably mounted on the needle housing (2040).

50. The needle assembly (200) according to the preceding embodiment, wherein the needle (202) comprises a metallic material and the needle housing (2040) comprises a metallic material and the needle (202) is welded to the needle housing (2040).

51. The needle assembly (200) according to the penultimate embodiment, wherein the needle (202) is pressed into the needle housing (2040).

Dimension of Needle Housing

52. The needle assembly (200) according to any of the preceding embodiments, wherein the needle housing (2040) comprises an extension along the radial direction between 2 times to 100 times, preferably 5 times to 20 times, more preferably 8 times to 12 times the outer diameter of the needle (202).

53. The needle assembly (200) according to any of the preceding embodiments, wherein the needle housing (2040) comprises an extension along the radial direction in the range of 2 mm to 50 mm, preferably 4 mm to 20 mm, more preferably 5 mm to 10 mm, such as 7.5 mm.

54. The needle assembly (200) according to any of the preceding embodiments, wherein the needle housing (2040) comprises an extension along the axial direction in the range of 1 mm to 50 mm, preferably 2 mm to 10 mm.

Dimensions of the Needle

55. The needle assembly (200) according to any of the preceding embodiments, wherein the outer diameter of the needle (202) is in the range of 0.1 mm to 2 mm, preferably 0.3 mm to 1.8 mm, more preferably between 0.5 mm to 1.6 mm.

56. The needle assembly (200) according to any of the preceding embodiments, wherein the inner diameter of the needle (202) is in the range of 5 µm to 500 µm, preferably 30 µm to 400 µm, more preferably 50 µm to 300 µm.

Pressure Range

57. The needle assembly (200) according to any of the preceding embodiments, wherein the needle is configured for a fluid to flow through it, wherein the fluid is pressurized to a pressure exceeding the ambient pressure by at least 100 bar, preferably by at least 500 bar, further preferably by at least 1000 bar.

58. The needle assembly (200) according to any of the preceding embodiments, wherein the needle (202) is part of a liquid chromatography system.

59. The needle assembly (200) according to the preceding embodiment, wherein the needle (202) is part of a sampler configured to provide a sample to the chromatography system.

Tolerance of Aligning Component

60. The needle assembly (200) according to any of the preceding embodiments, wherein the at least one aligning component (2044) is configured to increase alignment in the radial direction between the needle (202) and the needle receiving assembly (100) upon contact between the at least one aligning component (2044) and the needle receiving assembly (100)
if the misalignment in the radial direction between the needle (202) and the needle receiving assembly (100) is up to 1 mm.

Below, needle receiving assembly embodiments will be discussed. These embodiments are abbreviated by the letter "A" followed by a number. In some instances, the letter "A" is followed by a number and a letter. When reference is herein made to needle receiving assembly embodiments, these embodiments are meant.

A0. A needle receiving assembly (100) for receiving a fluid from a needle (202), wherein the needle receiving assembly (100) comprises
a fluid conducting element (20) comprising a fluid conducting element proximal section (26) and a fluid conducting element proximal end (28); and
a sealing element (10);
wherein the sealing element (10) is configured to receive the needle (202).

A0a. A needle receiving assembly (100) according to the preceding embodiment, wherein the fluid conducting element (20) is a capillary (20).

A0b. A needle receiving assembly (100) according to embodiment A0, wherein the fluid conducting element (20) is a chromatographic column (20).

When reference is herein made to a needle receiving assembly, it should be understood that this term merely denotes that the assembly is configured to receive a fluid from a needle. That is, this term should not be construed to have any other requirement going beyond this configuration. In particular, the term "needle receiving assembly" is merely used in this specification to clearly differentiate this assembly from the needle assemblies which are also discussed in this specification. For sake of simplicity, the needle receiving assembly may also be referred to as a receiving assembly to simply as an assembly.

Further, when referring to the needle receiving assembly, the terms proximal and distal are used in this specification. In the context of the needle receiving assembly, when the needle is inserted, the closer an element is to the needle, the more proximal it is, and the more distanced an element is from the needle, the more distal it is. Further still, it will be understood that a sample (or a fluid) may be introduced from the needle into the needle receiving assembly. That is, the more distal an element (of the needle receiving assembly) is, the further "downstream" it is.

It will be understood that the sealing element seals the needle when the needle is received in the needle receiving assembly. However, in some embodiments, the sealing element also seals the fluid conducting element.

A1. The needle receiving assembly (100) according to preceding embodiment, wherein the sealing element (10) extends along the fluid conducting element proximal section (26) and proximally beyond the fluid conducting element proximal end (28).

A2. The needle receiving assembly (100) according to preceding embodiment, wherein the fluid conducting element (20) defines an axial direction and a radial direction perpendicular to the axial direction.

A3. The needle receiving assembly (100) according to any of the preceding needle receiving assembly embodiments, wherein the sealing element (10) comprises a distal portion (12).

A4. The needle receiving assembly (100) according to the preceding embodiment, wherein the distal portion (12) of the sealing element (10) comprises a constant inner diameter.

A5. The needle receiving assembly (100) according to any of the two preceding embodiments, wherein the distal portion (12) of the sealing element (10) comprises an outer diameter.

A6. The needle receiving assembly (100) according to the preceding embodiment and with the features of embodiment A2, wherein the outer diameter of the distal portion (12) of the sealing element (10) is constant along the axial direction.

A7. The needle receiving assembly (100) according to any of the four preceding embodiments, wherein the distal portion (12) of the sealing element (10) extends along the fluid conducting element proximal section (26).

A8. The needle receiving assembly (100) according to any of the five preceding embodiments, wherein the distal portion (12) of the sealing element (10) receives the fluid conducting element proximal section (26).

A9. The needle receiving assembly (100) according to any of the preceding needle receiving assembly embodiments, wherein the sealing element (10) comprises a proximal portion (14).

A10. The needle receiving assembly (100) according to the preceding embodiment and with the features of embodiment A5, wherein the proximal portion (14) of the sealing element (10) comprises an outer diameter that is greater than the outer diameter of the distal portion (12) of the sealing element (10).

A11. The needle receiving assembly (100) according to the preceding embodiment, wherein a quotient of the outer diameter of the proximal portion (14) of the sealing element (10) and the outer diameter of the distal portion (12) of the sealing element (10) is greater than 1.2, preferably greater than 1.5, further preferably greater than 1.8, and smaller than 10, preferably smaller than 5, and further preferably smaller than 3.

A12. The needle receiving assembly (100) according to any of the preceding needle receiving assembly embodiments with the features of embodiments A2, A3 and A9, wherein a length of the distal portion (12) of the sealing element (10) along the axial direction exceeds a length of the proximal portion (14) of the sealing element (10) in the axial direction.

A13. The needle receiving assembly (100) according to the preceding embodiment, wherein a quotient of the length of the distal portion (12) of the sealing element (10) along the axial direction and the length of the proximal portion (14) of the sealing element (10) in the axial is greater than 1.3, preferably greater than 1.5, further preferably greater than 2, and smaller than 10, preferably smaller than 5, and further preferably smaller than 3.

A14. The needle receiving assembly (100) according to any of the preceding needle receiving assembly embodiments with the features of embodiments A9, wherein the proximal portion (14) of the sealing element (10) comprises an inner diameter.

A15. The needle receiving assembly (100) according to any of the preceding needle receiving assembly embodiments and with the features of embodiment A2, wherein the proximal portion (14) comprises a section with a constant inner diameter along the axial direction.

A16. The needle receiving assembly (100) according to any of the preceding needle receiving assembly embodiments, wherein the proximal portion (14) comprises a first section (16) with an inner diameter tapering along the axial direction.

A17. The needle receiving assembly (100) according to the preceding embodiment and with the features of the penultimate embodiment, wherein the first section (16) with the tapering inner diameter is more proximal than the section with the constant inner diameter.

A18. The needle receiving assembly (100) according to any of the 2 preceding embodiments, wherein the proximal portion (14) comprises a second section (18) with an inner diameter tapering along the axial direction, wherein a taper angle is different between the first section (16) and second section (18) with a tapering inner diameter.

A19. The needle receiving assembly (100) according to the preceding embodiment, wherein the taper angle is greater in the first section (16) than in the second section (18).

A20. The needle receiving assembly (100) according to any of the 2 preceding embodiments, wherein the second section (18) is the most proximal section of the sealing element (10).

A21. The needle receiving assembly (100) according to any of the preceding needle receiving assembly embodiments and with features of embodiment A2, wherein the fluid conducting element (20) comprises an inner diameter.

A22. The needle receiving assembly (100) according to the preceding embodiment, wherein the inner diameter of the fluid conducting element (20) is constant along the axial direction.

A23. The needle receiving assembly (100) according to any of the preceding needle receiving assembly embodiments and with features of embodiment A2, wherein the fluid conducting element (20) comprises an outer diameter.

A24. The needle receiving assembly (100) according to the preceding embodiment, wherein the outer diameter of the fluid conducting element (20) is constant along the axial direction.

A25. The needle receiving assembly (100) according to the preceding embodiment, wherein a quotient of the outer diameter of the fluid conducting element (20) and the inner diameter of the fluid conducting element (20) is greater than 10, preferably greater than 50, further preferably greater than (100), and smaller than 500, preferably smaller than (200), and further preferably smaller than 300.

A26. The needle receiving assembly (100) according to any of the preceding needle receiving assembly embodiments, wherein the needle receiving assembly (100) comprises a thrust piece (30).

A27. The needle receiving assembly (100) according to the preceding embodiment, wherein the thrust piece (30) comprises a constant inner diameter.

A28. The needle receiving assembly (100) according to any of the two preceding embodiments, wherein the thrust piece (30) comprises a section with a constant outer diameter.

A29. The needle receiving assembly (100) according to any of the preceding needle receiving assembly embodiments and with features of embodiment A26, wherein the thrust piece (30) comprises a thrust proximal section (34).

A30. The needle receiving assembly (100) according to any of the preceding needle receiving assembly embodiments and with features of embodiment A26, wherein the thrust piece (30) comprises a thrust distal section (36).

A31. The needle receiving assembly (100) according to the preceding embodiment, wherein the thrust distal section (36) comprises a thrust distal end (38).

A32. The needle receiving assembly (100) according to the preceding embodiment, wherein the thrust distal end (38) comprises an outer diameter.

A33. The needle receiving assembly (100) according to the preceding embodiment and with features of embodiment A28, wherein a quotient of the outer diameter of the thrust distal end (38) and the outer diameter of the section of the thrust piece (30) is greater than 1.2, preferably greater than 1.5, further preferably greater than 2, and smaller than 8, preferably smaller than 6, and further preferably smaller than 4.

A34. The needle receiving assembly (100) according to any of the preceding needle receiving assembly embodiments, wherein the needle receiving assembly (100) comprises a fluid conducting element housing (40).

A35. The needle receiving assembly (100) according to the preceding embodiment, wherein the fluid conducting element housing (40) comprises a housing proximal portion (42).

A36. The needle receiving assembly (100) according to any of the 2 preceding embodiments, wherein the fluid conducting element housing (40) comprises a housing distal portion (44).

A37. The needle receiving assembly (100) according to any of the 3 preceding embodiments, wherein the fluid conducting element housing (40) comprises an opening (46) arranged concentric to the sealing element (10) and the fluid conducting element (20).

A38. The needle receiving assembly (100) according to any of the 4 preceding embodiments, wherein the fluid conducting element housing (40) comprises a housing cavity (48) accommodating the sealing element (10), the fluid conducting element (20) and the thrust piece (30).

A39. The needle receiving assembly (100) according to any of the preceding needle receiving assembly embodiments, wherein the needle receiving assembly (100) comprises a securing member (60).

A40. The needle receiving assembly (100) according to the preceding embodiment, wherein the securing member (60) comprises a securing member proximal section (62).

A41. The needle receiving assembly (100) according to the preceding embodiment, wherein the securing member proximal section (62) comprises a protruding section (66), e.g., a thread.

A42. The needle receiving assembly (100) according to any of the 3 preceding embodiments, wherein the securing member (60) comprises a securing member distal section (64).

A43. The needle receiving assembly (100) according to the preceding embodiment and with the features of embodiment A40, wherein the securing member (60) comprises an outer diameter at the securing member proximal section (62) different from an outer diameter of the securing member (60) at the securing member distal section (64).

A44. The needle receiving assembly (100) according to the preceding embodiment and with the features of embodiment A41, wherein the protruding section (66) comprises an outer diameter defined by the outer diameter of the securing member proximal section (62), and wherein the outer diameter of the protruding section (66) is greater than the outer diameter of the securing member distal section (64).

A45. The needle receiving assembly (100) according to the preceding embodiment and with features of embodiment A42, wherein a quotient of the outer diameter of the protruding section (66) and the outer diameter of the securing member distal section (64) is greater than 1.05, preferably greater than 1.1, further preferably greater than 1.2, and smaller than 2, preferably smaller than 1.5, and further preferably smaller than 1.4.

A46. The needle receiving assembly (100) according to any of the preceding needle receiving assembly embodiments and with the features of embodiment A32 and A40, wherein the securing member proximal section (62) comprises a securing member cavity (622) with a diameter matching or exceeding the outer diameter of the thrust distal end (28) to accommodate the thrust piece (30) in the securing member (60).

A47. The needle receiving assembly (100) according to the preceding embodiment and with the features of embodiments A2 and A30, wherein a length of the thrust distal section (36) of the thrust piece (30) along the axial direction is arranged in the securing member cavity (622).

A48. The needle receiving assembly (100) according to any of the preceding needle receiving assembly embodiments and with features of embodiment A2 and A26, wherein the thrust piece (30) comprises a length in the axial direction in the range of 1 to 20 mm, preferably 2 to 15 mm, further preferably 4 to 8 mm, such as 6 mm.

A49. The needle receiving assembly (100) according to any of the two preceding embodiments, wherein a quotient of the length of the thrust distal section (36) arranged in the securing member cavity (622) and the length of the thrust piece (30) is between 0.1 and 0.8, more preferably between 0.2 and 0.6, further preferably between 0.3 and 0.5.

A50. The needle receiving assembly (100) according to any of the preceding needle receiving assembly embodiments with the features of embodiment A42, wherein the securing member distal section (64) comprises an inner diameter to accommodate the fluid conducting element (20).

A51. The needle receiving assembly (100) according to any of the preceding needle receiving assembly embodiments, wherein the sealing element (10) comprises a material with a compressive strength lower than 250 MPa, preferably lower than 150 MPa, further preferably lower than (100) MPa.

A52. The needle receiving assembly (100) according to the preceding embodiment, wherein the sealing element (10) is formed of said material.

A53. The needle receiving assembly (100) according to any of the preceding needle receiving assembly embodiments, wherein the sealing element (10) comprises a polymeric material, such as a high-performance plastic material comprising at least one of: a poly-ether-ether-ketone (PEEK), a poly-ether-ketone (PEK), a poly-ketone (PK), a poly-ether-ketone-ether-ether-ketone (PEKEEK), and a polyphenylene sulfide (PPS).

A54. The needle receiving assembly (100) according to the preceding embodiment, wherein the sealing element (10) can withstand an axial force exerted by the needle (202) in the range of 5 N to 80 N, more preferably 10 N to 60 N, most preferably 20 N to 50 N.

A55. The needle receiving assembly (100) according to any of the preceding needle receiving assembly embodiments, wherein the fluid conducting element (20) comprises an inner tube (22).

A56. The needle receiving assembly (100) according to the preceding embodiment, wherein the inner tube (22) is a fused silica tube.

A57. The needle receiving assembly (100) according to the preceding embodiment and with the features of embodiment A0a, wherein the fused silica tube comprises a constant inner diameter in the range of 1 µm to 300 µm, preferably 5 µm to (200) µm, most preferably 10 µm to 150 µm.

A57a. The needle receiving assembly (100) according to the penultimate embodiment and with the features of embodiment A0b, wherein the fused silica tube comprises a constant inner diameter in the range of 5 µm to 10 mm, preferably 50 µm to 1 mm.

A58. The needle receiving assembly (100) according to any of the two the preceding embodiments and with the features of embodiment A0a, wherein the fused silica tube comprises a constant outer diameter in the range of 150 µm to 600 µm, preferably (200) µm to 500 µm, most preferably 280 µm to 450 µm.

A59. The needle receiving assembly (100) according to any of the embodiments A1 to A54, wherein the fluid conducting element (20) comprises a metal or plastic fluid conducting element.

A60. The needle receiving assembly (100) according to the preceding embodiment and with the features of embodiment A0a, wherein the metal or plastic fluid conducting element comprises a constant inner diameter in the range of 150 µm to 700 µm, preferably 250 µm to 600 µm, most preferably 350 µm to 500 µm.

A60a. The needle receiving assembly (100) according to the penultimate embodiment and with the features of embodiment A0b, wherein the metal or plastic fluid conducting element comprises a constant inner diameter in the range of 150 µm to 10 mm, preferably 250 µm to 1 mm, most preferably 350 µm to 500 µm.

A61. The needle receiving assembly (100) according to any of the two preceding embodiments and with the features of embodiment A0a, wherein the metal or plastic fluid conducting element comprises a constant outer diameter in the range of 0.3 mm to 1.5 mm, preferably 0.6 mm to 1.0 mm, further preferably 0.75 mm to 0.85 mm, such as 0.79 mm A62. The needle receiving assembly (100) according to any of the preceding needle receiving assembly embodiments, wherein the fluid conducting element (20) comprises a sheathing layer (24).

A63. The needle receiving assembly (100) according to the preceding embodiment, wherein the sheathing layer (24) comprises a sheathing proximal section (242) and a sheathing proximal end (244).

A64. The needle receiving assembly (100) according to any of the 2 the preceding embodiments, wherein the sheathing layer (24) comprises a polymeric material such as: a poly-ether-ether-ketone (PEEK), a poly-ether-ketone (PEK), a poly-ketone (PK), a poly-ether-ketone-ether-ether-ketone (PEKEEK), and a polyphenylene sulfide (PPS).

A65. The assembly according (100) according to any of the 3 preceding embodiments, wherein the sheathing layer (24) comprises a thickness in the range of 50 µm to 500 µm, preferably (100) µm to 300 µm, such as such as 180 µm to (200) µm.

A66. The needle receiving assembly (100) according to any of the preceding needle receiving assembly embodiments, wherein the needle receiving assembly (100) further comprises a filtering element (70).

A67. The needle receiving assembly (100) according to the preceding embodiment, wherein the filtering element (70) is arranged at the fluid conducting element proximal end (28).

A68. The needle receiving assembly (100) according to any of the two the preceding embodiments, wherein the filtering element (70) comprises a sintered material.

A69. The needle receiving assembly (100) according to any of embodiments A66 and A67, wherein the filtering element (70) comprises a synthetic material.

A70. The needle receiving assembly (100) according to the preceding embodiment, wherein the synthetic material comprises a polymeric material comprising at least one of: a poly-ether-ether-ketone (PEEK), a poly-ether-ketone (PEK), a poly-ketone (PK), a poly-ether-ketone-ether-ether-ketone (PEKEEK), and a polyphenylene sulfide (PPS).

A71. The needle receiving assembly (100) according to any of embodiments A66 and A67, wherein the filtering element (70) is formed of metal.

A72. The needle receiving assembly (100) according the preceding embodiment, wherein the filtering element (70) is formed of stainless-steel.

A73. The needle receiving assembly (100) according the embodiment 71, wherein the filtering element (70) is formed of titanium.

A74. The needle receiving assembly (100) according to any of the embodiments A66 to A73, wherein the filtering element (70) comprises pores with a pore size in the range of 0.05 µm² to 1,000 µm², preferably 0.1 µm² to 500 µm², further preferably 0.25 µm² to (100) µm².

A75. The needle receiving assembly (100) according to any of the preceding needle receiving assembly embodiments, wherein the sealing element (10) is attached to the fluid conducting element (20).

A76. The needle receiving assembly (100) according to any of the preceding needle receiving assembly embodiments, wherein the sealing element (10) surrounds the fluid conducting element (20).

A77. The needle receiving assembly according to any of the preceding needle receiving assembly embodiments with the features of embodiment A2, wherein the sealing element (10) comprises inner walls (204) extending along the axial direction.

A78. The needle receiving assembly according to any of the preceding needle receiving assembly embodiments, wherein the sealing element (10) is a monolithic sealing element.

A79. The needle receiving assembly according to any of the preceding needle receiving assembly embodiments with the features of embodiments A3, A26, wherein the thrust piece (30) surrounds the distal portion (12) of the sealing element (10).

A80. The needle receiving assembly according to the preceding embodiment, wherein the thrust piece (30), the sealing element (10) and the fluid conducting element (20) are secured to one another.

A81. The needle receiving assembly according to the preceding embodiment, wherein the thrust piece (30), the sealing element (10) and the fluid conducting element (20) are secured to one another by crimping.

A82. The needle receiving assembly according to the preceding embodiment, wherein the thrust piece (30), the sealing element (10) and the fluid conducting element (20) are secured to one another by an adhesive.

A83. The needle receiving assembly according to any of the preceding needle receiving assembly embodiments with the features of embodiment A26, wherein the thrust piece (30) is formed of a metal.

A84. The needle receiving assembly according to any of the preceding needle receiving assembly embodiments with the features of embodiment A63, wherein the sealing element (10) surrounds the fluid conducting element (20) in a section proximal to the sheathing proximal end (244).

A85. The needle receiving assembly according to the preceding embodiment and with the features of embodiment A5, wherein an outer diameter of the sheathing layer (24) equals the outer diameter of the distal portion (12) of the sealing element (10).

A86. The needle receiving assembly according to any of the preceding needle receiving assembly embodiments with the features of embodiment A38, wherein the housing cavity (48) comprises a cavity distal section (482) and a cavity proximal section (484), wherein the cavity distal section (482) has a distal cavity inner diameter and the cavity proximal section (484) has a proximal cavity inner diameter.

A87. The needle receiving assembly according to the preceding embodiment, wherein the proximal cavity inner diameter is smaller than the distal cavity inner diameter.

A88. The needle receiving assembly according to any of the 2 preceding embodiments and with the features of embodiment A39, wherein the proximal cavity inner diameter is smaller than an outer diameter of the securing member (60).

A89. The needle receiving assembly according to any of the 3 preceding embodiments, wherein the assembly comprises the features of embodiment A26, wherein the thrust piece (30) extends into the cavity proximal section (484).

A90. The needle receiving assembly according to any of the 4 preceding embodiments, wherein the sealing element (10) contacts an inner wall of the cavity proximal section (484).

A91. The needle receiving assembly according to any of the 5 preceding embodiments, wherein the housing cavity (48) further comprises a proximal abutment surface (486), and wherein a proximal end of the sealing element (20) abuts the proximal abutment surface (486).

A92. The needle receiving assembly according to any of the 6 preceding embodiments, wherein the housing cavity further comprises an intermediate section (483) between the cavity distal section (482) and the cavity proximal section (484).

A93. The needle receiving assembly according to any of the preceding needle receiving assembly embodiments with the features of embodiment A91, wherein the cavity proximal section (484) comprises a chamfered section (485) adjacent to the proximal abutment surface (487).

A94. The needle receiving assembly according to the preceding embodiment, wherein the sealing element (10) comprises a chamfered section corresponding to the chamfered section (485) of the cavity proximal section (484).

A95. The needle receiving assembly according to any of the preceding needle receiving assembly embodiments with the features of embodiments A10 and A28, wherein the constant outer diameter of the section of the thrust piece (30) equals the outer diameter of the proximal portion (14) of the sealing element (10).

A96. The needle receiving assembly according to any of the preceding needle receiving assembly embodiments with the features of embodiment A39, wherein the securing member (60) is formed of metal.

A97. The needle receiving assembly according to any of the preceding needle receiving assembly embodiments with the features of embodiment A34, wherein the housing (60) is formed of metal.

A98. The needle receiving assembly according to any of the preceding needle receiving assembly embodiments, wherein an axial length of the sealing element (10) extending proximally beyond the fluid conducting element proximal end (28) is greater than 0.5 mm, preferably larger than 1 mm, such as larger than 1.5 mm, and preferably smaller than 10 mm, further preferably smaller than 5 mm, such as smaller than 3 mm.

Aligning Component of the Needle Receiving Assembly

A99. The needle receiving assembly (100) according to any of the preceding needle receiving assembly embodiments and with the features of embodiments A2 and A34,
wherein the needle receiving assembly (100) is configured to facilitate connecting a needle (202) of a needle assembly (200) with the needle receiving assembly (100) and
wherein the fluid conducting element housing (40) comprises at least one aligning component (1044) configured to increase alignment in the radial direction between the needle (202) and the needle receiving assembly (100) upon contact between the at least one aligning component (1044) and the needle assembly (200).

Aligning Outer Surface of the Fluid Conducting Element Housing

A100. The needle receiving assembly (100) according to the preceding embodiment,
wherein the fluid conducting element housing (40) comprises an outer lateral surface and
wherein the aligning component (1044) comprises an aligning outer surface (1044A) formed by at least a portion of the outer lateral surface of the fluid conducting element housing (40).

A101. The needle receiving assembly (100) according to the preceding embodiment, wherein a diameter of cross sections of the aligning outer surface (1044A) increase continuously along the axial direction such that
for any two cross sections of the aligning outer surface (1044A) wherein a first cross section is more proximal than a second cross section, the diameter of the first cross section is smaller than the diameter of the second cross section,
wherein each cross section of the aligning outer surface (2044A) is an intersection between the aligning outer surface (2044A) and a plane perpendicular to the axial direction.

A102. The needle receiving assembly (100) according to the preceding embodiment, wherein the aligning outer surface (1044A) comprises a most proximal cross-section, which is more proximal than the rest of the aligning outer surface (1044A), and a most distal cross section, which is more distal than the rest of the aligning outer surface (1044A) and wherein the diameter of the most proximal cross-section of the aligning outer surface (1044A) is smaller than the diameter of the rest of the cross-sections of the aligning outer surface (1044A) and wherein the diameter of the most proximal cross-section of the aligning outer surface (1044A) is at least 30%, preferably at least 40%, more preferably at least 60% and at most 90%, such as 80% to 85% of the diameter of the most distal cross-section of the aligning outer surface (1044A).

A103. The needle receiving assembly (100) according to the preceding embodiment, wherein the diameter of the distal cross-section of the aligning outer surface (1044A) is at least 2 mm and at most 10 mm, preferably at most 5 mm, such as 2.5 mm to 3 mm.

A104. The needle receiving assembly (100) according to any of the 3 preceding embodiments, wherein the diameter of the cross sections of the aligning outer surface (1044A) increases linearly with at least one rate.

A105. The needle receiving assembly (100) according to any of the 4 preceding embodiments, wherein the diameter of the cross sections of the aligning outer surface (1044A) increases linearly with a constant rate.

A106. The needle receiving assembly (100) according to the preceding embodiment, wherein the aligning outer surface (1044A) comprises a conical frustum shape.

A107. The needle receiving assembly (100) according to any of the embodiments A101 to A103, wherein the diameter of the cross sections of the aligning outer surface (1044A) increases linearly with two distinct rates.

A108. The needle receiving assembly (100) according to the preceding embodiment, wherein the aligning outer surface (1044A) comprises the shape of two joined conical frustums, such that, a top of a distal conical frustum corresponds to a base of a proximal conical frustum, wherein the proximal conical frustum is more proximal than the distal conical frustum.

A109. The needle receiving assembly (100) according to any of the 2 the preceding embodiments, wherein the aligning outer surface (1044A) comprises a proximal aligning outer surface (1006) and a distal aligning outer surface (1005) wherein the proximal aligning outer surface (1006) is more proximal than the distal aligning outer surface (1005) and the diameter of the cross sections of the proximal aligning outer surface (1006) increase with a different rate than the diameter of the cross sections of the distal aligning outer surface (1005).

A110. The needle receiving assembly (100) according to the preceding embodiment, wherein the diameter of the cross sections of the proximal aligning outer surface (1006) increases with a higher rate than the diameter of the cross sections of the distal aligning outer surface (1005).

That is, in some embodiments, the taper angle of the proximal aligning outer surface (1006) is larger than the taper angle of the distal aligning outer surface (1005).

A111. The needle receiving assembly (100) according to any of the 2 preceding embodiments, wherein the diameters of the cross-sections of the proximal aligning outer surface (1006) do not exceed the diameters of the cross-sections of the distal aligning outer surface (1005).

A112. The needle assembly (200) according to any of the 12 preceding embodiments, wherein the aligning outer surface (1044) comprises a length along the axial direction of at least 0.1 mm and at most 10 mm, preferably at most 5 mm, more preferably at most 1 mm, such as 0.5 mm.

A113. The needle receiving assembly (100) according to any of the embodiments A100 to A103, wherein the aligning outer surface (1044A) comprises at least one curved section (1044AC) along the axial direction, preferably forming a convex surface (1044AC) along the axial direction.

Lateral Protruding Portion of the Needle Receiving Assembly

A114. The needle receiving assembly (100) according to any of the preceding needle receiving assembly embodiments and with the features of embodiment A34, wherein the fluid conducting element housing (40) comprises a lateral protruding portion (1040) protruding proximally beyond the rest of the fluid conducting element housing (40).

A115. The needle receiving assembly (100) according to the preceding embodiment, wherein the lateral protruding portion (1040) comprises a length along the axial direction in the range of 1 mm to 50 mm, preferably 2 mm to 10 mm, more preferably 3 mm to 5 mm, such as 4 mm.

A116. The needle receiving assembly (100) according to any of the 2 preceding embodiments, wherein the lateral protruding portion (1040) protrudes proximally beyond the rest of the fluid conducting element housing (40) by at least 0.5 mm and at most 10 mm, preferably by at least 1 mm and at most 5 mm, more preferably by at least 1.2 mm and at most 1.8 mm, such as 1.5 mm.

A117. The needle receiving assembly (100) according to any of the 3 preceding embodiments, wherein the lateral protruding portion (1040) comprises an outer diameter in the range of 3 mm to 51 mm, more preferably 5 to 21 mm, more preferably 6 mm to 15 mm, such as, 10 mm.

A118. The needle receiving assembly (100) according to any of the 4 preceding embodiments, wherein the lateral protruding portion (1040) comprises an inner diameter in the range of 2 mm to 50 mm, preferably 4 mm to 20 mm, more preferably 5 mm to 10 mm, such as 8 mm.

A119. The needle receiving assembly (100) according to any of the 5 preceding embodiments, wherein the lateral protruding portion (1040) comprises an inner lateral surface that laterally surrounds a cavity (1050) of the fluid conducting element housing (40).

Aligning Inner Surface of the Needle Receiving Assembly

A120. The needle receiving assembly (100) according to the preceding embodiment and with the features of embodiment A99, wherein the aligning component (1044) comprises an aligning inner surface (1044B) formed by at least a portion of the inner lateral surface of the lateral protruding portion (1040).

A121. The needle receiving assembly (100) according to the preceding embodiment, wherein a diameter of the cross sections of the aligning inner surface (1044B) decreases continuously along the axial direction such that for any two cross sections of the aligning inner surface (1044B), wherein a first cross section is more proximal than a second cross section, the diameter of the first cross section is larger than the diameter of the second cross section, wherein each cross section of the aligning inner surface (1044B) is an intersection between the aligning inner surface (1044B) and a plane perpendicular to the axial direction.

A122. The needle receiving assembly (100) according to the preceding embodiment, wherein the diameter of the cross sections of the aligning inner surface (1044B) decrease linearly with at least one rate.

A123. The needle receiving assembly (100) according to any of the 2 preceding embodiments, wherein the diameter of the cross sections of the aligning inner surface (1044B) decrease linearly with a constant rate.

A124. The needle receiving assembly (100) according to the preceding embodiment, wherein the aligning inner surface (1044B) comprises a conical frustum shape.

A125. The needle receiving assembly (100) according to embodiment A121, wherein the diameter of the cross sections of the aligning inner surface (1044B) decreases linearly with two distinct rates.

A126. The needle receiving assembly (100) according to the preceding embodiment, wherein the aligning inner surface (1044B) comprises the shape of two joined conical frustums, such that, a base of the distal conical frustum corresponds to a top of the proximal conical frustum.

A127. The needle receiving assembly (100) according to any of the 2 preceding embodiments, wherein the aligning inner surface (1044B) comprises a proximal aligning inner surface (1002) and a distal aligning inner surface (1001) wherein
the proximal aligning inner surface (1002) is more proximal than the distal aligning inner surface (1001) and
the diameter of the cross sections of the proximal aligning inner surface (1002) decreases with a different rate than the diameter of the cross sections of the distal aligning inner surface (1001).

A128. The needle receiving assembly (100) according to the preceding embodiment, wherein the diameter of the cross sections of the proximal aligning inner surface (1002) decreases with a higher rate than the diameter of the cross sections of the distal aligning inner surface (1001).

A129. The needle receiving assembly (100) according to any of the 2 preceding embodiments, wherein the diameter of the cross-sections of the distal aligning inner surface (1001) do not exceed the diameter of the cross-sections of the proximal aligning inner surface (1002).

A130. The needle receiving assembly (100) according to any of the 10 preceding embodiments, wherein the aligning inner surface (1044B) is positioned in a most proximal portion of the inner lateral surface of the lateral protruding portion (1040).

A131. The needle receiving assembly (100) according to embodiment A121, wherein the aligning inner surface (1044B) comprises at least one curved section (1044BC) along the axial direction, preferably forming a convex surface (1044BC) along the axial direction.

Central Protruding Portion

A132. The needle receiving assembly (100) according to any of the preceding needle receiving assembly embodiments and with the features of embodiment A34, wherein the fluid conducting element housing (40) comprises a central protruding portion (1060)
wherein the central protruding portion (1060) is positioned more centrally than other portions of the fluid conducting element housing (40) and
wherein the central protruding portion (1060) protrudes proximally beyond a base (1080) of the fluid conducting element housing (40).

A133. The needle receiving assembly (100) according to the preceding embodiment, wherein the central protruding portion (1060) comprises a length along the axial direction is in the range of 0.2 mm to 50 mm, preferably 1 mm to 10 mm, more preferably 1.5 to 3 mm, such as 2 mm.

A134. The needle receiving assembly (100) according to any of the 2 preceding embodiments and with the features of embodiment A114, wherein the central protruding portion (1060) comprises a length along the axial direction in the range of 20% to 100%, preferably 30% to 80%, more preferably 40% to 60% of the length of lateral protruding portion (1040) along the axial direction.

A135. The needle receiving assembly (100) according to any of the 3 preceding embodiments and with the features of embodiment A114, wherein the lateral protruding portion (1040) protrudes proximally beyond the central protruding portion.

A136. The needle receiving assembly (100) according to any of the 4 preceding embodiments and with the features of embodiment A119, wherein the cavity (1050) of the needle receiving assembly (100) surrounds the central protruding portion (1060).

A137. The needle receiving assembly (100) according to any of the 5 preceding embodiments and with the features of embodiment A100,
wherein the central protruding portion (1060) comprises an outer lateral surface and
wherein the portion of the outer aligning surface of the fluid conducting element housing (40) wherein the aligning outer surface (1044A) is formed, comprises a portion of the outer lateral surface of the central protruding portion (1060) of the fluid conducting element housing (40).

A138. The needle receiving assembly (100) according to the preceding embodiment, wherein the aligning outer surface (1044A) is formed entirely by a portion of the outer lateral surface of the central protruding portion (1060).

A139. The needle receiving assembly (100) according to any of the 2 preceding embodiments, wherein the portion of the outer lateral surface of the central protruding portion (1060) wherein the aligning outer surface (1044A) is formed, is more proximal than the rest of the central protruding portion (1060).

A140. The needle receiving assembly (100) according to any of the 3 preceding embodiments, wherein the portion of the outer lateral surface of the central protruding portion (1060) wherein the aligning outer surface (1044A) is formed amounts to at least 10%, preferably at least 20% and at most 100%, preferably at most 50%, more preferably at most 30%, such as 25% of the total extension of the central protruding portion (1060) along the axial direction.

Dimensions

A141. The needle receiving assembly (100) according to any of the preceding needle receiving assembly embodiments and with the features of embodiment A2, wherein the extension of the fluid conducting element housing (40) in the radial direction is in the range 3 mm to 51 mm, more preferably 5 to 21 mm, more preferably 6 mm to 15 mm, such as, 10 mm.

A142. The needle receiving assembly (100) according to any of the preceding needle receiving assembly embodiments and with the features of embodiment A2,
wherein the needle (202) is part of a needle assembly (200) according to any of the preceding needle assembly embodiments, and
wherein the extension of the fluid conducting element housing (40) in the radial direction is 1.01 times and at most 2 times, preferably at least 1.1 times and at most 1.5 times, such as, 1.3 times the extension of the needle housing (2040) in the radial direction.

A143. The needle receiving assembly (100) according to any of the preceding needle receiving assembly embodiments, wherein the liquid is a fluid.

A144. The needle receiving assembly (100) according to any of the preceding needle receiving embodiments with the features of embodiment A0a, wherein the capillary comprises an inner diameter in the range of 5 µm to 5 mm, preferably in the range of 10 µm to 2 mm, further preferably in the range of 10 µm to 500 µm, such as in the range of 10 µm to 200 µm.

A145. The needle receiving assembly (100) according to any of the preceding needle receiving embodiments with the features of embodiment A0a, wherein the capillary comprises an outer diameter, which may be constant along an axial direction of the capillary.

A146. The needle receiving assembly (100) according to the preceding embodiment, wherein the outer diameter is in the range of 0.1 mm to 10 mm, preferably in the range of 0.5 mm to 4 mm, such as in the range of 0.5 mm to 2 mm.

A147. The needle receiving assembly (100) according to any of the preceding needle receiving embodiments with the features of embodiment A0a, wherein the capillary has a wall thickness in the range of 50 µm to 1000 µm, preferably in the range of 100 µm to 500 µm, such as in the range of 300 µm to 700 µm. A148. The needle receiving assembly (100) according to any of the preceding needle receiving embodiments with the features of embodiment A0a, wherein the capillary comprises an axial length exceeding 5 cm, preferably exceeding 10 cm, such as exceeding 30 cm.

A149. The needle receiving assembly (100) according to any of the preceding needle receiving embodiments with the features of embodiment A0a, wherein the capillary is flexible.

Below, further needle assembly embodiments will be discussed.

Connection Between Needle Assembly and Needle Receiving Assembly

61. The needle assembly (200) according to any of the preceding needle assembly embodiments, wherein the needle assembly (200) is configured to connect the needle (202) to a needle receiving assembly (100) according to any of the preceding needle receiving assembly embodiments with the features of embodiment A34.

Portion of Fluid Conducting Element Housing Received in Cavity of Needle Housing 62. The Needle Assembly (200) According to the Preceding Embodiment, Wherein the needle assembly (200) is configured such that at least a portion of the fluid conducting element housing (40) of the needle receiving assembly (100) is received in the cavity (2050) of the needle assembly (200).

63. The needle assembly (200) according to any the preceding embodiment,
wherein the needle assembly (200) is configured such that a diameter of the cavity (2050) of the needle housing (2040) matches to an outer diameter of the portion of the fluid conducting element housing (40) received in the cavity (2050).

64. The needle assembly (200) according to any of the 2 preceding embodiments,
wherein the needle receiving assembly (100) comprises the features of embodiment A132, and
wherein the portion of the fluid conducting element housing (40) received in the cavity (2050) of the needle assembly (200) is the central protruding portion (1060).

65. The needle assembly (200) according to any of the 3 preceding embodiments and with the features of embodiment 34,
wherein the portion of the fluid conducting element housing (40) received in the cavity (2050) of the needle assembly (200) comprises an outer lateral surface and the aligning inner surface (2044B) of the needle housing (2040) is configured to contact at least a portion of the outer lateral surface of the portion of the fluid conducting element housing (40) received in the cavity (2050) during the connection.

66. The needle assembly (200) according to any of the 4 preceding embodiments and with the features of embodiment 33,
wherein the needle receiving assembly (100) comprises the features of embodiments A100 or A137, and
wherein the needle assembly (200) is configured such that the inner surface of the needle housing (2040) contacts the aligning outer surface (1044A) of the needle receiving assembly (100) during the connection.

Needle Housing Received in the Cavity of Fluid Conducting Element Housing

67. The Needle Assembly (200) According to any of the Preceding Needle Assembly embodiments and with the features of embodiment 61,
wherein the needle receiving assembly (100) comprises the features of embodiment A119, and
wherein the needle assembly (200) is configured such that a portion of the needle housing (2040) is received in the cavity (1050) of the needle receiving assembly (100) formed by the lateral protruding portion (1040).

68. The needle assembly (200) according to the preceding embodiment, wherein an outer diameter of the needle housing (2040) does not exceed an inner diameter of the lateral protruding portion (1040).

69. The needle assembly (200) according to any of the 2 preceding embodiments and with the features of embodiment 2, wherein the aligning outer surface (2044A) contacts the inner lateral surface of the lateral protruding portion (1040) during the connection.

70. The needle assembly (200) according to any of the 3 preceding embodiments,
wherein the needle receiving assembly (100) comprises the features of embodiment A120, and
wherein the needle housing (2040) comprises an outer lateral surface and
wherein the aligning inner surface (1044B) of the needle receiving assembly (100) contacts the outer lateral surface of the needle housing (2040) during the connection.

Below, connection assembly embodiments will be discussed. These embodiments are abbreviated by the letter "C" followed by a number. When reference is herein made to connection assembly embodiments, these embodiments are meant.

C1. A connection assembly configured to facilitate introducing a fluid from a needle (202) to a fluid conducting element (20), comprising
the needle assembly (200) according to any of the preceding needle assembly embodiments; and
the needle receiving assembly (100) according to any of the preceding needle receiving assembly embodiments.

Below, sampler embodiments will be discussed. These embodiments are abbreviated by the letter "T" followed by a number. When reference is herein made to a sampler embodiment, those embodiments are meant.

T0. A sampler for picking up a fluid, wherein the sampler comprises a fluid conducting element and a needle, wherein the sampler comprises at least one of
the needle receiving assembly according to any of the preceding needle receiving assembly embodiments, wherein the fluid conducting element of the sampler is the fluid conducting element of the needle receiving assembly, and the needle assembly according to any of the preceding needle assemblies, wherein the needle of the sampler is the needle of the needle assembly.

T1. The sampler according to the preceding embodiment, wherein the sampler comprises
the needle receiving assembly according to any of the preceding needle receiving embodiments.

T2. The sampler according to the preceding embodiment, wherein the needle (202) comprises a needle tip (208).

T3. The sampler according to preceding sampler embodiment, wherein the needle tip (208) comprises a tip diameter in the range of 0.1 mm to 1 mm, preferably 0.2 mm to 0.8 mm, such as 0.25 mm.

T4. The sampler according to any of the preceding sampler embodiments, wherein the needle (202) comprises an outer diameter in the range of 0.1 mm to 2 mm, preferably 0.3 mm to 1.8 mm, most preferably 0.5 mm to 1.6 mm.

T5. The sampler according to any of the preceding sampler embodiments, wherein the needle (202) comprises a constant inner diameter in the range of 5 μm to 500 μm, preferably 30 μm to 400 μm, most preferably 50 μm to 300 μm.

T6. The sampler according to any of the preceding sampler embodiments, wherein the needle (202) exerts an axial force in the range of 5 N to 80 N, more preferably 10 N to 60 N, most preferably 20 N to 50 N.

T7. The sampler according to the preceding embodiment, wherein the axial force exerted by the needle (202) pre-tensions the material of the sealing element (10).

T8. The sampler according to any of the preceding sampler embodiments, wherein the needle receiving assembly comprises the features of embodiment A77, wherein the needle (202) mechanically deforms the inner walls (204) at the proximal portion (14) of the sealing element (10) forming a deformation contour.

T9. The sampler according to any of the preceding sampler embodiments with the features of T2, wherein the needle receiving assembly comprises the features of embodiment A9, wherein the needle tip (208) comprises a needle tip angle and wherein this needle tip angle is more acute than a taper angle of the proximal portion (14) of the sealing element (10).

T10. The sampler according to any of the preceding sampler embodiments, wherein the fluid is a liquid.

Below, system embodiments will be discussed. These embodiments are abbreviated by the letter "S" followed by a number. When reference is herein made to a system embodiment, those embodiments are meant.

S1. A system for analyzing a liquid, the system comprising
an analytical device to analyze the liquid, and
the sampler according to any of the preceding sampler embodiments.

S2. The system according to the preceding embodiment, wherein the analytical device is a chromatography device.

S3. The system according to any of the preceding system embodiments, wherein the analytical device is a liquid chromatography device.

S4. The system according to any of the preceding system embodiments, wherein the analytical device is a high-performance liquid chromatography device.

S5. The system according to any of the preceding system embodiments, wherein the analytical device is configured to be pressurized to a pressure exceeding the ambient pressure by at least (100) bar, preferably by at least 500 bar, further preferably by at least 1,000 bar.

Below, use embodiments will be discussed. These embodiments are abbreviated by the letter "U" followed by a number. When reference is herein made to a use embodiment, these embodiments are meant.

U1. Use of the needle assembly (200) according to any of the needle assembly embodiments, the needle receiving assembly (100) according to any of the preceding needle receiving assembly embodiments, the connection assembly according to any of the preceding connection assembly embodiments, the sampler according to any of the preceding sampler embodiments, or the system according to any of the preceding system embodiments in a chromatography system.

U2. Use according to the preceding embodiment, wherein the chromatography system is a liquid chromatography system.

U3. Use according to the preceding embodiment, wherein the chromatography system is a high-performance liquid chromatography system.

Below, method embodiments will be discussed. These embodiments are abbreviated by the letter "M" followed by a number. When reference is herein made to a method embodiment, those embodiments are meant.

M1. A method comprising the use of the needle assembly (200) according to any of the preceding needle assembly embodiments, the needle receiving assembly (100) according to any of the preceding needle receiving assembly embodiments, the connection assembly according to any of the preceding connection assembly embodiments, the sampler according to any of the preceding sampler embodiments or the system according to any of the preceding system embodiments.

M2. The method according to preceding embodiment, wherein the method comprises forming the sealing element (10) via an injection molding mechanism.

M3. The method according to preceding embodiment, wherein the method comprises applying on the sealing element (10) an axial pressure greater than 50 MPa, more preferably greater than (100) MPa, further preferably greater than 150 MPa, such as (200) MPa.

M4. The method according to the preceding embodiment, wherein the needle receiving assembly (100) comprises the features of embodiments A26, A34, and A39, wherein the axial pressure is exerted on the sealing element (10) by means of screwing in the securing member (60) in the housing (40) and an axial force being transmitted from the securing member (60) to the thrust piece (30) and from the thrust piece (30) to the sealing element (10).

M5. The method according to preceding embodiment, wherein the axial force pre-tensioned the material of the sealing element (10), so that the sealing element (10) can withstands pressures greater than 500 bar, more preferably higher 1000 bar, such as 1500 bar.

M6. The method according to any of the preceding method embodiments, wherein the needle receiving assembly (100) comprises the features of embodiment A26, wherein the method comprises crimping the thrust piece (30) at least to the fluid conducting element (20).

M7. The method according to the preceding embodiment, wherein the thrust piece (30) is crimped to the fluid conducting element (20) and to the sealing element (10).

M8. The method according to any of the embodiments M1 to M5, wherein the needle receiving assembly (100) comprises the features of embodiment A26, wherein the method comprises connecting the thrust piece (30) to at least the fluid conducting element (20) via an adhesive method, such as gluing.

M9. The method according to any of the preceding method embodiments, wherein the needle receiving assembly (100) comprises the features of embodiments A34 and A39, wherein the securing member (60) is arranged in the housing (40) via a screwing-in mechanism.

M10. The method according to any of the embodiments M1 to M8, wherein the needle receiving assembly (100) comprises the features of embodiments A34 and A39, wherein the securing member (60) is arranged in the housing (40) via a direct pressing-in mechanism.

M11. The method according to any of the embodiments M1 to M8, wherein the needle receiving assembly (100) comprises the features of embodiments A34 and A39, wherein the securing member (60) is arranged in the housing (40) via caulking.

M12. The method according to any of the embodiments M1 to M8, wherein the needle receiving assembly (100) comprises the features of embodiments A34 and A39, wherein the securing member (60) is arranged in the housing (40) via a sliding mechanism.

M13. The method according to any of the preceding method embodiments, wherein the method comprises the use of the sampler according to any of the preceding sampler embodiments with the features of embodiment T2, wherein the method comprises pressing the needle (202) into the sealing element (10) with a force resulting in a pressure at the needle tip (208) exceeding a compressive strength of the material of the sealing element (10).

M14. The method according to any of the preceding method embodiments, wherein the method comprises the use of the needle assembly (200) according to any of the preceding needle assembly embodiments, wherein the method comprises mounting the needle (202) unreleasably to the needle housing (2040) of the needle assembly (200).

M15. The method according to any of the preceding method embodiments, wherein the method comprises the use of the needle assembly (200) according to any of the preceding needle assembly embodiments, wherein the method comprises welding the needle (202) to the needle housing (2040) of the needle assembly (200).

M16. The method according to any of the preceding method embodiments, wherein the method comprises the use of the needle assembly (200) according to any of the preceding needle assembly embodiments, wherein the method comprises mounting the needle (202) to the needle housing (2040) of the needle assembly (200) via an adhesive method, such as, gluing.

M17. The method according to any of the preceding method embodiments, wherein the method comprises the use of the needle assembly (200) according to any of the preceding needle assembly embodiments, wherein the method comprises mounting the needle (202) to the needle housing (2040) of the needle assembly (200) by pressing the needle against the needle housing (2040).

71. The needle assembly (200) according to any of the preceding needle assembly embodiments, wherein the needle assembly (200) is configured for the use according to any of the preceding use embodiments or the method according to any of the preceding method embodiments.

A143. The needle receiving assembly (100) according to any of the preceding needle receiving assembly embodiments, wherein the assembly is configured for the use according to any of the preceding use embodiments or the method according to any of the preceding method embodiments.

BRIEF DESCRIPTION OF THE DRAWINGS

FIG. 3b depicts a longitudinal section of a needle assembly and a needle receiving assembly according to embodiments of the present invention wherein the needle receiving assembly comprises an aligning inner surface;

FIGS. 5a to 5d depict longitudinal sections of a needle assembly and a needle receiving assembly according to embodiments of the present invention wherein the needle assembly comprises an aligning outer surface;

DETAILED DESCRIPTION OF EMBODIMENTS

In the following, exemplary embodiments of the invention will be described, referring to the figures. These examples are provided to give further understanding of the invention, without limiting its scope.

In the following description, a series of features and/or steps are described. The skilled person will appreciate that unless explicitly required and/or unless requires by the context, the order of features and steps is not critical for the resulting configuration and its effect. Further, it will be apparent to the skilled person that irrespective of the order of features and steps, the presence or absence of time delay between steps can be present between some or all of the described steps.

It is noted that not all the drawings carry all the reference signs. Instead, in some of the drawings, some of the reference signs have been omitted for sake of brevity and simplicity of illustration. Embodiments of the present invention will now be described with reference to the accompanying drawings.

Figure 7A:
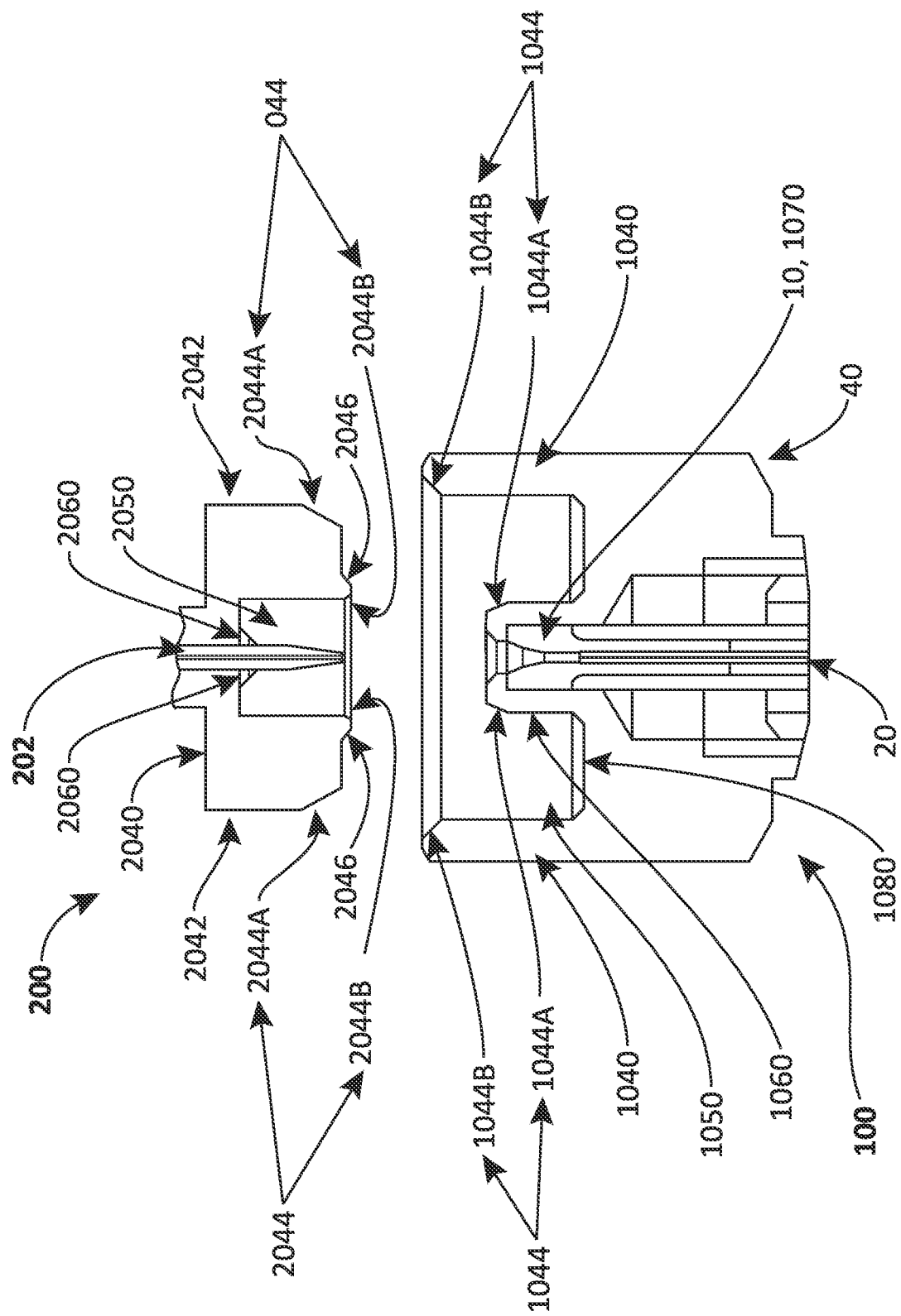
FIGS. 7a to 7f depict longitudinal sections of a needle assembly and a needle receiving assembly according to embodiments of the present invention.

Generally and referring to all the figures, embodiments of the present invention relate to facilitating a connection between a needle 202 and a fluid conducting element 20 (see, e.g., FIG. 7a). It will be understood that the fluid conducting element 20 may be configured so that fluid (e.g., liquid) can flow through the fluid conducting element 20. Thus, the fluid conducting element may also be referred to as, e.g., flow element 20. For sake of simplicity, the fluid conducting element 20 may also simply be referred to as element 20. The fluid conducting element 20 may be, e.g., a capillary that may be used so that fluid can flow to downstream elements. However, the fluid conducting element 20 may also be a chromatographic column. This may be advantageous, as a volume between the needle 202 and the chromatographic column may thus be reduced.

That is, embodiments of the present invention relate to facilitating a connection between a needle 202 and a capillary 20 or between a needle 202 and a chromatographic column 20.

It will be understood that the needle 202 and the fluid conducting element 20 may be part of a liquid chromatography system. For example, the needle 202 and the fluid conducting element 20 can be part of a sampler to (e.g. automatically) provide a sample to the chromatography system.

Such a sampler may comprise (or be associated with) a controller. The controller can be operatively connected to other components, e.g., to the sampler.

The controller can include a data processing unit and may be configured to control the system and carry out particular method steps. The controller can send or receive electronic signals for instructions. The controller can also be referred to as a microprocessor. The controller can be contained on an integrated-circuit chip. The controller can include a processor with memory and associated circuits. A microprocessor is a computer processor that incorporates the functions of a central processing unit on a single integrated circuit (IC), or sometimes up to a plurality of integrated circuits, such as 8 integrated circuits. The microprocessor may be a multipurpose, clock driven, register based, digital integrated circuit that accepts binary data as input, processes it according to instructions stored in its memory and provides results (also in binary form) as output. Microprocessors may contain both combinational logic and sequential digital logic. Microprocessors operate on numbers and symbols represented in the binary number system.

More particularly, the needle 202 may be moved to a sample vial, may draw in the sample from therein and may subsequently be moved towards the fluid conducting element 20. Then, a fluid connection between the needle 202 and the fluid conducting element 20 may be established to allow the sample to flow from the needle 202 to the fluid conducting element 20. The connection between the needle 202 and the fluid conducting element 20 can typically be configured to be non-leaking and able to withstand high pressures, e.g., pressures greater than 500 bar, preferably greater than 1000 bar, such as 1500 bar. This is advantageous for withstanding the high pressures generally present in chromatography systems, such as high-performance liquid chromatography systems.

To facilitate the connection between the needle 202 and the fluid conducting element 20, embodiments of the present invention provide a needle assembly 200 comprising the needle 202 and/or a needle receiving assembly 100 comprising the fluid conducting element 20. That is, it will be understood that embodiments of the present invention are directed to the needle assembly 200 as such, to the needle receiving assembly 100 as such and to their combination.

The needle 202 and the fluid conducting element 20 can define an axial direction. More particularly, the length of the needle 202 and the fluid conducting element 20 (when aligned with each other) can define the axial direction. In other words, the axial direction is parallel to the direction of flow from the needle 202 to the fluid conducting element 20. For an example, in FIG. 1a, the axial direction is illustrated by the line A1. Although illustrated only in FIG. 1a, this definition of the axial direction is valid also for the other figures and the rest of the specification. Furthermore, a radial direction can be defined perpendicular to the axial direction. That is, the radial direction can be perpendicular to the needle 202 and to the fluid conducting element 20. In other words, the radial direction can be perpendicular to the direction of flow from the needle 202 to the fluid conducting element 20.

Throughout the specification, the terms proximal and distal will be used to describe positions along the axial direction. The term proximal is defined as situated (i.e. positioned) nearer to the point of attachment and the term distal is defined as situated (i.e. positioned) away from the point of attachment. Within the context of the present invention, the point of attachment refers to the point wherein the needle 202 is connected to the fluid conducting element 20 (or where these components are closest to one another when the needle receiving assembly 100 and the needle assembly 200 are connected to one another) and/or to the point wherein the needle assembly 200 is connected to the needle receiving assembly 100. As will be understood, moving from a distal position to a proximal position within the needle assembly 200 (illustrated by arrow A3 in FIG. 1a) corresponds to an opposite direction as moving from a distal position to a proximal position within the needle receiving assembly 100 (illustrated by arrow A2 in FIG. 1a). This is due to the fact that the needle assembly 200 and the needle receiving assembly 100 approach the point of attachment from opposite directions. More particularly, moving from a distal position to a proximal position within the needle assembly 200 corresponds to the direction of flow from the needle 202 to the fluid conducting element 20. On the other hand, moving from a distal position to a proximal position within the needle receiving assembly 100 corresponds to the opposite direction of flow from the needle 202 to the fluid conducting element 20. Although illustrated only in FIG. 1a, these definitions of the terms proximal and distal are valid also for the other figures and the rest of the specification.

In yet other words, a first element or portion or section of the needle assembly 200 is more proximal (less distal) than a second element or portion or section of the needle assembly 200 if the first element or portion or section of the needle assembly 200 is downstream of the second element or portion or section of the needle assembly 200. On the other hand, a first element or portion or section of the needle receiving assembly 100 is more distal (less proximal) than a second element or portion or section of the needle receiving assembly 100 if the first element or portion or section of the needle receiving assembly 100 is downstream of the second element or portion or section of the needle receiving assembly 100. Herein downstream refers to the direction in which the sample can be introduced or flow from the needle 202 to the fluid conducting element 20. The downstream direction is illustrated by arrow A5 in FIG. 1a. Opposite to the downstream direction is the upstream direction illustrated by arrow A4 in FIG. 1a. Although illustrated only in FIG. 1a, these definitions of the terms downstream and upstream are valid also for the other figures and the rest of the specification.

Furthermore, throughout the specification the term diameter of a surface, as in, diameter of an aligning inner surface, diameter of an aligning outer surface, diameter of an inner surface, diameter of an outer surface is used. Unless otherwise specified, the term diameter of a surface refers to the diameter of the cross-sections of the surface, said cross-sections being perpendicular to the axial direction. For example, the sentence "the diameter of a surface tapers along the axial direction" is to be understood as the diameters of cross-section perpendicular to the axial direction of the surface tapers along the axial direction. The same is true, unless otherwise specified, when referring to a diameter of an element, e.g. a diameter of the needle, a diameter of the needle housing, a diameter of the fluid conducting element housing, a diameter of the cavity, a diameter of the fluid conducting element and the like.

The needle assembly 200 can comprise the needle 202 mounted in a needle housing 2040. The needle housing 2040 can also be referred to as a needle holder 2040 or centering piece 2040. The needle 202 can comprise a metallic, quartz glass or fused silica material. The needle housing 2040 can comprise a metallic or polymetric material (e.g. PEEK). As will be discussed further below, the needle housing 2040 can have the following advantages: It can facilitate aligning the needle 202 with the fluid conducting element 20 (more particularly with a needle seat 1070 of the needle receiving assembly 100) during the connection between the two. In addition, the needle housing 2040 can provide protection to the needle 202 and/or to an operator (e.g. during needle change).

Typically, the needle 202 can be unreleasably mounted or attached or connected to the needle housing 2040. For example, both the needle 202 and the needle housing 2040 can comprise a metallic material and the needle 202 can be welded to the needle housing 2040, hence rendering an unreleasable connection between the two. Alternatively, the needle 202 (e.g. made of quartz glass or fused silica) can be pressed into the needle housing 2040 (e.g. made of PEEK), hence rendering an unreleasable connection between the two.

The needle housing 2040 can comprise a width along the radial direction in the range of 2 mm to 50 mm, preferably 4 mm to 20 mm, more preferably 5 mm to 10 mm, such as 7.5 mm. More particularly, the width of the needle housing 2040 in the radial direction can be between 2 times to 100 times, preferably 5 times to 20 times, more preferably 8 times to 12 times the outer diameter of the needle 202. Moreover, the needle housing 2040 can comprise a length along the axial direction in the range of 1 mm to 50 mm, preferably 2 mm to 10 mm.

In some embodiments, the needle housing 2040 can extend proximally beyond the tip of the needle 202. The length along the axial direction of the extension of the needle housing 2040 proximally beyond the tip of the needle 202 can be in the range of 0.1 mm to 2 mm, preferably 0.2 mm to 1 mm, such as 0.25 mm. That is, the needle housing 2040 can protrude proximally beyond the tip of needle 202 and the protrusion can comprise a length of 0.1 mm to 2 mm, preferably 0.2 mm to 1 mm, such as 0.25 mm.

The needle housing 2040 can comprise a needle housing cavity 2050, which for the sake of brevity can also be referred to as a cavity 2050. The needle housing cavity 2050 can be occupied in part by the needle 202. More particularly, a needle holding portion of the needle housing cavity 2050 can comprise a diameter corresponding to the outer diameter of the needle 202 such that the needle holding portion of the needle housing cavity 2050 can tightly or snuggly fit the needle 202. The needle 202 can be welded to the needle housing 2040 on the walls of the needle holding portion of the needle housing cavity 2050.

In some embodiments, the needle housing cavity 2050 can further comprise a wider portion of the needle housing cavity 2050 which can be in part occupied by the needle 202. The wider portion of the needle housing cavity 2050 can be configured to fit a portion of the needle receiving assembly 100. In some embodiments, the difference between the diameter of the wider portion of the needle housing cavity 2050 and the diameter of the portion of the needle receiving assembly 100 received in the wider portion of the needle housing cavity 2050 can be between 0.02 mm to 0.04 mm. Moreover, the wider portion of the needle housing cavity 2050 can comprise a length along the axial direction which can be larger than the length along the axial direction of the portion of the needle receiving assembly 100 received in the wider portion of the needle housing cavity 2050. Thus, a force with which the needle assembly 200 is pressed onto the needle receiving assembly 100 is mostly exerted onto the needle 202 which is pressed into a needle seat 1070. This can facilitate creating a tight connection between the needle assembly 200 and the needle receiving assembly 100. Again, this can be advantageous for withstanding the high pressures generally present in chromatography systems, such as high-performance liquid chromatography systems or ultra-high-performance liquid chromatography systems.

The wider portion of the needle housing cavity 2050 can be provided more proximal than the needle holding portion of the needle housing cavity 2050.

In the most proximal section, the needle 202 can comprise a needle tip, which can typically comprise a smaller outer diameter compared to the rest of the needle 202. That is, the needle 202 may comprise a proximal portion with an outer diameter tapering along the axial direction towards the needle tip. The outer diameter of the needle 202 can be in the range of 0.1 mm to 2 mm, preferably 0.3 mm to 1.8 mm, more preferably between 0.5 mm to 1.6 mm. Further, the needle may comprise a constant inner diameter which can be in the range of 5 µm to 500 µm, preferably 30 µm to 400 µm, more preferably 50 µm to 300 µm. That is, the needle 202 can comprise a bore with a constant diameter. The bore can allow a fluid to flow through the needle 202. Moreover, the needle tip can be open such that the fluid can flow out of the needle 202.

As discussed, the needle receiving assembly 100 can comprise a fluid conducting element 20. The fluid conducting element 20 may typically comprise a hollow cylindrical shape, similar to a tube. That is, the fluid conducting element 20 can typically comprise a constant outer diameter and a constant inner diameter. In other words, the fluid conducting element 20 can comprise a bore which can allow a fluid to flow through the fluid conducting element 20. In some embodiments, the fluid conducting element 20 can be a capillary 20. In such embodiments, the bore of the fluid conducting element 20 can be free, thus, allowing a fluid to flow uninterrupted through the fluid conducting element 20 (i.e. capillary 20). Alternatively, the fluid conducting element 20 can be a chromatographic column 20. In such embodiments, the bore of the fluid conducting element 20 can be packed with a stationary phase, thus, facilitating the separation of a chemical compound.

The fluid conducting element 20 can comprise an inner tube which surrounds the bore of the fluid conducting element 20. The inner tube of the fluid conducting element 20 can be made of different materials. In some embodiments, the inner tube of the fluid conducting element 20 can be made of fused silica and can be referred to as a fused silica inner tube of the fluid conducting element 20. The fused silica inner tube of the capillary 20 can comprise an inner diameter (i.e. a diameter of the bore of the capillary 20) which can be in the range of 1 µm to 300 µm, preferably 5 µm to 200 µm, more preferably 10 µm to 150 µm. Further, the fused silica inner tube of the capillary 20 can comprise an outer diameter in the range of 150 µm to 600 µm, preferably 200 µm to 500 µm, more preferably 280 µm to 450 µm. These dimensions are particularly suitable when the fluid conducting element 20 is realized as a capillary. On the other hand, the fused silica inner tube of the chromatographic column 20 can comprise an inner diameter (i.e. a diameter of the bore of the chromatographic column 20) which can be in the range of 5 µm to 10 mm, preferably 50 µm to 1 mm.

In some embodiments, the inner tube of the fluid conducting element 20 can be made of a metallic or plastic material and can be referred to as a metallic or plastic inner tube of the fluid conducting element 20. The metallic or plastic inner tube of the capillary 20 can comprise an inner diameter (i.e. a diameter of the bore of the capillary 20) which can be in the range of 150 µm to 700 µm, preferably 250 µm to 600 µm, more preferably 350 µm to 500 µm. Further, the metallic or plastic inner tube of the capillary 20 can comprise an outer diameter in the range of 0.3 mm to 1.5 mm, preferably 0.6 mm to 1 mm, more preferably 0.75 mm to 0.85 mm, such as 0.79 mm. These dimensions are particularly suitable in case the fluid conducting element is realized as a capillary. Again, in embodiments wherein the fluid conducting element 20 is a chromatographic column, the metallic or plastic inner tube can comprise an inner diameter (i.e. a diameter of the bore of the chromatographic column 20) which can be larger, e.g., up to 10 mm.

In addition, the fluid conducting element 20 can comprise a sheathing outer layer, snuggly surrounding the inner tube of the fluid conducting element 20. The sheathing outer layer of the fluid conducting element 20 can comprise a polymetric material, such as poly-ether-ether-ketone (PEEK), poly-ether-ketone (PEK), poly-ether-ether-ether-ketone (PEEEK) and a polyphenylene sulfide (PPS). The sheathing outer layer of the fluid conducting element 20 can comprise a thickness in the range of 50 µm to 500 µm, preferably 100 µm to 300 µm, such as 180 µm to 200 µm.

Further, the needle receiving assembly 100 can comprise a needle seat 1070. The needle seat 1070 can be provided in the needle receiving assembly 100 more proximal than the fluid conducting element 20 and preferably arranged concentric to the fluid conducting element 20. The needle seat 1070 can be configured to receive a continuous longitudinal portion of the needle 202 starting at the tip of the needle 202. That is, the needle seat 1070 can comprise a cavity formed in the needle receiving assembly 100 which can be configured to receive a longitudinal portion of the needle 202 starting at the tip of the needle 202. In some embodiments, the needle seat 1070 is formed by a sealing element 10.

The needle receiving assembly 100 can further comprise a fluid conducting element housing 40, which for the sake of brevity can be referred to as a housing 40. The fluid conducting element housing 40 can accommodate a longitudinal portion of the fluid conducting element 20 which is more proximal than the rest of the fluid conducting element 20. That is, the fluid conducting element housing 40 can comprise a cavity which can be occupied in part by the fluid conducting element 20. The fluid conducting element housing 40 and the fluid conducting element 20 can be held together in an unreleasable manner. That is, the fluid conducting element 20 cannot slide out of the fluid conducting element housing 40.

The needle assembly 200 and/or the needle receiving assembly 100 can be configured to facilitate alignment in the radial direction between the needle 202 and the needle receiving assembly 100. That is, the needle assembly 200 and/or the needle receiving assembly 100 can be configured to arrange concentrically the needle 202 with the needle receiving assembly 100 and more particularly with the needle seat 1070 of the needle receiving assembly 100. More particularly, the needle assembly 200 and/or the needle receiving assembly 100 can comprise geometrical features which can guide the needle assembly 200 and/or the needle receiving assembly 100 into alignment during the connection between the two. It will be noted that the alignment between the needle assembly 200 and/or the needle receiving assembly 100 is performed passively, i.e., by means of the shape or construction of the needle assembly 200 and/or needle receiving assembly 100.

A maximum tolerable deviation between the central axis of the needle 202 and the central axis of the needle seat 1070 can be up to 1 mm. The needle assembly 200 and/or needle receiving assembly 100 can be configured to align the needle 202 with the needle seat 1070 if the deviation between the central axis of the needle 202 and the central axis of the needle seat 1070 is within the maximum tolerable deviation (also referred to as tolerance). As will be understood, the maximum tolerable deviation can be made larger, however this may result in a bulkier needle assembly 200 and/or needle receiving assembly 100. In other words, there can be a trade-off between maintaining the size of the needle assembly 200 and/or needle receiving assembly 100 within limits that can be advantageous, ergonomic, practical or usable in a chromatography system and increasing the maximum tolerable deviation.

In the following and with reference to respective figures, different aligning components of the needle assembly 200 and needle receiving assembly 100 will be discussed.

FIGS. 1a to 1d illustrate a needle assembly 200 comprising an aligning inner surface 2044B. More particularly, the needle assembly 200 can comprise a needle 202 mounted on a needle housing 2040, as discussed. The needle housing 2040 can comprise a cavity 2050 laterally enclosed by an inner surface of the needle housing 2040. On said inner surface, an aligning inner surface 2044B can be provided. That is, a portion of the inner surface of the needle housing 2044B that laterally encloses the needle housing cavity 2050 can be configured as an aligning inner surface 2044B. More particularly, the aligning inner surface 2044B can be formed by at least a portion of the inner surface that laterally encloses the needle housing cavity 2050.

Figure 1A:
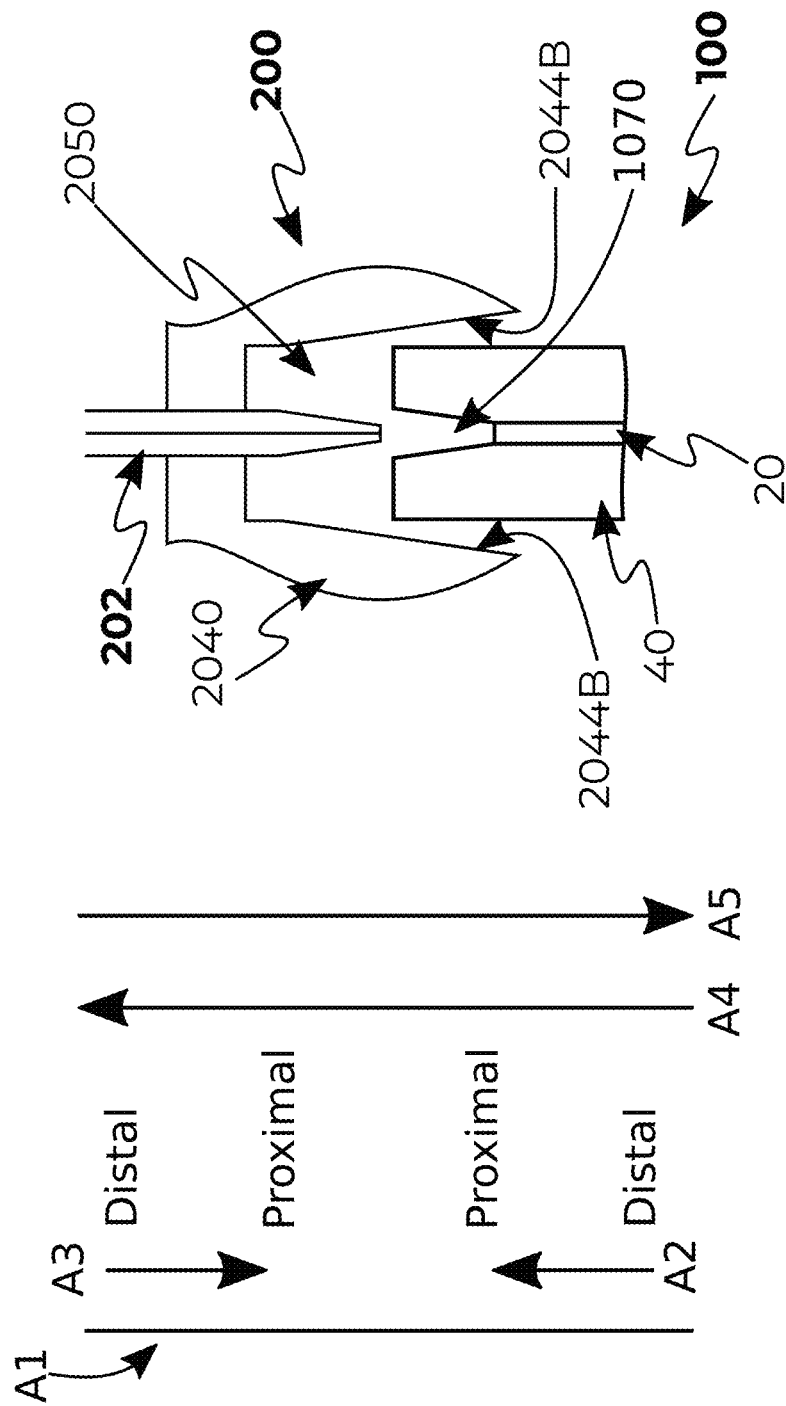
FIGS. 1a to 1d depict longitudinal sections of a needle assembly and a needle receiving assembly according to embodiments of the present invention wherein the needle assembly comprises an aligning inner surface.

As illustrated in FIG. 1a, an inner diameter of the needle housing cavity 2050 can increase along the downstream direction, hence forming the aligning inner surface 2044B. The shape of the aligning inner surface 2044B can be similar to the shape of the lateral surface of a conical frustum with its base being more proximal than the rest of the conical frustum. In other words, the diameter of the aligning inner surface 2044B can taper along the axial direction when moving from a more proximal position to a more distal position within the needle assembly 200. That is, the diameter of the aligning inner surface 2044B (i.e. diameter of the cavity 2050) can taper along an opposite direction to the downstream direction.

The inner surface of the needle housing 2040 can comprise a section with a constant diameter, said section with the constant diameter being more distal than the aligning inner surface 2044B. The shape of the section with the constant diameter can be similar to the shape of the lateral surface of a cylinder. Moreover, the diameter of the said section can be larger or equal to the minimum diameter of the aligning inner surface 2044B. The provision of the section with a constant diameter being no smaller than the minimum diameter of the aligning inner surface can be advantageous, as it can provide "space" between the needle assembly 200 and the needle receiving assembly 100 when they are connected. This, as discussed above, can facilitate reducing a force parallel to the axial direction and pushing the needle receiving assembly 100 and the needle assembly 200 away from each other.

The aligning inner surface 2044B of the embodiment illustrated in FIG. 1a can be defined or described by a taper angle and the length of the aligning inner surface along 2044B the axial direction. The taper angle of the aligning inner surface 2044B can define the taper rate, i.e., the rate at which the diameter of the aligning inner surface 2044B tapers along the axial direction when moving from a proximal position to a distal position within the needle assembly 200.

The taper angle of the aligning inner surface 2044B can depend on the geometry of the needle receiving assembly 100 and needle assembly 200. This is illustrated in FIGS. 1b and 1c.

Figure 1D:
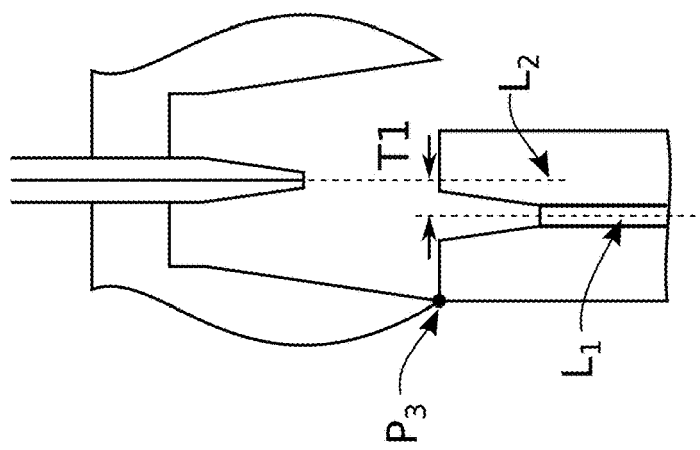
Figure 1C:
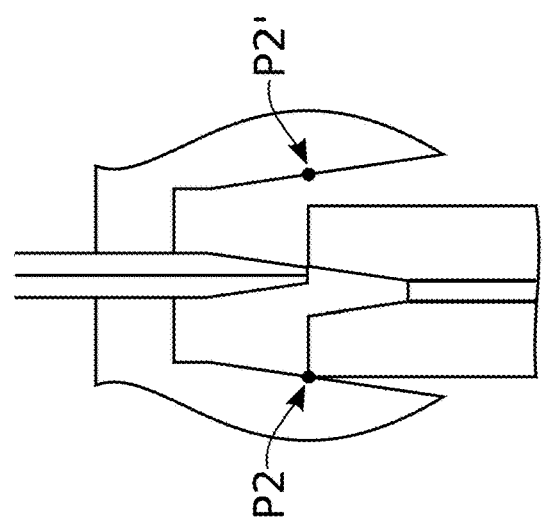
Figure 1B:
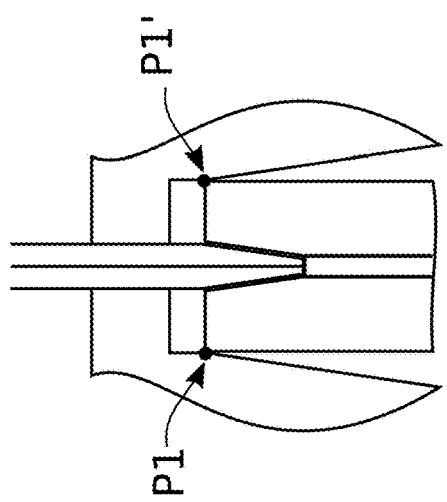

FIG. 1b illustrates the needle assembly 200 and the needle receiving assembly 100 fully connected and aligned with each other. At this position, a distal diameter of the aligning inner surface 2044B can be obtained. More particularly, the needle receiving assembly 100 and the needle assembly 200 can (almost) contact each other at points P1 and P1'. For sake of completeness, it will be understood that FIG. 1b is a longitudinal cross-sectional view of components that are generally rotational-symmetric. Further, it should also be understood that the Figures (unless indicated otherwise) are central longitudinal cross-sectional views, i.e., longitudinal cross sections including the central axis. Thus, the "points" P1 and P1' are points on a circular line, and it should be understood that when these points are discussed in this specification, the points in the longitudinal cross-sectional view are meant. Further, the "points" P1 and P1' and the corresponding circular line including these points are defined as the section on the aligning inner surface 2044B being located at the same height in the axial direction as the most proximal section of the needle receiving assembly 100 when the needle assembly 200 is fully inserted in the needle receiving assembly 100. The distal diameter of the aligning inner surface 2044B can be obtained by the distance between points P1 and P1'. Points P1 and P1' can be joined by a straight line passing through a center of a cross section of the aligning inner surface 2044B, which cross section comprises points P1 and P1' and is perpendicular to the axial direction. The distal diameter of the aligning inner surface 2044B can correspond to the diameter of the most proximal surface of the needle receiving assembly 100 or can be slightly larger than the most proximal diameter of the needle receiving assembly 100. As will be understood, if the distal diameter would be significantly larger than the distance between points P1 and P1' a proper alignment between the needle 202 and the needle receiving assembly 100 cannot be guaranteed. On the other hand, if the distal diameter is smaller than the distance between points P1 and P1', the needle receiving assembly 100 would not fit so that the needle 202 can be properly received in the needle seat 1070. Preferably, the distal diameter of the aligning inner surface 2044B (i.e. distance between points P1 and P1'), which corresponds to the minimum diameter of the aligning inner surface 2044B, can be slightly greater (e.g. 0.01 mm-0.02 mm greater) than the diameter of the most proximal surface of the needle receiving assembly 100. This would allow the needle receiving assembly 100 to be received in the cavity 2050 of the needle assembly 200 distally beyond points P1 and P1' (further facilitated by the "space" provided between the needle assembly 200 and the needle receiving assembly 100, as discussed above). This can be particularly advantageous to realize a tight connection between the needle 202 and the needle seat 1070. Put differently, in such a realization (where the distal diameter P1-P1' of the needle assembly 200 is slightly greater than the proximal diameter of the needle receiving assembly 100), an axial force used to press the needle assembly 200 and the needle receiving assembly 100 together will primarily act on the needle 202 and the needle seat 1070, i.e., the force is used to seal the needle 202 and the needle seat 1070 to one another.

As depicted in FIG. 1b, the cavity 2050 extends distally beyond the cross section comprising points P1 and P1'. Again, this can be advantageous as it may allow space for the needle receiving assembly 100 to be further received in the cavity 2050 of the needle assembly 200. As a result, the force at which the needle 202 can press against the needle seat 1070 can be increased—which can make the connection tighter and non-leaking. To further facilitate this, the diameter of the cavity 2050 may not taper in the portion that is distally beyond the cross section comprising points P1 and P1'. That is, all the cross sections of the cavity 2050 distally beyond the cross section comprising points P1 and P1' can comprise a diameter not smaller than the distance between points P1 and P1'. In such embodiments, the aligning inner surface 2044B can be considered to extend distally up to the cross section comprising points P1 and P1'. This is also illustrated in FIGS. 1a to 1b, wherein the diameter of needle housing cavity 2050 decreases distally up to points P1 and P1', wherein the diameter of the needle housing cavity 2050 is at minimum.

FIG. 1c illustrates the needle assembly 200 and the needle receiving assembly 100 in a position wherein the needle 202 is about to enter the needle seat 1070 (it will be understood that in some embodiments, there may also be a housing portion in the needle receiving assembly 100 extending further proximally than the needle seat 1070—in such embodiments, FIG. 1c may correspond to the needle 202 being about to enter this housing portion). At this position, a proximal diameter of the aligning inner surface 2044B can be similarly obtained based on a distance between points P2 and P2'.

Using the distal and the proximal diameter of the aligning inner surface 2044B the taper angle of the aligning inner surface 2044B can be determined.

FIG. 1d illustrates the position wherein the needle receiving assembly 100 is about to be received on the needle housing cavity 2050. This position indicates the maximum misalignment that can be corrected by the aligning inner surface 2044B. The maximum misalignment (i.e. tolerance) is illustrated by the distance T1 between the longitudinal central axis of the needle 202 (illustrated by the dashed line L2) and the longitudinal central axis of the needle seat 1070 (illustrated by the dashed line L1). If the distance between the longitudinal central axis of the needle 202 and the longitudinal central axis of the needle seat 1070 is equal to or smaller than T1 the aligning inner surface 2044B can "capture" the needle receiving assembly 100 and guide it into proper alignment as illustrated in FIG. 1b.

The tolerance of the aligning inner surface 2044B can be adjusted based on the distance along the axial direction between the point P3 and the needle tip. The more the aligning inner surface 2044B protrudes proximally beyond the needle tip (i.e. the larger the distance along the axial direction between the point P3 and the needle tip), the larger the tolerance of the aligning inner surface 2044B can be. Based on this rationale, the needle housing 2040, more particularly the aligning inner surface 2044B, can be configured for tolerating different amounts of misalignment between the needle 202 and the needle seat 1070.

In FIGS. 1a to 1d, the aligning inner surface 2044B is comprised by the needle assembly 200. Alternatively or additionally, an aligning inner surface can be comprised by the needle receiving assembly 100. This is illustrated in FIG. 1e.

Figure 1E:
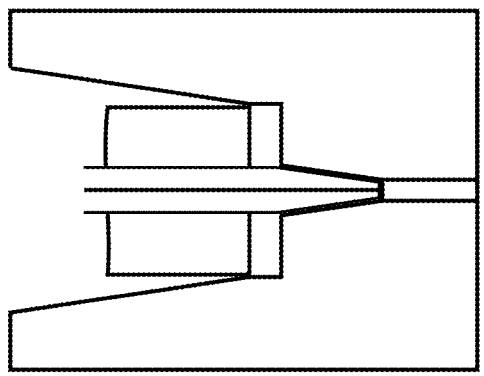
FIG. 1e depicts a longitudinal section of a needle assembly and a needle receiving assembly according to embodiments of the present invention wherein the needle receiving assembly comprises an aligning inner surface.
Figure 1E:
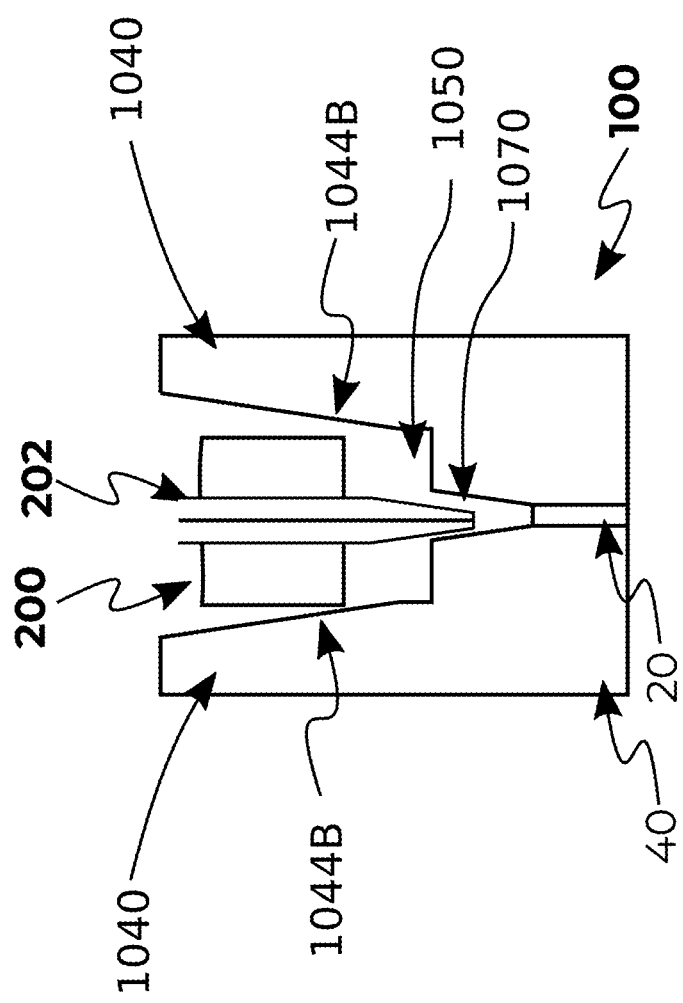

FIG. 1e illustrates a needle receiving assembly 100 comprising an aligning inner surface 1044B. FIG. 1e depicts the needle receiving assembly 100 comprising an aligning inner surface 1044B in two different positions relative to a needle assembly 200, wherein in one of the positions the needle assembly 200 and the needle receiving assembly 100 are connected and aligned with each other. In this configuration (FIG. 1e, right), the needle assembly 200 is fully inserted in the needle receiving assembly 100. As illustrated, the fluid conducting element housing 40 of the needle receiving assembly 100 can be provided with a lateral protruding portion 1040 that protrudes proximally beyond the needle seat 1070. The lateral protruding portion 1040 can form a needle receiving assembly cavity 1050 which can be occupied in part by the needle assembly 200.

In the embodiment depicted in FIG. 1e, the entire needle receiving assembly cavity 1050 is provided more proximal than the needle seat 1070. As such, to allow a portion of the needle 202 to be received in the needle seat 1070, the said portion of the needle 202 can protrude proximally beyond the needle housing 2040. Thus, the needle housing 2040 can be received in the needle receiving assembly cavity 1050 and a portion of the needle 202 protruding proximally beyond the needle housing 2040 can be received in the needle seat 1070.

As will be understood, the aligning inner surface 1044B of the needle receiving assembly 100 can be obtained by "flipping" the aligning inner surface 2044B of the needle assembly 200. That is, the taper angle and tolerance of the aligning inner surface 1044B of the needle receiving assembly 100 can be similar to the taper angle and tolerance of the aligning inner surface 2044B of the needle assembly 200 discussed above and with respect to FIGS. 1a to 1d. For the sake of brevity, a detailed illustration and discussion, as performed for the aligning inner surface 2044B of the needle assembly 200, is omitted for the aligning inner surface 1044B of the needle receiving assembly 100.

In FIGS. 1a to 1d, the aligning inner surface 2044B comprises a constant taper angle. That is, the aligning outer surface 2044 comprises a diameter that tapers at a constant rate. However, it will be understood that the diameter of the aligning inner surface 2044 may also taper at different rates.

FIGS. 2a to 2d illustrate an embodiment of a needle assembly 200 comprising an aligning inner surface 2044B, which diameter can taper with two different rates along the axial direction. More particularly, the aligning inner surface 2044B can comprise a proximal aligning inner surface 3001 and a distal aligning inner surface 3002. The proximal aligning inner surface 3001 is more proximal than the distal aligning inner surface 3002. Moreover, the proximal and distal aligning inner surfaces 3001, 3002 can comprise only one cross sectional extension perpendicular to the axial direction in common. Said common cross-section can comprise a diameter that can corresponds to a minimum diameter of the proximal aligning inner surface 3001 and to a maximum diameter of the distal aligning inner surface 3002.

Figure 2A:
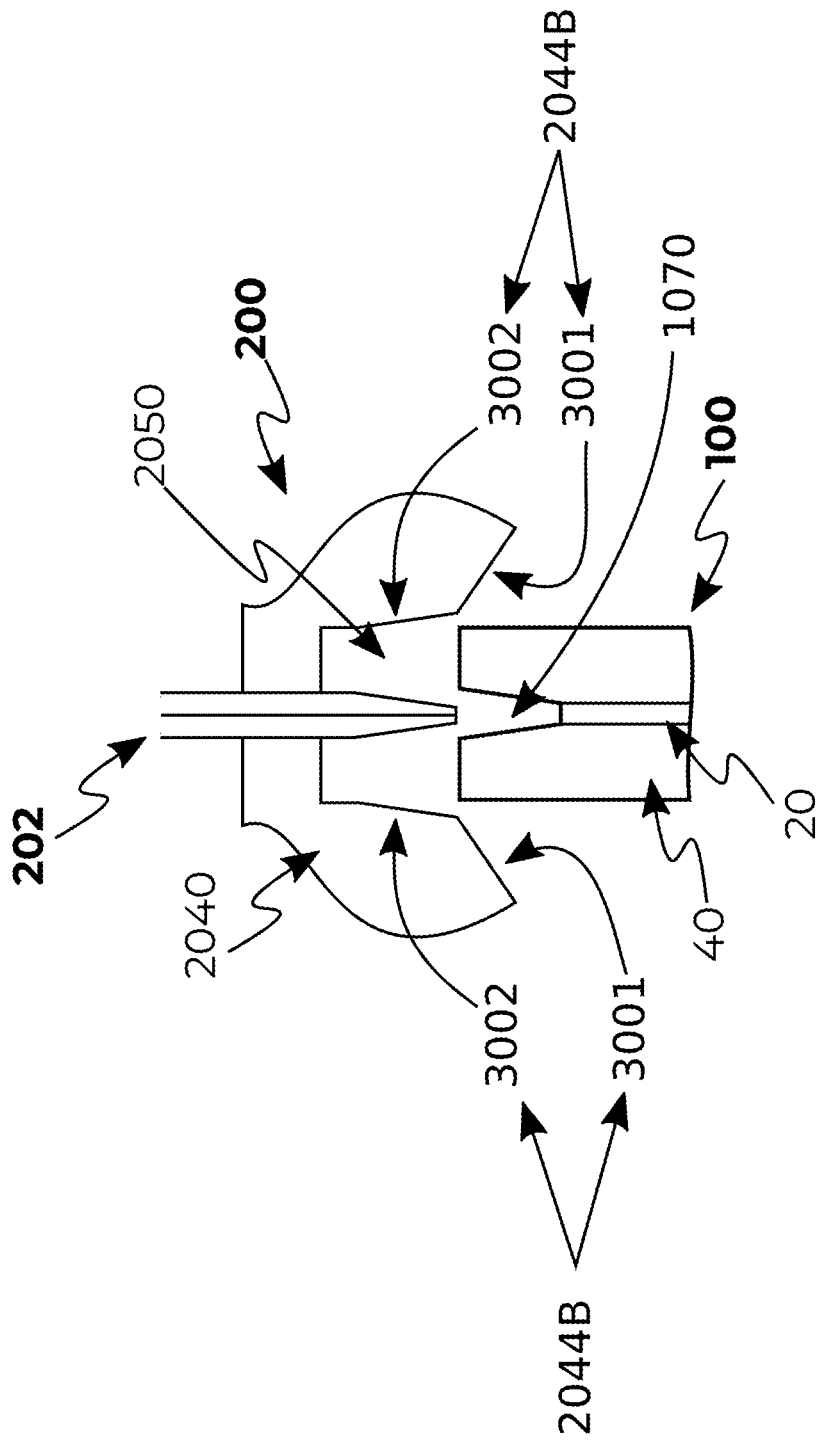
FIGS. 2a to 2d depict longitudinal sections of a needle assembly and a needle receiving assembly according to embodiments of the present invention wherein the needle assembly comprises an aligning inner surface.

The diameters of the proximal and the distal aligning inner surfaces 3001, 3002 can taper along the axial direction when moving from a proximal position to a distal position (i.e. opposite to the downstream direction) with different rates. As illustrated in FIG. 2a, the diameter of the proximal aligning inner surface 3001 can taper at a higher rate (i.e. faster) compared to the diameter of the distal aligning inner surface 3002. In other words, the taper angle of the proximal aligning inner surface 3001 can be larger than the taper angle of the distal aligning inner surface 3002.

Figure 2D:
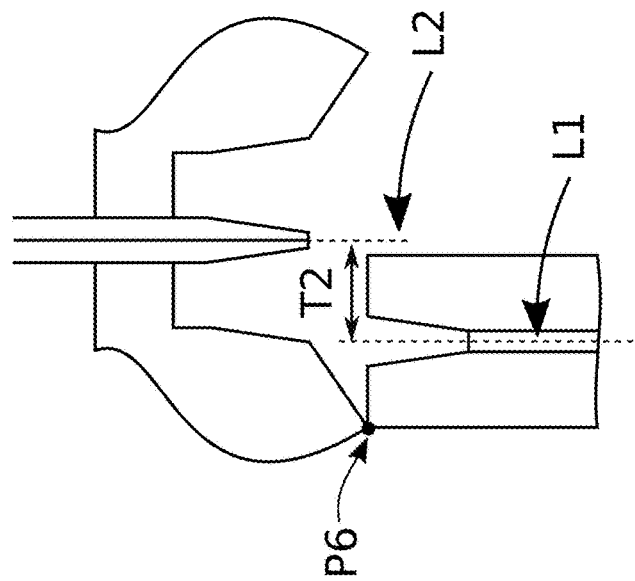
Figure 2C:
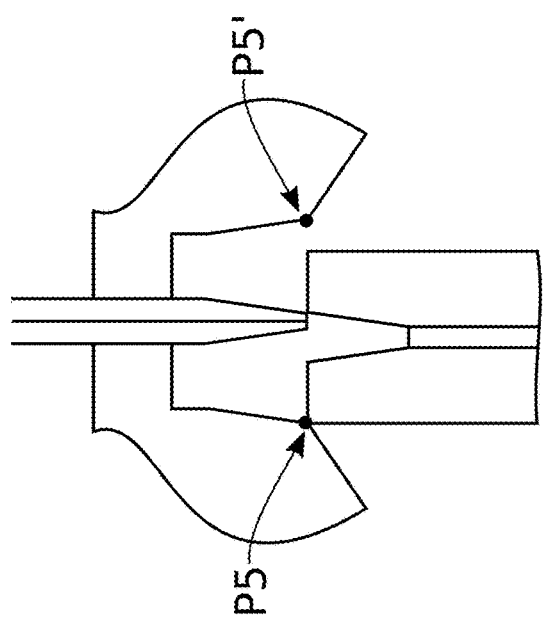
Figure 2B:
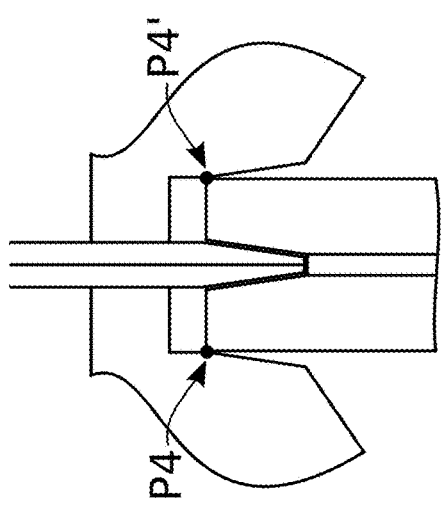

The taper angle of the distal aligning inner surface 3002 can be determined based on the distance between points P4 and P4' and the distance between points P5 and P5', as illustrated in FIGS. 2b and 2c, in a similar manner as discussed for the aligning inner surface 2044B in FIGS. 1b and 1c.

As illustrated in FIGS. 2a to 2d and similar to the embodiment discussed with reference to FIGS. 1a to 1d, the needle housing cavity 2050 can extend distally beyond points P4 and P4'. Moreover, the diameter of the needle housing cavity 2050 distally beyond points P4 and P4' can be no smaller than the distance between points P4 and P4'. As such, the needle housing cavity 2050 can provide a space beyond points P4 and P4', which can be occupied by the needle receiving assembly 100. This can be particularly advantageous, as it can allow the needle 202 to be tightly pressed against the needle seat 1070.

FIG. 2d illustrates the maximum misalignment (i.e. tolerance) that can be corrected by the aligning inner surface 2044B. It is illustrated by distance T2 measured as the distance between the longitudinal central axis of the needle 202 (illustrated by the dashed line L2) and the longitudinal central axis of the needle seat 1070 (illustrated by the dashed line L1). The tolerance T2 of the aligning inner surface 2044B can depend on the taper angle of the proximal aligning inner surface 3001. More particularly, the larger the taper angle of the distal aligning inner surface 3001, the larger the distance along the radial axis between point P6 and the central axis L2 of the needle 202. As a result, the larger the tolerance T2.

In other words, the proximal aligning inner surface 3001 can "capture" the needle receiving assembly 100 (as shown in FIG. 2d) and guide it until the needle tip is about to enter the needle seat 1070 (as shown in FIG. 2c). Then, the distal aligning inner surface 3002 can further guide the needle receiving assembly 100 such that a portion of the needle 202 is properly received in the needle seat 1070 (as shown in FIG. 2b).

This arrangement can be advantageous over the one illustrated in FIGS. 1a to 1d for the following reasons: As an initial matter, "capturing" the needle receiving assembly 100 and guiding the needle 202 as it enters in the needle seat 1070 are performed by the proximal aligning inner surface 3001 and distal aligning inner surface 3002, respectively. Thus, the proximal aligning inner surface 3001 and the distal aligning inner surface 3002 can be configured or optimized independently which may result in a more efficient configuration of the aligning inner surface 2044B. Furthermore, the tolerance of the aligning inner surface can be increased not only by extending the aligning inner surface 2044B proximally beyond the needle tip but also by increasing the taper angle of the proximal aligning inner surface 3001. In other words, there are 4 degrees of freedom (DoF) for adjusting the trade-off between bulkiness of the needle assembly 200 and the tolerance of the aligning inner surface 2044: 2 DoF along the axial direction (i.e. increasing/decreasing the length along the axial direction of the proximal aligning inner surface 3001) and 2 DoF along the radial direction (i.e. increasing/decreasing the maximum diameter of the proximal aligning inner surface 3001). Put simply, there are 4 DoF to adjust the position of point P6 while keeping P5, P5' and P4, P4' fixed. Thus, tolerance of the aligning inner surface 2044B can be adjusted independently of the portion of the aligning inner surface 2044B that guides the insertion of the needle tip on the needle seat 1070.

Figure 2E:
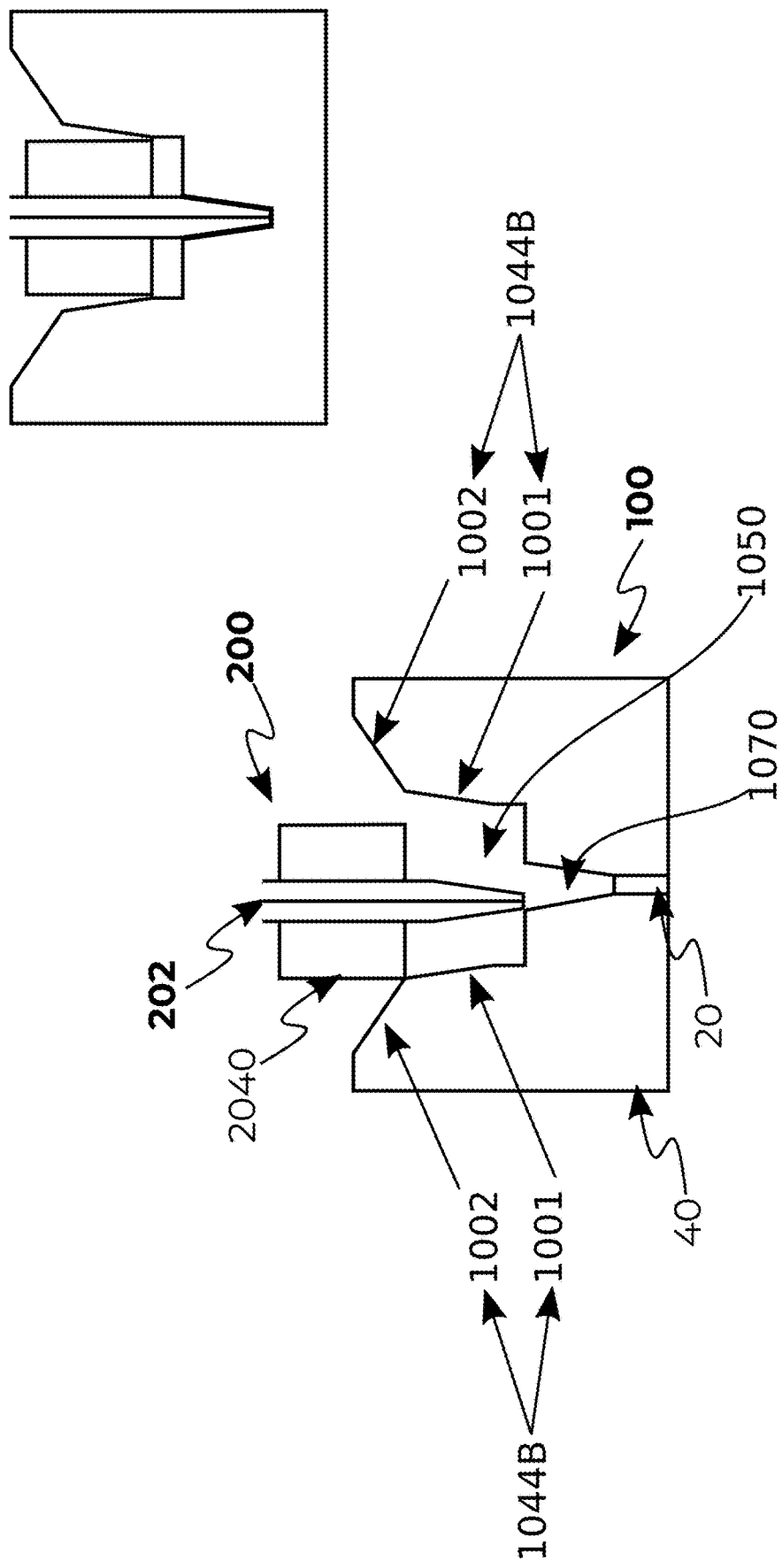
FIG. 2e depicts a longitudinal section of a needle assembly and a needle receiving assembly according to embodiments of the present invention wherein the needle receiving assembly comprises an aligning inner surface.

Similarly, the aligning inner surface with multiple taper angles can be provided on the needle receiving assembly 100. As illustrated in FIG. 2e, the needle receiving assembly 100 can comprise an aligning inner surface 10448 comprising a distal aligning inner surface 1001 and a proximal aligning inner surface 1002. The aligning inner surface 1044B of the needle receiving assembly 100 can be configured similar to the aligning inner surface 2044B of the needle assembly 200. More particularly, the distal aligning inner surface 1001 can comprise corresponding features of the distal aligning inner surface 3001 and the proximal aligning inner surface 3002 can comprise corresponding features of the proximal aligning inner surface 3002.

Figure 3A:
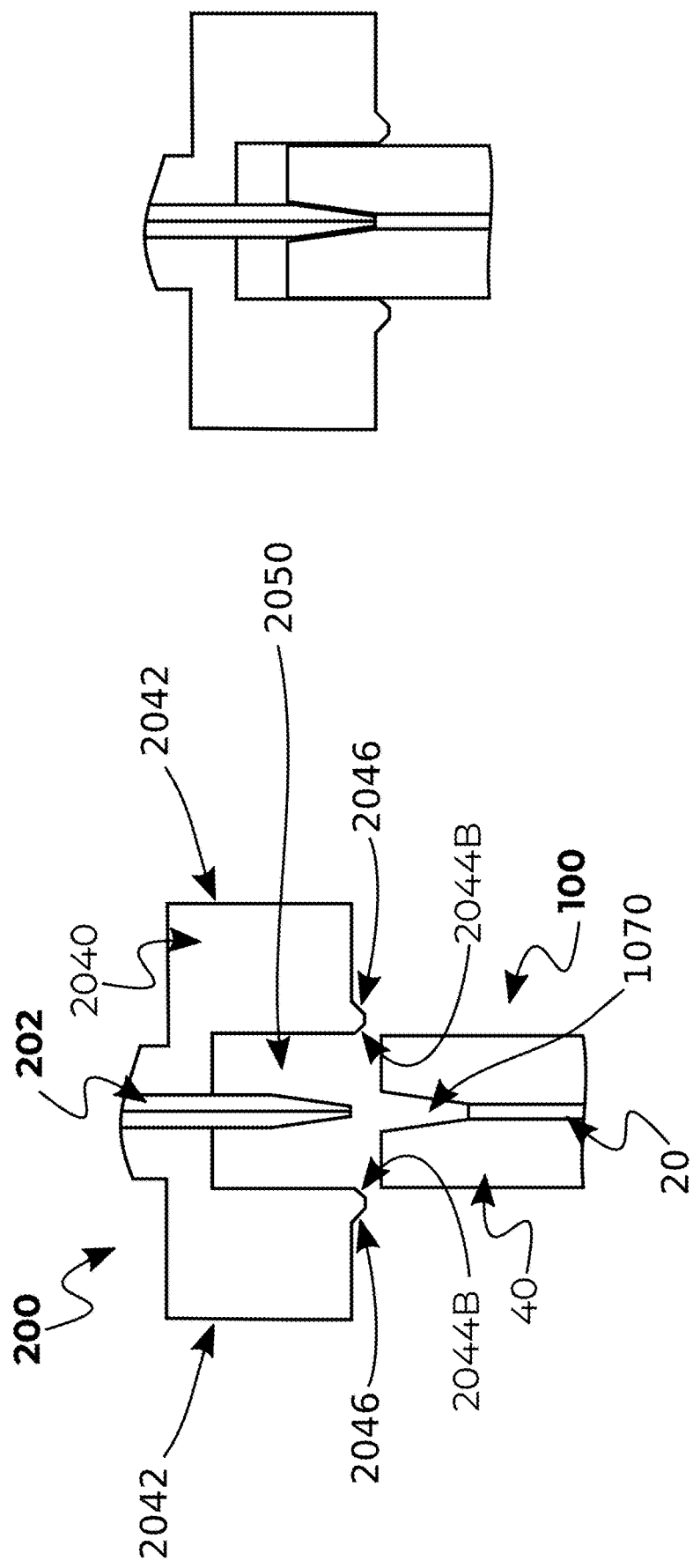
FIG. 3a depicts a longitudinal section of a needle assembly and a needle receiving assembly according to embodiments of the present invention wherein the needle assembly comprises an aligning inner surface.

FIG. 3a illustrates a preferred embodiment of the needle assembly 200. In this embodiment, the needle housing 2040 can comprise a distal portion 2042 comprising a constant outer diameter. The distal portion 2042 can further comprise an inner diameter. That is, the needle housing 2040 can comprise a hollow shape with a cavity 2050 inside. The cavity 2050 can extend in the axial direction along the entire length of the needle housing 2040, including the distal section 2042.

The cavity 2050 can comprise different diameters. In a most distal section, which can also be referred to as the needle holding portion of the cavity 2050, the cavity 2050 can comprise a diameter matching the outer diameter of the needle 202. Directly downstream the needle holding portion of the cavity 2050, the cavity 2050 can comprise a wider portion with a larger diameter. The diameter of the wider portion of the cavity 2050 can correspond to (e.g. be slightly greater than) the outer diameter of a portion of the fluid conducting element housing 40 that can be received in the cavity 2050 of the needle housing 2040. The portion of the fluid conducting element housing 40 that can be received in the cavity 2050 of the needle housing 2040 can also be referred to as a central protruding portion 1060, e.g., see FIG. 7a.

In addition, the needle housing 2040 can comprise a proximal portion 2046. The proximal portion 2046 can protrude (i.e. extend) proximally beyond the tip of the needle 202. In such embodiments, the proximal portion 2046 can also be referred to as a protrusion 2046. The proximal portion 2046 can protrude along the axial direction at least 0.1 mm, preferably at least 0.2 mm, and at most 2 mm, preferably at most 1 mm, such as 0.25 mm.

The proximal portion 2046 can comprise an inner diameter. That is, the cavity 2050 can extend up to and including the proximal portion 2046. The inner diameter of the proximal portion 2046 can taper along the axial direction when moving from a proximal position to a distal position (i.e. opposite to the downstream direction). As such, an inner surface of the proximal portion 2046 that laterally encloses a portion of the cavity 2050 can form the aligning inner surface 2044B of the needle assembly 200.

In some embodiments, the aligning inner surface 2044B can extend along at least 30%, preferably at least 60%, more preferably at least 80% of the length along the axial direction of the proximal portion 2046. This is illustrated in FIG. 3a.

Alternatively, the aligning inner surface 2044B can extend distally beyond the proximal portion 2046 of the needle housing 2040. Thus, the diameter of the entire inner surface of the proximal portion 2046 and the inner diameter of a more distal portion of the inner surface can taper along the axial direction to form the aligning inner surface 2044B.

Alternatively still, the aligning inner surface 2044B may be provided entirely on the inner surface of a more distal portion 2042. In such embodiments, the diameter of a portion of the inner surface of the distal portion 2040 can taper along the axial direction opposite to the downstream direction to form the aligning inner surface 2044B. On the other hand, the inner diameter of the proximal portion 2046 can be constant and not smaller than the maximum diameter of the aligning inner surface 2044B. In other words, in some embodiments, the aligning inner surface 2044B can be provided less proximal than the proximal section 2046 and the inner diameter of the proximal section 2046 can be no smaller than the diameter of the aligning inner surface 2046. This can allow the fluid conducting element housing 40 to be received through the proximal section 2046 and contact the aligning inner surface 2044B.

FIG. 3b illustrates an embodiment wherein the aligning inner surface is provided in the needle receiving assembly 100.

The needle receiving assembly 100 can comprise a lateral protruding portion 1040, as discussed with reference to FIG. 1e. The lateral protruding portion 1040 can encompass a cavity 1050 of the fluid conducting element housing 40. As such, the lateral protruding portion 1040 can comprise an inner diameter that can correspond to the diameter of the cavity 1050 of the fluid conducting element housing 40. The inner diameter of the lateral protruding portion 1040 can taper along the downstream direction. In some embodiments and as illustrated in FIG. 3b, the inner diameter of the lateral protruding portion 1040 can taper along the downstream direction only along a longitudinal portion of the lateral protruding portion 1040. The rest of the lateral protruding portion 1040 may comprise a constant inner diameter which can be no smaller than the outer diameter of the needle housing 2040.

The preceding figures illustrate embodiments of the aligning component 2044, 1044 provided on an inner surface of the needle assembly 200 and/or the needle receiving assembly 100, referred to as an aligning inner surface and with referrals 2044B and 10448, respectively. It is clarified that an inner surface can refer to a surface that can laterally surround or enclose or encompass a cavity. That is, an inner surface can be present in hollow shaped structures having a cavity inside. The surface surrounding the cavity can be referred to as an inner surface. For example, the needle assembly 200 can comprise a cavity 2050 which is laterally surrounded by an inner surface of the needle assembly 200, more particularly by an inner surface of the needle housing 2040. At least a portion of an inner surface of the needle housing 2040 can be configured to increase alignment between the needle 202 and the needle receiving assembly 100 during a connection between the two. Thus, at least a portion of an inner surface of the needle housing 2040 can form an aligning inner surface 2044B.

Similarly, the needle receiving assembly 100 can comprise a cavity 1050 which can be laterally surrounded by an inner surface of the needle receiving assembly 100, more particularly by an inner surface of the fluid conducting element housing 40. At least a portion of an inner surface of the needle receiving assembly 100 can be configured to increase alignment between the needle 202 and the needle receiving assembly 100 during a connection between the two. Thus, at least a portion of the inner surface of the fluid conducting element housing 40 can form an aligning inner surface 10448.

In some embodiments, the aligning components 2044 and/or 1044 may be provided on an outer surface of the needle assembly 200 and/or needle receiving assembly 100. This is illustrated in the following figures.

Figure 4A:
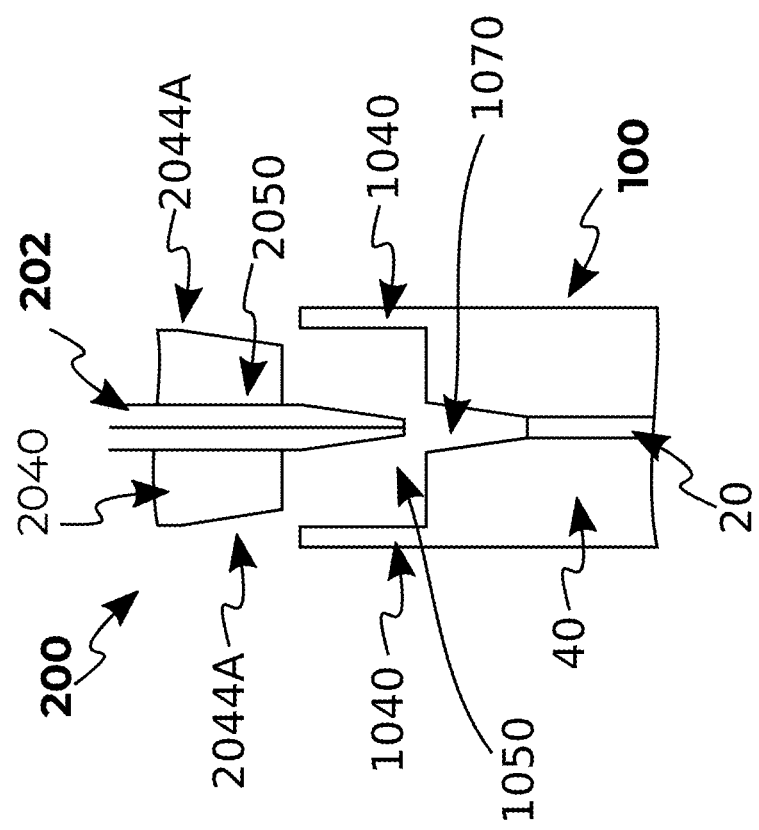
FIGS. 4a to 4c depict longitudinal sections of a needle assembly and a needle receiving assembly according to embodiments of the present invention wherein the needle assembly comprises an aligning outer surface.

FIG. 4a illustrates a needle assembly 200 and a needle receiving assembly 100. The needle assembly 200 comprises an aligning outer surface 2044A. In FIG. 4a, the cavity 2050 of the needle housing 2040 is depicted entirely occupied by the needle 202. That is, in some embodiments no portion of the needle receiving assembly 100 can be received in the needle assembly 200. In other words, in some embodiments, the cavity 2050 of the needle housing 2040 may comprise a constant diameter matching the outer diameter of the needle 202 and may be occupied entirely by the needle 202.

On the other hand, the needle receiving assembly 100 can further comprise a lateral protruding portion 1040. More particularly and as illustrated in FIG. 4a, a lateral portion of the fluid conducting element housing 40 can extend proximally beyond the needle seat 1070, hence forming the lateral protruding portion 1040 and a cavity 1050. Thus, the needle receiving assembly 100 can be configured to receive a portion of the needle assembly 200 in the cavity 1050. This can allow the inner surface of the lateral protruding portion 1040 to contact the outer surface of the needle housing 2040 during the connection between the needle assembly 200 and the needle receiving assembly 100.

In some embodiments, the outer diameter of the needle housing 2040 can taper along the downstream direction. That is, the outer diameter of the needle housing 2040 can decrease along the downstream direction. Hence, the shape of the needle housing 2040 can resemble the shape of a conical frustum with its base more distal than the rest of the conical frustum. As a result, the outer surface of the needle housing 2040 can facilitate increasing the alignment between the needle 202 and the needle receiving assembly 100 during the connection. In other words, the outer surface of the needle housing 2040 can form an aligning outer surface 2044A. Upon contact between the aligning outer surface 2044A and the inner walls of the lateral protruding portion 1040, the needle assembly 200 and the needle receiving assembly 100 can be concentrically aligned.

A taper angle can correspond to the aligning outer surface 2044A which can indicate the rate at which the outer diameter of the needle housing 2040 can taper along the downstream direction. The taper angle of the aligning outer surface 2044A can depend on the geometry of the needle receiving assembly 100 and needle assembly 200. This is illustrated in FIGS. 4b and 4c.

Figure 4C:
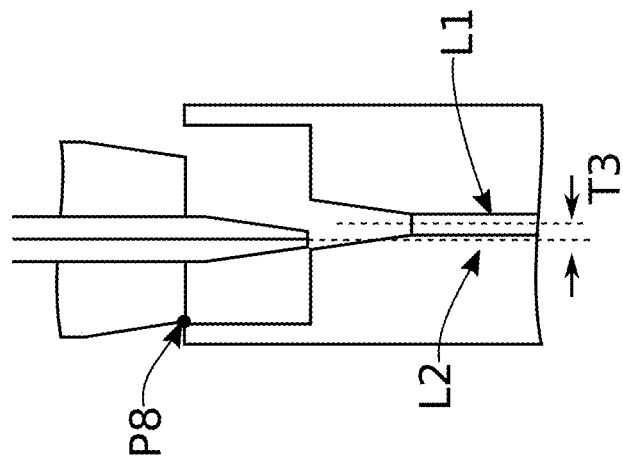
Figure 4B:
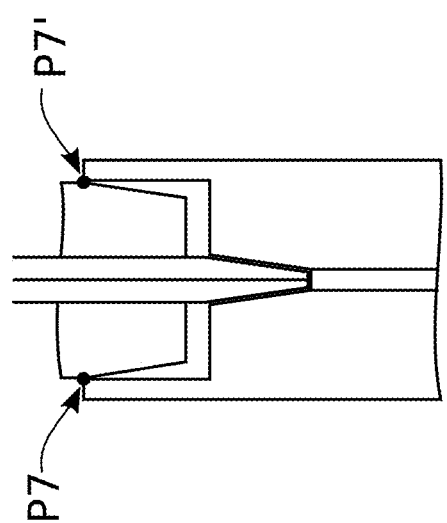

FIG. 4b illustrates the needle assembly 200 and the needle receiving assembly 100 properly connected and aligned with each other. At this position, a distal diameter of the aligning outer surface 2044A can be obtained (similar as above discussed in conjunction with FIG. 1b). More particularly, points P7 and P7' are defined as the section of the aligning (outer) surface 2044A being located at the same height in the axial direction as the most proximal portion of the lateral protruding portion 1040 of the needle receiving assembly 100 when the needle assembly 200 is fully inserted in the needle receiving assembly 100. The distal diameter of the aligning outer surface 2044A can be obtained by the distance between points P7 and P7'. Points P7 and P7' can be joined by a straight line passing through the center of a cross section of the aligning outer surface 2044A, which cross section comprises points P7 and P7' and is perpendicular to the needle 202. The distal diameter of the aligning outer surface 2044A can correspond (or be slightly larger) to the inner diameter of the lateral protruding portion 1040 of the needle receiving assembly 100. As will be understood, if the distal diameter is significantly smaller than the distance between points P7 and P7' a proper alignment between the needle 202 and the needle receiving assembly 100 cannot be guaranteed—as the aligning outer surface 2044A and the inner surface of the lateral protruding portion 1040 may not contact each other. On the other hand, if the distal diameter is larger than the distance between points P7 and P7', the needle receiving assembly 100 would not fit so that the needle 202 can be properly received in the needle seat 1070. Preferably, the distal diameter of the aligning outer surface 2044A, which corresponds to the maximum diameter of the aligning outer surface 2044A, can be slightly smaller (e.g. 0.01 mm-0.02 mm smaller) than the inner diameter of the lateral protruding portion 1040 of the needle receiving assembly 100. This can allow a portion of the needle assembly 200 that is distally beyond points P7 and P7' to be received in the cavity 1050 of the needle receiving assembly 100. This can be particularly advantageous to realize a tight connection between the needle 202 and the needle seat 1070.

Furthermore, when the needle assembly 200 and the needle receiving assembly 100 are properly connected and aligned with each other and when the needle assembly 200 is fully inserted in the needle receiving assembly 100, as illustrated in FIG. 4b, the cavity 1050 of the needle receiving assembly 100 can extend along the downstream direction beyond the needle housing 2040. Thus, the cavity 1050 of the needle receiving assembly 100 can provide space for the needle housing 2040 to be received, such that the connection between the needle 202 and the needle seat 1070 can be tightened.

FIG. 4c illustrates the needle assembly 200 and the needle receiving assembly 100 in the position wherein the needle 202 is about to enter the needle seat 1070 (or a housing portion extending proximally from a needle seat in some embodiments). At this position, a proximal radius of the aligning outer surface 2044A can be obtained based on a distance between point P8 and the central axis of the needle housing 2040. A proximal diameter of the aligning outer surface 2044A can then be obtained based on the proximal radius.

Using the distal and the proximal diameter of the aligning outer surface 2044A, the taper angle of the aligning outer surface 2044A can be determined.

At the same time, FIG. 4c illustrates the maximum misalignment that can be corrected by the aligning outer surface 2044A, illustrated by the distance T3 between the longitudinal central axis of the needle 202 (illustrated by the dashed line L2) and the longitudinal central axis of the needle seat 1070 (illustrated by the dashed line L1).

Figure 4D:
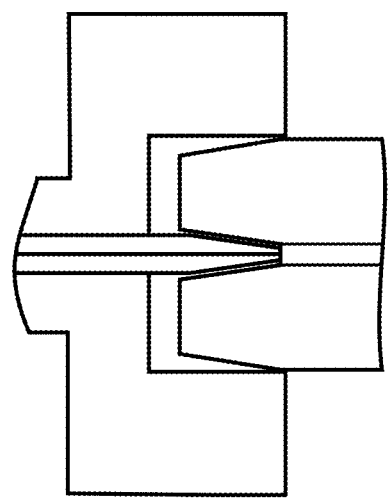
FIG. 4d depicts a longitudinal section of a needle assembly and a needle receiving assembly according to embodiments of the present invention wherein the needle receiving assembly comprises an aligning outer surface.
Figure 4D:
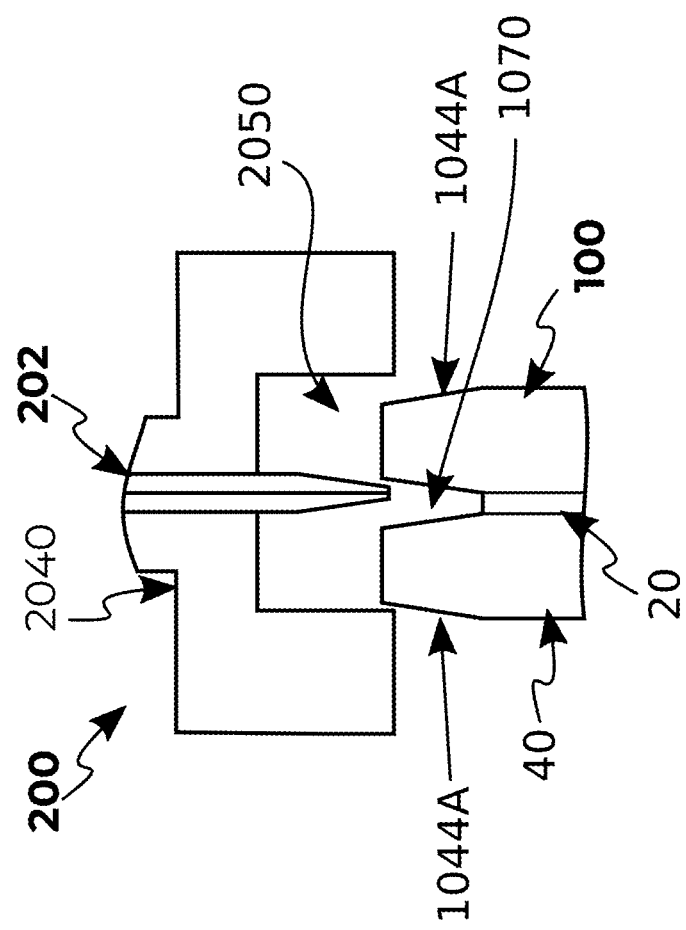

FIG. 4d illustrates an embodiment of the needle receiving assembly 100 comprising an aligning outer surface 1044A. In such embodiments, the needle housing 2040 can comprise a cavity 2050 which can only be partially occupied by the needle 202. The rest of the cavity 2050 can be occupied, by a portion of the fluid conducting element housing 40 of the needle receiving assembly 100.

The diameter of the cavity 2050 and of the portion of the fluid conducting element housing 40 that can be received in the cavity 2050 can be configured such that during the insertion of said portion of the fluid conducting element housing 40 into the cavity 2050, the outer lateral surface of the said portion of the fluid conducting element housing 40 can contact the inner surface of the needle housing 2040 laterally surrounding the cavity 2050. To facilitate the connection, the outer lateral surface of the portion of the fluid conducting element housing 40 that can be received in the cavity 2050 can be configured to increase alignment between the needle 202 and the needle receiving assembly 100.

In some embodiments, the outer diameter of said portion of the fluid conducting element housing 40 can increase along the downstream direction, thus forming an outer aligning surface 1044A. Upon contact between the outer aligning surface 1044A and the inner surface of the needle housing 2040 that laterally surrounds the cavity 2050, the needle assembly 200 and the needle receiving assembly 100 can be concentrically aligned.

Note that in FIG. 4d, the needle receiving assembly 100 is illustrated without a lateral protruding portion 1040. However, it will be understood that the needle receiving assembly 100 may further comprise the lateral protruding portion 1040.

FIG. 5a illustrates a needle assembly 200 comprising an aligning outer surface 2044A which diameter tapers with different rates. That is, in contrast to the embodiment of FIGS. 4a to 4c wherein the diameter of the aligning outer surface 2044A is illustrated tapering at a constant rate, in the embodiment illustrated in FIG. 5a, the diameter of the aligning outer surface 2044A can taper with multiple different rates.

More particularly, the aligning outer surface 2044A can comprise a proximal aligning outer surface 3005 and a distal aligning outer surface 3006, wherein the proximal aligning outer surface 3005 is more proximal than the distal aligning outer surface 3006. The proximal aligning outer surface 3005 and the distal aligning outer surface 3006 can comprise only one cross sectional size perpendicular to the axial direction in common. Said common cross-section can comprise a diameter that corresponds to the minimum diameter of the distal aligning outer surface 3006 and to the maximum diameter of the proximal aligning outer surface 3005.

Furthermore, the diameters of the proximal and the distal aligning outer surfaces 3005, 3006 can taper at different rates along the axial direction when moving from a distal position to a proximal position (i.e. along the downstream direction). In FIG. 5a, the diameter of the proximal aligning outer surface 3005 can taper at a higher rate (i.e. faster) compared to the diameter of the distal aligning outer surface 3006. In other words, the taper angle of the proximal aligning outer surface 3005 can be larger than the taper angle of the distal aligning outer surface 3006.

Figure 5D:
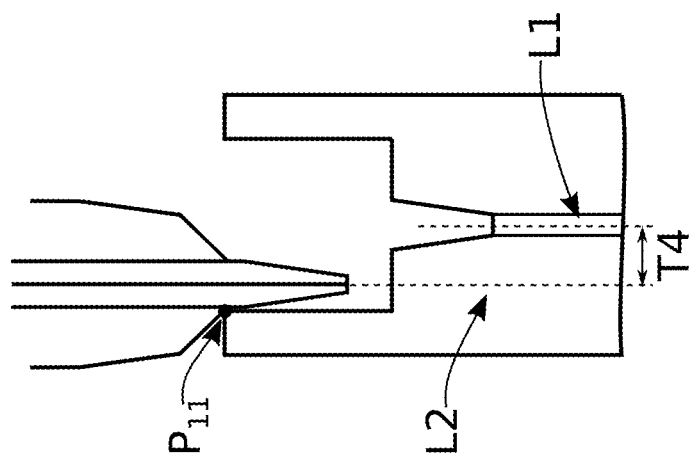
Figure 5C:
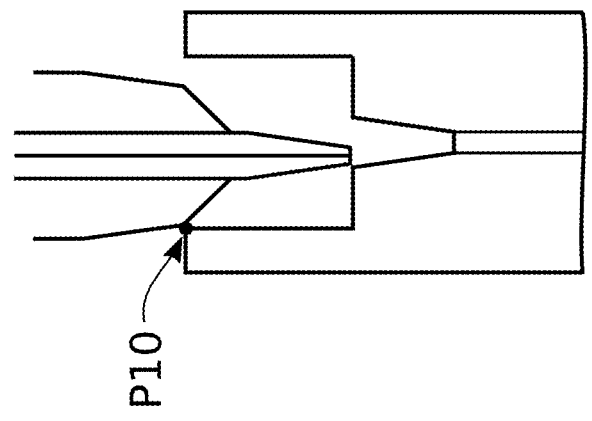
Figure 5B:
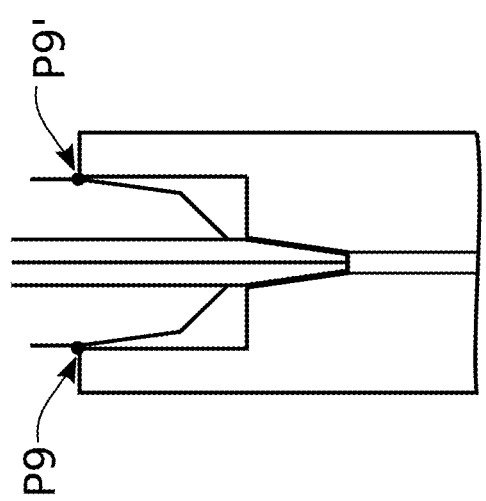

The taper angle of the distal aligning outer surface 3006 can be determined based on the diameter (P9, P9') and the distance of point P10 from the central axis of the needle housing 2040, as illustrated in FIGS. 5b and 5c. FIG. 5d illustrates the maximum misalignment (i.e. tolerance) that can be corrected by the aligning outer surface 2044A. It is illustrated by distance T4 measured as the distance between the longitudinal central axis of the needle 202 (illustrated by the dashed line L2) and the longitudinal central axis of the needle seat 1070 (illustrated by the dashed line L1).

This arrangement can be advantageous over the one illustrated in FIGS. 4a to 4d for the following reasons: As an initial matter, "capturing" the needle receiving assembly 100 and aligning the needle 202 inside the needle seat 1070 are performed by the proximal aligning outer surface 3005 and distal aligning outer surface 3006, respectively. Thus, the proximal aligning outer surface 3005 and the distal aligning inner surface 3006 can be configured or optimized independently which may result in a more efficient configuration of the aligning outer surface 2044A.

Figure 5E:
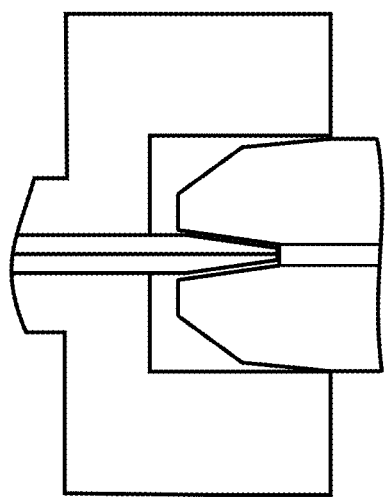
FIG. 5e depicts a longitudinal section of a needle assembly and a needle receiving assembly according to embodiments of the present invention wherein the needle receiving assembly comprises an aligning outer surface.
Figure 5E:
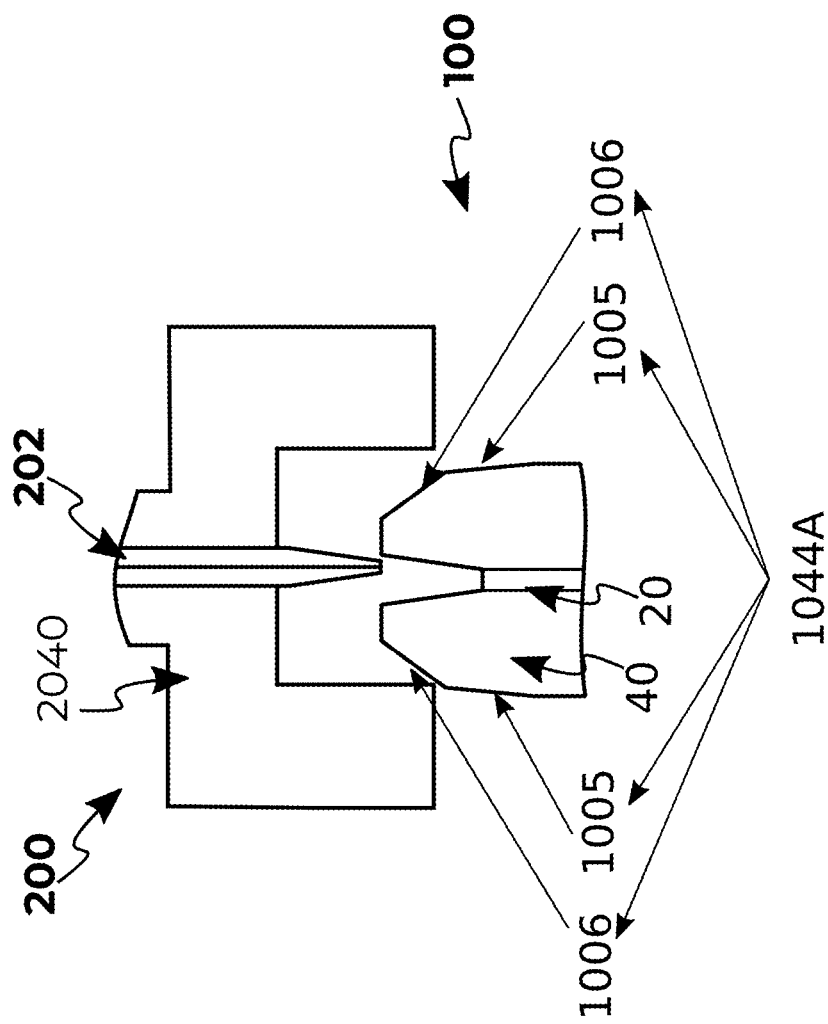

Similarly, the aligning inner surface with multiple taper angles can be provided on the needle receiving assembly 100. As illustrated in FIG. 5e, the needle receiving assembly 100 can comprise an aligning outer surface 1044A comprising a distal aligning inner surface 1005 and a proximal aligning inner surface 1006. The aligning outer surface 1044B of the needle receiving assembly 100 can be configured similar to the aligning outer surface 2044B of the needle assembly 200.

Figure 6A:
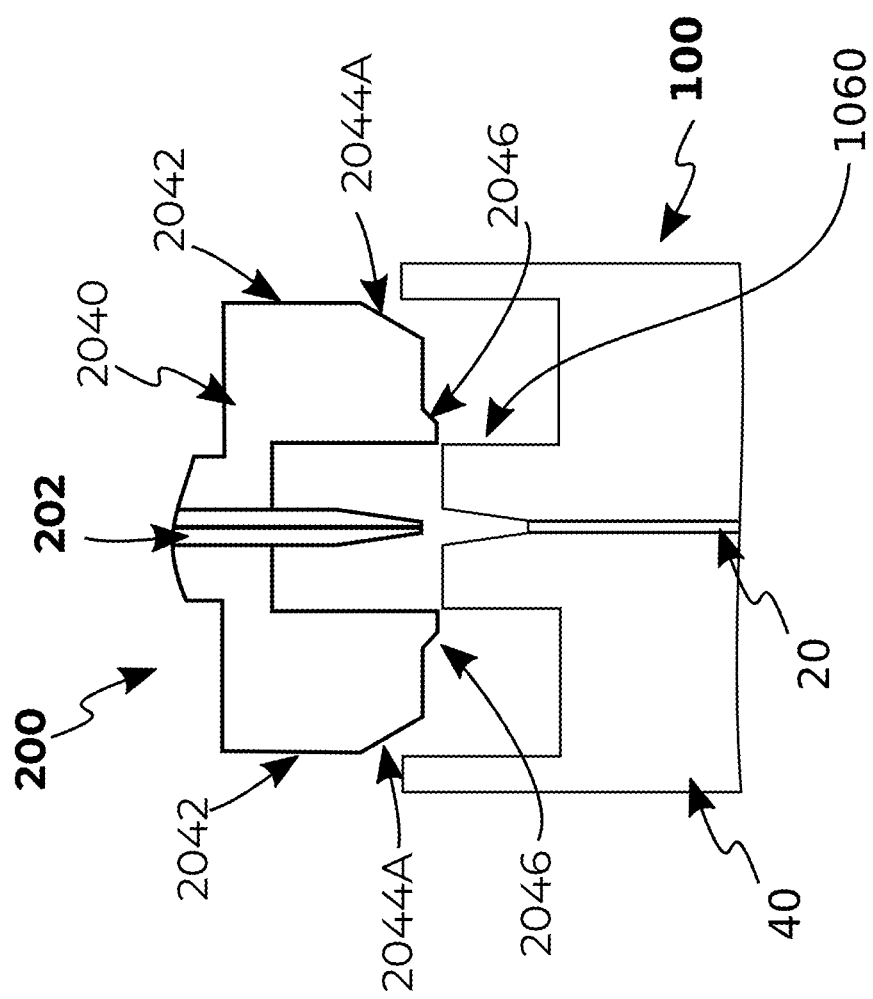
FIGS. 6a to 6d depict longitudinal sections of a needle assembly and a needle receiving assembly according to embodiments of the present invention wherein the needle assembly comprises an aligning outer surface.

FIG. 6a illustrates a further embodiment of needle assembly 200 comprising an outer aligning outer surface 2044A.

The needle fluid conducting element housing 40 of the needle assembly 200 can comprise a distal portion 2042 and a proximal portion 2046, as discussed with reference to FIG. 3a.

Between the proximal portion 2046 and the distal portion 2042 the needle housing 2040 can comprise a longitudinal portion wherein the outer diameter of the needle housing can taper in the downstream directions, thus forming an aligning outer surface 2044A. The portion of the needle housing 2040 wherein the aligning outer surface 2044A can be formed can comprise a length along the axial direction that can amount to at least 5%, preferably at least 10%, more preferably at least 20%, such as 30% of the total length along the axial direction of the needle housing 2040.

Alternatively, in some embodiments, the aligning outer surface 2044A can be provided most proximal within the needle assembly 200. For example, the longitudinal portion wherein the outer diameter of the needle housing tapers in the downstream directions, thus forming an aligning outer surface 2044A, can comprise the proximal portion 2046.

Figure 6B:
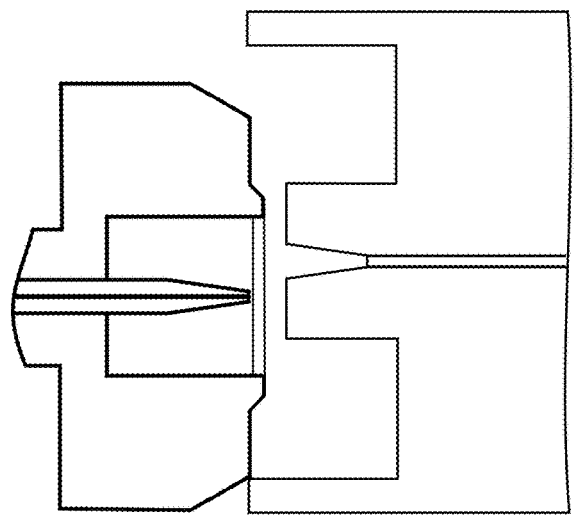
Figure 6C:
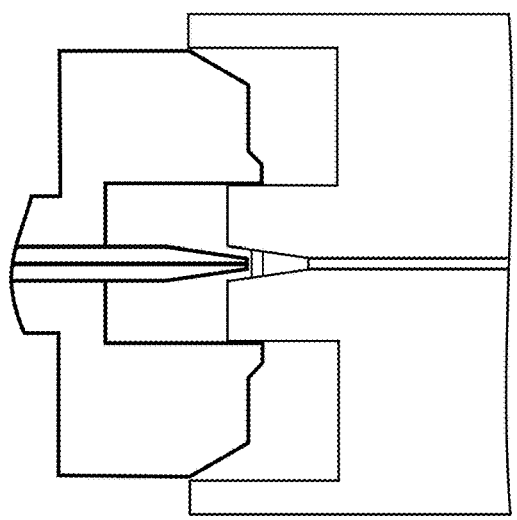
Figure 6D:
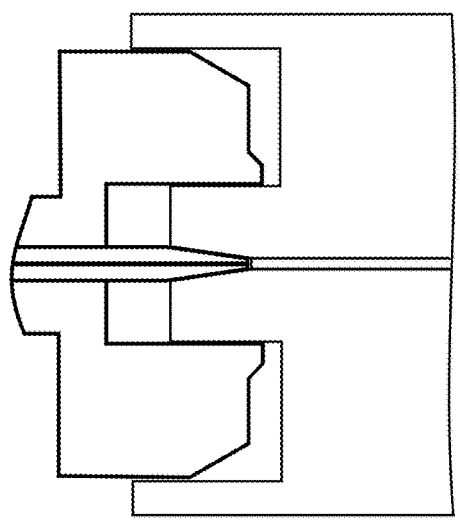

FIGS. 6b to 6d illustrate the needle assembly 200 approaching the needle receiving assembly 100 and being guided by the aligning outer surface 2044A in proper alignment. As will be understood, the needle receiving assembly 100 can approach the needle assembly 200 or they can both approach each other.

Furthermore, as illustrated in FIG. 6d, both the cavity 2050 of the needle assembly 200 and the cavity 1050 of the needle receiving assembly 100 provide space for the needle receiving assembly 100 and the needle assembly 200 to further approach each other. This can facilitate tightening the connection between the needle 202 and the needle seat 1070.

FIG. 7a depicts a still further embodiment of the needle assembly 200 and the needle receiving assembly 100.

The needle assembly 200, as discussed, can comprise a needle 202 which can be mounted in a needle housing 2040. Preferably, the needle 202 can be unreleasably attached or mounted in the needle housing 2040. For example, the needle 202 can be welded to the needle housing 2040, as illustrated by the welded joint 2060.

The needle housing 2040 can comprise a hollow shape. That is, the needle housing 2040 can comprise a cavity 2050 which can extend through the entire length along the axial direction of the needle housing 2040. This can allow the needle 202 to be placed in the needle housing 2040. In other words, the needle housing 2040 can surround the needle 202 and the tip of the needle 202 is not blocked by the needle housing 2040, such that, a sample may flow out of the needle 202 and out of the needle hosing 2040.

In a most distal portion, the cavity 2050 can comprise a diameter that can match to the outer diameter of the needle 202. In said portion, also referred to as needle holding portion of the cavity 2050, the cavity 2050 can snugly or exactly fit the needle 202. For example, the outer diameter of the needle 202 and the corresponding diameter of the distal portion of the cavity 2050 can be in the range of 0.1 mm to 2 mm, preferably 0.3 mm to 1.8 mm, more preferably between 0.5 mm to 1.6 mm. This can facilitate rendering an unreleasable attachment between the needle 202 and the needle housing 2040.

Downstream the needle holding portion of the cavity 2050, the cavity 2050 may comprise a wider portion wherein the diameter of the cavity 2050 can be larger than the outer diameter of the needle 202. In such embodiments, the diameter of the wider portion of the cavity 2050 can generally correspond to the outer diameter of a portion of the needle receiving assembly 100 surrounding the needle seat 1070. This can allow the portion of the needle receiving assembly 100 surrounding the needle seat 1070 (i.e. the central protruding portion 1060) to be received in the cavity 2050 of the needle assembly 200. The wider portion of the cavity 2050 can comprise a diameter of at least 2 mm and at most 10 mm, preferably at most 5 mm, such as, 2.7 mm. A quotient of the division of the diameter of the wider portion of the cavity 2050 with the outer diameter of the needle 202 can be in the range of 1.1 to 100, preferably 2 to 50, more preferably 3 to 10, such as 4.5.

In some embodiments, the diameter of the cavity 2050 may transition abruptly from the smaller diameter of the needle holding portion of the cavity 2050 to the larger diameter of the wider portion of the cavity 2050, as illustrated in FIG. 7a.

It will be understood that the terms diameter of the cavity 2050 and inner diameter of the needle housing 2040 can refer to the same diameter.

The wider portion of the cavity 2050 can comprise a length in the axial direction that can amount to at least 20%, preferably at least 40%, more preferably at least 60% and at most 90%, preferably at most 80%, such as 75% of the length in the axial direction of the needle housing 2040. For example, the most distal cross section of the cavity 2050 can be positioned at a distance of 0.5 mm to 20 mm, preferably 1 mm to 10 mm, more preferably 2 mm to 5 mm, such as, 2.7 mm from the tip of the needle 202.

The needle housing 2040, can surround a portion of the needle 202, preferably a proximal portion of the needle 202. It will be understood that the needle housing 2040 may further extend distally. The needle housing 2040 can comprise a length along the axial direction in the range of 1 mm to 50 mm, preferably 2 mm to 10 mm, such as 3.5 mm.

Furthermore, the needle housing 2040 can comprise a maximum extension in the radial direction in the range of 2 mm to 50 mm, preferably 4 mm to 20 mm, more preferably 5 mm to 10 mm, such as 7.5 mm. More particularly, a quotient of the division of the width of the needle housing 2040 in the radial direction and the outer diameter of the needle 202 can be between 2 to 100, preferably 5 to 20, more preferably 8 to 12.

The needle housing 2040 can comprise a distal portion 2042. The distal portion 2042 of the needle housing 2040 can surround a distal portion of the cavity 2050 which may include the needle holding portion of the cavity 2050 and a part of the wider portion of the cavity 2050. In other words, a distal part of the distal portion 2042 can comprise an inner diameter corresponding to the diameter of the needle holding portion of the cavity 2050 and a proximal part of the distal portion 2042 can comprise an inner diameter that corresponds to the diameter of the wider portion of the cavity 2050. Furthermore, the distal portion 2042 can amount to at least 40% and at most 80%, such as, 65% of the extension along the axial direction of the needle housing 2040. For example, the distal portion 2042 can comprise a length along the axial direction in the range of 0.5 mm to 40 mm, preferably 1 mm to 10 mm, more preferably 2 mm to 5 mm, such as 2.3 mm.

Moreover, the outer diameter of the distal portion 2042 can correspond to the maximum extension in the radial direction of the needle housing 2040. It can be in the range of 2 mm to 50 mm, preferably 4 mm to 20 mm, more preferably 5 mm to 10 mm, such as 7.5 mm. Further still, the distal portion 2042 of the needle housing 2040 can be characterized by a constant outer diameter. That is, each cross-section of the distal portion 2042 that is perpendicular to the axial direction can comprise the same outer diameter. This may increase the ergonomics of handling the needle assembly 200, for an example, during the replacement of the needle 202 or the whole needle assembly 200.

Downstream of the distal portion 2042, the needle housing 2040 can comprise a proximal portion 2046. The proximal portion 2046 can be more proximal than the rest of the needle assembly 200. The proximal portion 2046 can surround a most proximal part of the cavity 2050. In some embodiments, the proximal portion 2046 can protrude proximally beyond the tip of the needle 202. In such embodiments, the proximal portion 2046 can also be referred to as a protrusion 2046. The length of the protrusion 2046 in the axial direction can be in the range of 0.1 mm to 2 mm, preferably 0.2 mm to 1 mm, such as 0.25 mm. The proximal portion 2046 can amount to at least 1% and at most 20%, preferably 5% to 8% of the extension along the axial direction of the needle housing 2040.

The protrusion 2046 can be advantageous for protecting the needle 202, as it may stop the needle 202 from stinging or bumping into other surface which can damage the needle 202, produce abrasion and/or block the needle 202. At the same time, the protrusion 2046 can increase safety of handling the needle assembly 200. More particularly, the protrusion 2046 may protect a handler of the needle assembly 200 from being pricked by the needle 202.

Between the distal portion 2042 and the proximal portion 2046, the outer diameter of the needle housing 2040 may decrease along the downstream direction. Thus, the needle housing 2040 may comprise an aligning outer surface 2044A, which can be positioned immediately downstream the distal portion 2042.

The aligning outer surface 2044A may comprise a most distal cross section, which is more distal than the rest of the cross sections of the aligning outer surface 2044A, and a most proximal cross section, which is more proximal than the rest of the aligning outer surface 2044A. The most distal cross section of the aligning outer surface 2044A can comprise a diameter that can be equal to the outer diameter of the distal portion 2042. In some embodiments, the most distal cross-section of the aligning outer surface 2044A may be coincident with the most proximal cross-section of the outer surface of the distal portion 2042. The diameter of the most distal cross-section of the aligning outer surface 2044A can correspond to the largest extension of the aligning outer surface 2044A in the radial direction. On the other hand, the most proximal cross-section of the aligning outer surface 2044A can comprise a diameter which can correspond to the smallest extension of the aligning outer surface 2044A in the radial direction. That is, the diameters of cross-sections of the aligning outer surface 2044A may decrease (e.g., monotonically) from the most distal cross-section to the most proximal cross-section.

The diameter of the most proximal cross-section of the aligning outer surface 2044A can be at least 30%, preferably at least 40%, more preferably at least 60% and at most 90%, such as 80% to 85% of the diameter of the most distal cross-section of the aligning outer surface 2044A.

The aligning outer surface 2044 can amount to at least 5% and at most 60%, such as, 30% of the extension along the axial direction of the needle housing 2040. For example, aligning outer surface 2044 can comprise a length along the axial direction of at least 0.5 mm and at most 20 mm, preferably at most 10 mm, more preferably at most 5 mm, such as 1 mm.

In FIG. 7a, a needle receiving assembly 100 is also illustrated. The needle receiving assembly 100 and the needle assembly 200 are configured correspondingly to each other, such that they can facilitate fluidly connecting the needle 202 of the needle assembly 200 with the fluid conducting element 20 of the needle receiving assembly 100. Put simply, the needle assembly 200 and the needle receiving assembly 100 are configured in a plug and socket manner.

The needle receiving assembly 100 can comprise a fluid conducting element 20 that can be mounted in a fluid conducting element housing 40, which for the sake of brevity can also be referred to as a housing 40. The fluid conducting element housing 40 can comprise a hollow shape, thus allowing for the fluid conducting element 20 to be inserted into the fluid conducting element housing 40. In other words, the fluid conducting element 20 can be surrounded by the fluid conducting element housing 40. The connection between the fluid conducting element 20 and the fluid conducting element housing 40 can preferably be an unreleasable connection. Thus, the fluid conducting element 20 and the fluid conducting element housing 40 cannot be separated from each other under normal operation of the needle receiving assembly 100.

Concentrically aligned with the fluid conducting element 20 and more proximal than (i.e. upstream) the fluid conducting element 20, the needle receiving assembly 100 can comprise a needle seat 1070. The needle seat 1070 may comprise a cavity (not to be confused with the cavity 1050) wherein the needle 202 can be inserted. It will be understood that the needle seat 1070 comprises a sealing element 10 to seal against the needle 202 when inserted. In some embodiments (as discussed below), the sealing element 10 seals both the needle 202 (when the needle 202 is inserted in the needle receiving assembly 100) and the fluid conducting element 20.

The needle seat 1070 can preferably be provided in a central portion 1060 of the needle receiving assembly 100. In some embodiments, the central portion 1060 can protrude such that it can be surrounded by the cavity 1050. In such embodiments, the central portion 1060 can also be referred to as a central protruding portion 1060. Further, the central portion 1060 may comprise a diameter corresponding to the diameter of the cavity 2050 of the needle assembly 200. In other words, the needle assembly 200 and the needle receiving assembly 100 can be configured such that the central portion 1060 can be received in the cavity 2050 of the needle assembly 200. As the central portion 1060 is received in the cavity 2050, the needle 202 can be received in the needle seat 1070.

Furthermore, the needle receiving assembly 100 can comprise a lateral protruding portion 1040. The lateral protruding portion 1040 can surround the cavity 1050 of the needle receiving assembly 100.

Figure 7D:
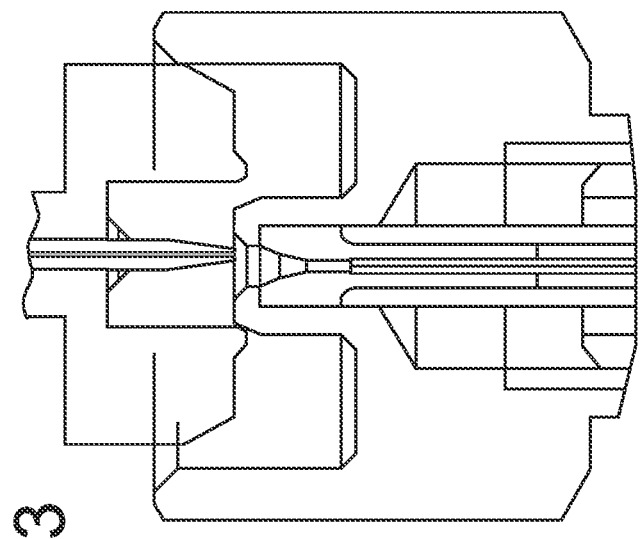
Figure 7C:
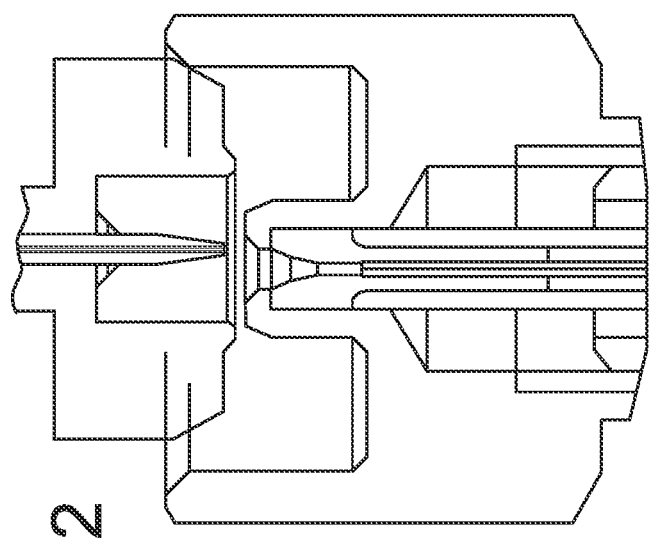

In other words, the needle receiving assembly 100 can comprise a cavity 1050. On the bottom of the cavity 1050 can be a base 1080. The base 1080 can be a non-lateral inner surface of the needle receiving assembly 100 that abuts the cavity 1050 and is more distal than the cavity 1050. From the base 1080 a lateral protruding portion 1040 may protrude proximally beyond the base 1080. The lateral protruding portion 1040 can laterally surround the cavity 1050. Further, from the base 1080, the central protruding portion 1060 may protrude proximally beyond the base 1080. The central protruding portion 1060 can be surrounded by the cavity 1050. The lateral protruding portion 1040 may protrude proximally beyond the central protruding portion 1060. Furthermore, the base 1080 can be provided such that when the needle receiving assembly 100 and the needle assembly 200 are connected and aligned and when the needle assembly 200 is fully inserted in the needle receiving assembly 100 as illustrated in FIG. 7f, then the base 1080 is more downstream than the needle housing 2040. That is, the needle housing 2040 cannot contact the base 1080. Again, thus, the axial force used to press the needle assembly 200 and the needle receiving assembly 100 together is (almost) completely supplied to the contact between the needle 202 and the sealing element 1070, which may lead to a tight seal between these two elements.

The lateral protruding portion 1040 may comprise a length along the axial direction in the range of 1 mm to 50 mm, preferably 2 mm to 10 mm, more preferably 3 mm to 5 mm, such as 4 mm. The central protruding portion 1060 may comprise a length along the axial direction in the range of 20% to 100%, preferably 30% to 80%, more preferably 40% to 60% of the length of lateral protruding portion 1040 along the axial direction. For an example, the length along the axial direction of the central protruding portion 1060 may be in the range of 0.2 mm to 50 mm, preferably 1 mm to 10 mm, more preferably 1.5 to 3 mm, such as 2 mm.

The lateral protruding portion 1040 may comprise an outer diameter that can be at least 1.01 times and at most 2 times, preferably at least 1.1 times and at most 1.5 times, such as, 1.3 times the outer diameter of the needle housing 2040. Furthermore, the lateral protruding portion 1040 may comprise an inner diameter which can be at least equal to the outer diameter of the needle housing 2040. As such, the needle housing 1040 can be received in the cavity 1050 and can be surrounded by the lateral protruding portion 1040. In some embodiments, the inner diameter of the lateral protruding portion 1040 can exactly match the outer diameter of the needle housing 2040. In some embodiments, the inner diameter of the lateral protruding portion 1040 can be larger than the outer diameter of the needle housing 2040, e.g., by 0.5 mm. For example, the lateral protruding portion 1040 can comprise an outer diameter in the range of 3 mm to 51 mm, more preferably 5 to 21 mm, more preferably 6 mm to 15 mm, such as, 10 mm and an inner diameter in the range of 2 mm to 50 mm, preferably 4 mm to 20 mm, more preferably 5 mm to 10 mm, such as 8 mm.

On the other hand, the central protruding portion 1060 can comprise an outer diameter that does not exceed the diameter of the cavity 2050 of the needle assembly 200. This way, the central protruding portion 1060 can be received in the cavity 2050 of the needle assembly 200. In some embodiments, the inner diameter of the needle housing 2040 (i.e. the diameter of the cavity 2050) can be configured to fit exactly (within a tolerance as specified by the ISO clearance fit +0.02/+0.04 to 0/−0.02) to the central protruding portion 1060.

Thus, when the needle assembly 200 and the needle receiving assembly 100 are completely connected with each other (e.g. see FIG. 7f), the central protruding portion 1060 can be surrounded by the needle housing 2040 and the needle housing 2040 can be laterally surrounded by the lateral protruding portion 1040. Furthermore, to tighten the connection such that there can be no leakage, typically the needle 202 is pressed against the needle seat 1070. Thus, the needle 202 may exert an axial force in the range of 20 N to 50 N on the needle seat. It will be understood that when the needle 202 is pressed against the sealing element 10 (or, generally, the needle seat), the base 1080 is generally not contacted by the needle assembly 200. Thus, any force exerted axially against the needle assembly 200 is used to press the needle 202 into the needle seat, as depicted, e.g., in FIG. 7f.

The outer diameter of the central protruding portion 1060 may taper in a direction opposite to the downstream direction. More particularly, the central protruding portion 1060 may comprise a portion with a constant outer diameter and a portion with a tapering outer diameter. The portion of the central protruding portion 1060 with a tapering outer diameter may amount to at least 10%, preferably at least 20% and at most 100%, preferably at most 50%, more preferably at most 30%, such as 25% of the total extension of the central protruding portion 1060 along the axial direction. For example, the portion of the central protruding portion 1060 with a tapering outer diameter may comprise a length along the axial direction in the range of 0.1 to 2 mm, such as 0.5 mm. The portion of the central protruding portion 1060 with a tapering outer diameter can be the most proximal portion of the central protruding portion 1060.

In other words, the needle receiving assembly 100 can comprise an aligning outer surface 1044A positioned on the outer surface of the central protruding portion 1060. The aligning outer surface 1044A can comprise a most proximal cross-section and a most distal cross section. The most proximal cross-section of the aligning outer surface 1044A may coincide with the most proximal cross-section of the central protruding portion 1060. The diameter of the most proximal cross-section of the aligning outer surface 1044A is smaller than the diameter of the most distal cross-section of the aligning outer surface 1044A. Furthermore, the diameter of cross-sections of the aligning outer surface increases monotonically from the most proximal cross-section of the aligning outer surface 1044A to the most distal cross-section of the aligning outer surface 1044A along the axial direction.

In addition or alternatively to the outer aligning surfaces 2044A, 1044A, the needle assembly 200 and the needle receiving assembly 100 can be provided with the inner aligning outer surfaces 2044B, 1044B, respectively. More particularly, the aligning inner surface 2044B can be provided to the needle assembly 200 on the inner surface of the needle housing 2040 laterally enclosing the cavity 2050. On the other hand, the aligning inner surface 10448 can be provided on the inner surface of the fluid conducting element housing 40 laterally enclosing the cavity 1050. FIGS. 7b to 7f illustrate the needle assembly 200 and the needle receiving assembly 100 at different proximities with each other, to achieve a connection between the two.

Figure 7B:
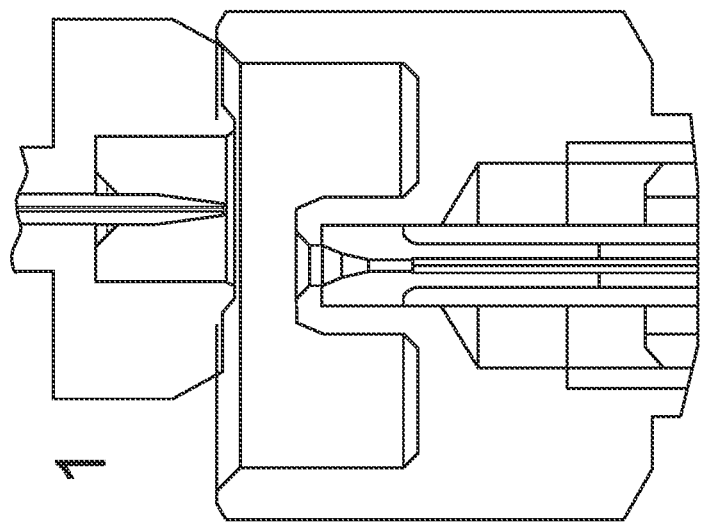
Figure 7F:
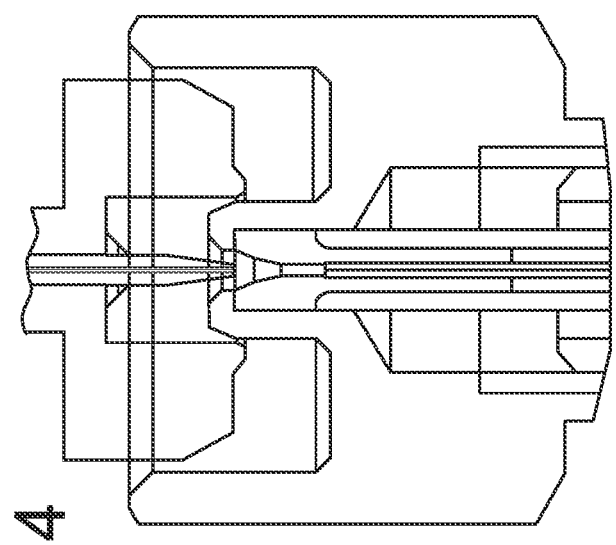
Figure 7E:
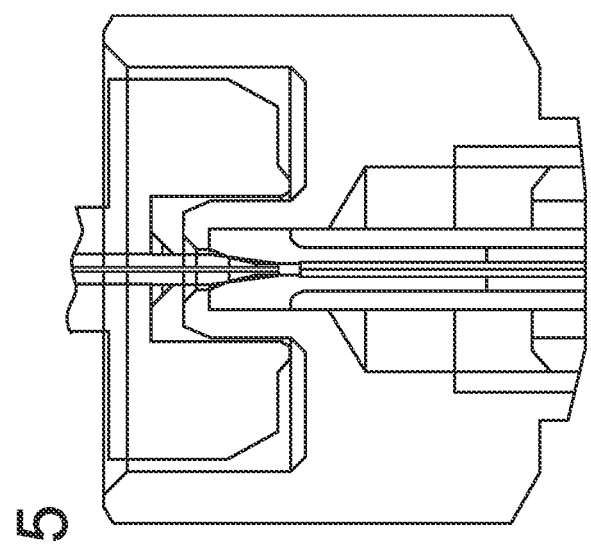

In FIG. 7b, the needle assembly 200 is depicted about to enter the cavity 1050 of the needle receiving assembly 100. At this position, the aligning outer surface 2044A can contact the inner surface of the fluid conducting element housing 40. Alternatively or additionally, at this position the aligning inner surface 1044B of the needle receiving assembly 100 can contact the outer surface of the needle hosing 2040. The aligning outer surface 2044A of the needle assembly 200 and/or the aligning outer surface 1044A of the needle receiving assembly 100 can increase the concentric alignment (i.e. alignment in the radial direction) between the needle receiving assembly 100 and the needle assembly 200, as illustrated in FIG. 7c. The aligning outer surface 2044A of the needle assembly 200 and/or the aligning outer surface 1044A of the needle receiving assembly 100 can increase the concentric alignment until the central protruding portion 1060 is about to enter the cavity 2050 of the needle housing 2040, as illustrated in FIG. 7d. At this position, the aligning outer surface 1044A of the needle receiving assembly 100 can contact the inner surface of the needle housing 2040. Alternatively or additionally, at the position of FIG. 7d, the aligning inner surface 2044B of the needle assembly 200 can contact the outer surface of the central protruding portion 1060. This can further increase the concentric alignment between the needle assembly 200 and the needle receiving assembly 100, more particularly between the needle 202 and the needle seat 1070, as illustrated in FIG. 7e. Then, the needle 202 can be thrusted into the needle seat 1070, as illustrated in FIG. 7f.

Thus, the needle 202 can be brought into alignment with the needle seat 1070 only by means of contact between the surfaces of the needle housing 2040 and fluid conducting element housing 1040. Furthermore, the needle 202 is inserted into the needle seat 1070 after it is properly aligned. This can avoid the needle pricking on the walls of the needle seat 1070 and/or other surface of the fluid conducting element housing 40.

Figure 8B:
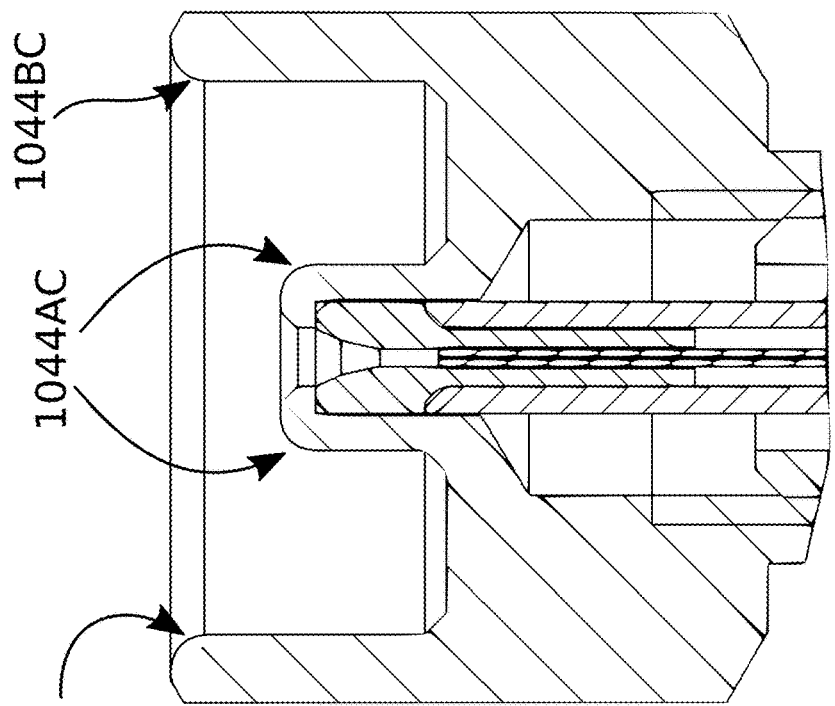
FIGS. 8a to 8b depict longitudinal sections of a needle assembly and a needle receiving assembly according to embodiments of the present invention with convex aligning surfaces.
Figure 8A:
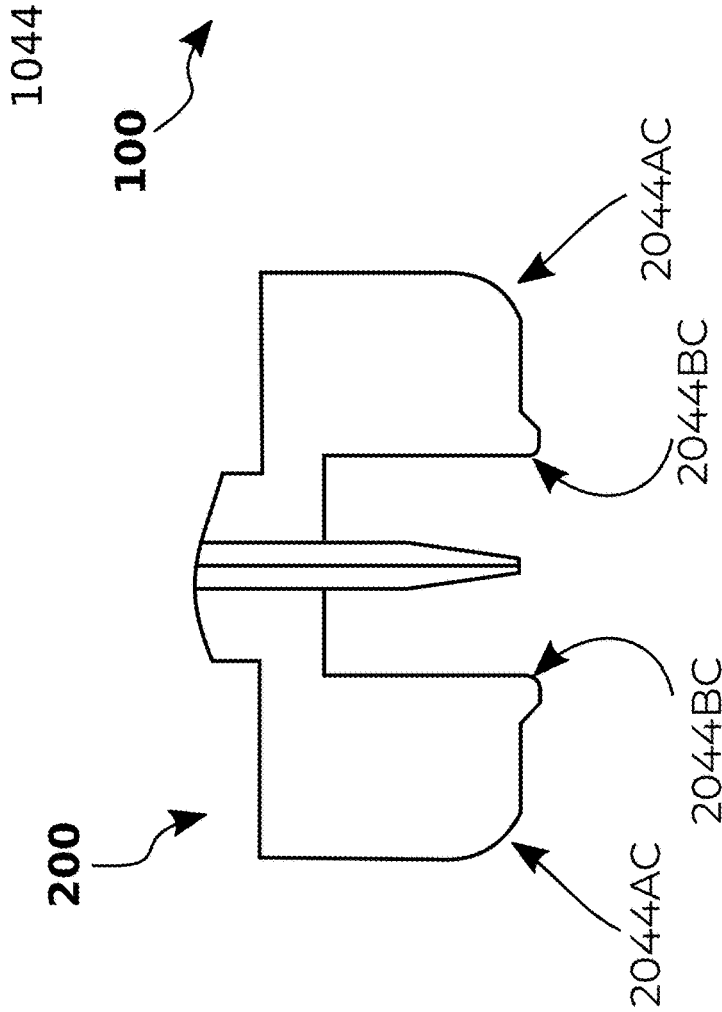

In some embodiments, the aligning outer surface 2044A and/or the aligning inner surface 2044B of the needle assembly 200 can comprise a convex shape. This is illustrated in FIG. 8a. That is, the diameter of the aligning outer surface 2044A and/or the aligning inner surface 2044B of the needle assembly 200 may not necessarily taper linearly.

Similarly, the aligning outer surface 1044A and/or the aligning inner surface 1044B of the needle receiving assembly 100 can comprise a convex shape. This is illustrated in FIG. 8b. That is, the diameter of the aligning outer surface 1044A and/or the aligning inner surface 1044B of the needle receiving assembly 100 may not necessarily taper linearly.

In the following, the needle receiving assembly 100 will be discussed in more detail.

Figure 9:
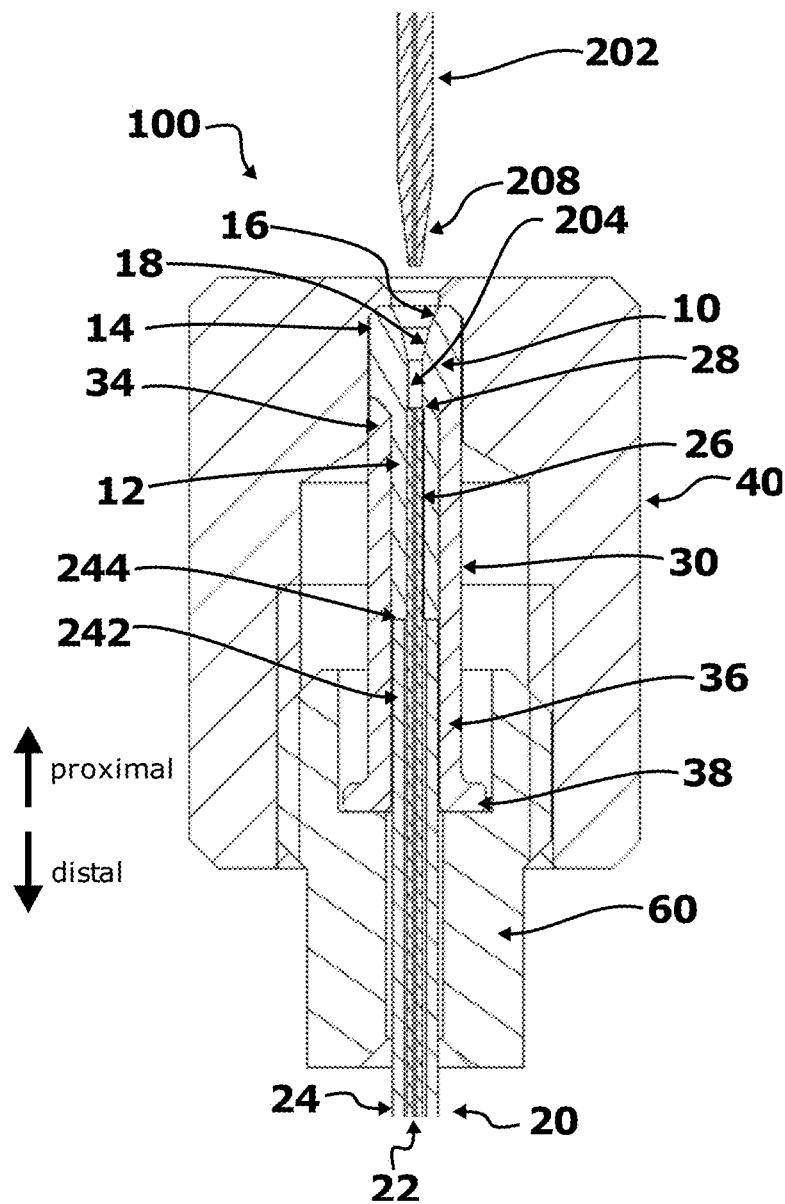
FIG. 9 depicts a longitudinal section of an assembly for receiving a fluid from a needle according to embodiments of the present invention.

Some embodiments of the present invention relate to an assembly 100 for receiving a fluid from a needle 202, as depicted, e.g., in FIG. 9. It will be understood that this assembly 100 may be part of a sampler to (e.g., automatically) provide a sample to a liquid chromatography system. More particularly, the needle 202 may be moved to a sample vial, may draw in the sample, may subsequently be moved to the assembly 100 and may then introduce the sample into the assembly 100. Furthermore, it will be understood that the needle 202 may be part of a needle assembly 200 as discussed above (although this is not a necessity). Moreover, it will be understood that the features described below in conjunction with FIGS. 9 to 14 may be employed in the embodiments discussed above in conjunction with FIGS. 1a to 8b.

The assembly 100 comprises different elements, including a fluid conducting element 20 and a sealing element 10. The fluid conducting element 20 can be a capillary 20 (i.e. a tube) with a relatively small inner diameter for guiding the fluid to other elements (e.g., to a chromatographic column). That is, the assembly 100 can generally be intended to transfer the fluid from the needle 202 to the capillary 20. Alternatively, the fluid conducting element 20 can be a chromatographic column 20. This may be advantageous, as a volume between the needle 202 and the chromatographic column may thus be reduced. In such embodiments, the assembly 100 can be generally intended to transfer the fluid from the needle 202 to the chromatographic column 20.

The sealing element 10 seals against the fluid conducting element 20 and provides a needle seat.

Throughout this specification, the terms proximal and distal are used. As depicted in FIG. 9, the assembly 100 may receive a needle 202. Generally, when the needle 202 is inserted, the closer an element is to the needle 202, the more proximal it is, and the more distanced an element is from the needle 202, the more distal it is. Further still, it will be understood that a sample (or a liquid) may be introduced from the needle 202 into the assembly 100. That is, the more distal an element is, the further "downstream" it is.

To fulfill its dual function, the sealing element 10 extends along the fluid conducting element 20 (and more particularly along a fluid conducting element proximal section 26) and further proximally beyond a fluid conducting element proximal end 28. In the section extending proximally beyond the fluid conducting element proximal end 28, the sealing element 10 is configured to receive the needle 10.

Thus, a proximal section 14 of the sealing element 10 serves as a needle seat. Further still, as depicted in the embodiments, the assembly 100 may further comprise a thrust piece 30 (which may also be referred to as a sleeve) surrounding the sealing element 10 and the fluid conducting element 20. The thrust piece 30 may be attached to the sealing element 10 and/or the fluid conducting element 20, e.g., by means of crimping.

These elements (the fluid conducting element 20, or more particularly a proximal section of the fluid conducting element 20, the sealing element 10 and the thrust piece 30) may be received in a housing 40, which is also part of the assembly 100. More particularly, the assembly 100 may comprise a securing member 60, which may be secured to the housing 40 by means of a securing mechanism, e.g., a thread. The securing member 60 may receive a distal end section 38 of the thrust piece 30 and may transmit a securing force to the thrust piece 30. This securing force may be axially transmitted to the sealing element 10, which may thus be pressed against an inner wall of the housing 40. Thus, the sealing element 10 may be compressed, which may contribute to sealing it against a needle 202 that is inserted.

That is, the needle seat is provided by the sealing element 10, which, at the same time, provides the sealing against the fluid conducting element 20. Thus, a needle seat is provided which is realized in a simple manner. Embodiments of the present invention may thus have the following advantages: There may be provided an improved sealing of the needle seat, e.g., due to fewer air gaps where the material can flow to. Further, wear of the materials may be reduced. Further still, only a limited number of elements are used, rendering the assembly stage easier, which may lead to fewer mistakes when assembling the assembly. Further still, dead volumes may be reduced (in some embodiments even to 0) and the assembly may be adapted to withstand high pressures.

It will be understood that the assembly 100 may be part of a sampler, which also comprises the needle 202 and of a liquid chromatography system.

Further details of exemplary embodiments of a needle receiving assembly 100 are now described with reference to the individual FIGS. 9 to 14.

FIG. 9 depicts a longitudinal section of an assembly 100 according to embodiments of the present invention. The assembly 100 may be for receiving a liquid sample from a sample pick-up means, for instance a needle 202, as depicted in FIG. 9. In simple terms, the assembly 100 may comprise a fluid conducting element 20 and a sealing element 10.

The fluid conducting element 20 may comprise a fluid conducting element proximal section 26, which may also be referred to as proximal section 26, or simple as section 26. The fluid conducting element 20 may also comprise a fluid conducting element proximal end 28, which may also be referred to as proximal end 28, or simply as end 28.

As depicted in FIG. 9, the fluid conducting element 20 may further comprise an inner tube 22, which may be referred to as concentric inner tube 22. The fluid conducting element 20 may comprise a plurality of materials, inter alia, polymeric materials such as high-performance plastic materials, alloys such as steel alloys and nickel alloys, and/or fused silica materials. In one embodiment, the inner tube 22 may comprise a fused silica material.

Moreover, in one embodiment, the inner tube 22 may be coated by one or more covering layers, which may be referred to as coating layer 24 or a sheathing layer 24. The sheathing layer 24 may comprise a plurality of materials such a polymeric material or composites.

In one embodiment, the sheathing layer 24 may comprise a high-performance plastic. It should be understood that the term high-performance plastic is intended to indicate a plurality of polymers exhibiting certain properties such as, for example, temperature stability, chemical resistance, mechanical properties e.g. resistance to high pressures, etc. For instance, a high-performance plastic may comprise, without being limited to, a polyaryletherketone (PAEK) such as a polyether ketone (PEK), a polyether ether ketone (PEEK), etc.

The assembly 100 may also comprise a thrust piece 30, which may also be referred to as thrust sleeve 30. As depicted in FIG. 9, the thrust piece 30 may comprise a thrust proximal portion 34 and a thrust distal portion 36, which may also be referred to as proximal portion 34 and distal portion 36, respectively. Moreover, the thrust distal portion 36 of the thrust piece 30 may comprise a thrust distal end section 38, which may radially extend beyond the distal portion 36, and thus, the thrust distal end section 38 may comprise an extended outer diameter.

The sheathing layer 24 may also comprise a sheathing layer proximal portion 242, which may extend axially along the distal portion 36 of the thrust piece 30. The sheathing layer proximal portion 242 of the sheathing layer 24 may also comprise a sheathing layer proximal end section 244. The sheathing layer proximal portion 242 may also be referred to as proximal portion 242, and the sheathing layer proximal end section 242 may also be referred to as proximal end section 242.

The sealing element 10 may also comprise a proximal portion 14 and a distal portion 12.

In one embodiment, as depicted in FIG. 9, the thrust piece 30 may surround the distal portion 12 of the sealing element 10, the proximal section 26 of the fluid conducting element 20 (including the proximal section 242 of the sheathing layer 24, if provided).

In one embodiment, the proximal portion 14 and the distal portion 12 may comprise different outer diameters, wherein the outer diameter of the proximal portion 14 may be greater than the outer diameter of the distal portion 12. Moreover, the distal portion 12 of the sealing element 10 may extend along the fluid conducting element proximal section 26 and may further receive the fluid conducting element proximal section 26.

In some embodiments, the inner diameter of the distal portion 12 may be constant, i.e. the inner diameter of the distal portion 12 may remain invariable along the axial direction. Additionally or alternative, the outer diameter of the distal portion 12 of the sealing element 10 may be constant along the axial direction.

The proximal section 26 of the fluid conducting element 20 may be surrounded by the sealing element 10 surpassing the proximal end 28 of the fluid conducting element 20 in the proximal direction. Put differently, the sealing element 10 may extend along the fluid conducting element proximal section 26 and proximally beyond the fluid conducting element proximal end 28.

In more simple words, the sealing element 10 may comprise an inner diameter of a given size corresponding to the dimensions of an outer diameter of the fluid conducting element 20, which may allow the distal portion 12 of the sealing element 10 to accommodate the proximal section 26 of the fluid conducting element 20, and which further abuts the proximal end 244 of the proximal section 242 of the sheathing layer 24.

That is, in the embodiment depicted in FIG. 9, the fluid conducting element 20 comprises an inner tube 22 (e.g., formed of fused silica) and a sheathing layer 24 (e.g., formed of a plastic material). As is depicted, the inner tube 22 of the fluid conducting element 20 extends further to the proximal direction than the sheathing layer 24. Thus, the proximal section of the fluid conducting element 20 does not comprise the sheathing layer 24. In this section, i.e., surrounding the proximal section of the fluid conducting element 20, the sealing element 10 is provided. As can be seen, an outer diameter of the distal section 12 of the sealing element 10 may correspond to the outer diameter of the sheathing layer 24 of the fluid conducting element.

Generally, the sealing element 10 may be attached to the fluid conducting element 20. This can be done, e.g., by means of the thrust piece 30. For example, the thrust piece 30 may be crimped (i.e., plastically deformed) onto the sealing element 10, such that the thrust piece 30, the sealing element 10 and the fluid conducting element 20 are connected to one another. Thus, the sealing element 10 can already be firmly attached to the fluid conducting element 20 even when the needle receiving assembly is unassembled (i.e. even when not secured by the securing member 60). Moreover, providing the sealing element 10 attached to the fluid conducting element 20 can be advantageous as the needle seat 10 with the fluid conducting element 20 can be completely exchangeable, which can allow for easy service and maintenance. In other words, the sealing element and the fluid conducting element 20 can be handled as being one piece.

The sealing element 10 may comprise an inner surface, which may be referred to as inner walls of the sealing element 10 and conceptually identified by reference numeral 204. Furthermore, the sealing element 10 may comprise at the inner walls 204 of the proximal portion 14 one or more adjoining slopes forming acute angles.

The slope section 16 may also be referred to as first section 16, and the slope section 18 may also be referred to as second section 18. The first section 16 is more proximal than the second slope section 16. The acute angle formed by the first section 16 and the second section 18 may also be referred to as taper angle. In other words, the sealing element 10 may comprise an inner diameter, wherein the proximal section 14 may comprise a section with a constant diameter along the axial direction. The proximal section 14 may further comprise a first section 16 with an inner diameter tapering along the axial direction. Furthermore, the proximal section 14 may comprise a second section 18 more distal than the first section 16, and with an inner diameter tapering along the axial direction, forming a taper angle different than the taper angle of the first section 16.

The first section 16 may also be referred to as acute slope section 16, end slope section 16 or simply as slope section 16. The second section 18 may also be referred to as acute slope section 18 or simply as slope section 18.

Furthermore, the sealing element 10 may comprise an outer diameter at the proximal portion 14 different from an outer diameter at the distal portion 12.

In one embodiment, the outer diameter of the proximal portion 14 of the sealing element 10 may be greater than the outer diameter of the distal portion 12 of the sealing element 10. For instance, a quotient of the outer diameter of the proximal portion 14 of the sealing element 10 and the outer diameter of the distal portion 12 of the sealing element 10 may be greater than 1.8, however smaller than 3. This can facilitate securing and/or pressing the sealing element 10 against an inner wall of the housing 40. More particularly, the thrust piece 30 can extend along the distal portion 12 of the sealing element 10, up to the proximal portion 14 of the sealing element 10. As the proximal portion 14 of the sealing element 10 can comprise a greater outer diameter, the thrust piece 30 may exert an axial force in the upstream direction to the sealing element 10, thus, compressing the sealing element 10.

The taper angle of the first section 16 may be greater than the taper angle of the second section 18, which may be advantageous, as it may facilitate access of needle 202 of different diameters to the assembly 100, and furthermore, the taper angle of the second slope section 18 may contribute to the sealing of the needle 202. The taper angle of the first section 16 may be in the range 35° to 60°, preferably 40° to 55°, such as 45° to 50°. The taper angle of the second section 18 may be in the in the of 10° to 35°, preferably 15° to 30°, such as 20° to 25°.

The sealing element 10 may comprise a material with a plurality of properties, such as high-temperature stability, high mechanical strength and relatively low compressive strength. For instance, the sealing element 10 may comprise a polyaryletherketone (PAEK) such as a polyether ketone (PEK), a polyether ether ketone (PEEK), etc.

The sealing element 10 may be malleable, which may allow mechanical deformation to take place. In some instances, this may be advantageous, as it may allow formation of a contour, which may be suitable for sealing a sample delivery means, e.g. the needle 202. In more simple words, the needle 202 may apply an axial force on the sealing element 10, which may be sufficient to mechanically deform the inner walls 204 the sealing element 10, i.e. the needle 202 may form an "ideal" sealing contour in the material of the sealing element 10.

As discussed, the sealing element 10 may be attached to the proximal end section 28 of the fluid conducting element 20. The fluid conducting element 20 may be fastened to the sealing element via a fastening mechanism, which may also be referred to as fixing mechanism or mounting mechanism. The fastening mechanism may comprise a mechanical fixing method, a chemical fixing method or any combination thereof. For instance, the fluid conducting element 20 may be fastened using a mechanical fastening method such as a crimp method. In some instances, the crimp method may be advantageous, as it may allow compacting the sealing element 10 by means of the thrust element 30 and thus, improving the sealing effect.

In another embodiment, the fastening method may comprise other fixing means such as the application of a non-metallic substance on the inner surface of the thrust piece 30, the outer distal portion 12 of the sealing element 10 or on both mentioned surfaces which, when put in contact, may bind the surfaces together. Such fixing mechanism may, for example, be referred to as gluing, however it will be understood that the term is intended to comprise the use of any type of adhesive.

In one embodiment, the sealing element 10 may also be directly pressed in the thrust piece 30. For instance, the thrust piece 30 (which may also be referred to as a sleeve, such as a crimp sleeve) may be used in combination with an adhesive. In more simple words, the thrust piece (i.e., the crimp sleeve) may directly be pressed into the sealing element 10, and an adhesive that may strengthen the binding of the sealing element 10 with the thrust piece 30.

The assembly 100 may also comprise a securing member 60, which may also be referred member 60 and a housing 40. The housing 40 may accommodate a section of the fluid conducting element 20, the sealing element 10 and the thrust piece 30. More particularly, these elements may be held in the housing by means of the securing member 60. The securing member 60 may be attached to the housing 40 by means of an attachment mechanism. For example (see FIG. 11), the attachment mechanism may be realized as a thread 66. Thus, the securing member 60 is secured in the housing 40. It will be understood that by securing the securing member 60 in the housing 40, the securing member 60 can transmit an axial force to the thrust piece 30 and thus also to the sealing element 10 to thus seal the sealing element 10 against inner walls of the housing 40.

That is, the securing member 60 may be adapted to secure the discussed elements in the housing 40, for example, via a screwing mechanism. In more simple words, the securing member 60 may be for fixing these elements in the housing 40.

In one embodiment, the securing member 60 may fix the discussed elements to the housing 40 via a sliding mechanism.

In another embodiment, the securing member 60 may fix the discussed elements to the housing 40 via a direct press-in mechanism.

In a further embodiment, the securing member 60 may fix the discussed elements to the housing 40 via caulking.

That is, in one embodiment, the fluid conducting element 20 (together with the sealing element 10 and the thrust piece 30) may, for example, be screwed into the housing 40.

In another embodiment, the fluid conducting element 20 (together with the other discussed elements) may directly be pressed into the housing 40.

In a further embodiment, fixing the fluid conducting element 20 (together with the other discussed elements) in the housing 40 may also comprise applying a caulking material.

In order to prevent any undesired detachment within the assembly 100 or removal of elements from the assembly 100, fixing mechanisms may be applied such as securing by, inter alia, caulking, crimping, punching, etc., or any combination thereof that may secure the assembly 100. In some instance, this may be advantageous, as it may allow to eliminate any gaps previously present due to tolerances.

The sealing element 10 may receive the needle 202 at the proximal portion 14. When the needle 202 starts entering the assembly 100, it may exert an axial force along the axial direction. Such an exerted force may pre-tension the sealing element 10, which in some instances may be advantageous, as it may allow the sealing element 10 to withstand high pressures, such as, for example, pressure higher than 1000 bars, such as 1500 bars. That is, by the needle 202 being pressed into the sealing element 10 (which may be formed of a soft material), the sealing element 10 may be pre-tensioned, and thus, a pressure tight connection between the needle 202 and the sealing element 10 may be formed. Thus, the assembly 100 may be operated at high pressures.

Put differently, the needle 202 may apply an axial force on the sealing element 10. For example, the axial force may be in the range to 10 N to 100 N, such as 20 N to 50 N. The tip of the needle 202 may have a diameter in the range of 0.1 mm to 0.6 mm, such as 0.3 mm. As an example, an axial force of 20 N and a needle 202 having a tip with a diameter of 0.25 mm is considered. The tip has an area of $\pi \cdot (0.125 \text{ mm})^2 = 4.9 \cdot 10^{-8} \text{ m}^2$. Thus, the pressure exerted corresponds to $$4.1 \cdot 10^8 \frac{N}{m^2} = 4.1 \cdot 10^8 \text{Pa} = 410 \; MPa = 4,100 \text{ bar.}$$

This may be higher than the compressive strength of the material of the sealing element 10, e.g. the material of the sealing element 10 may exhibit a compressive strength of approximately 100 MPa. Thus, the needle 202 may deform the sealing element, which may further contribute to the sealing. Further, it will also be understood that the pressure exerted from the needle 202 on the sealing element 10 may be higher than the pressures of the liquid flowing through the assembly (which typically may be around 1,000 bar). Thus, embodiments of the present technology may be used in such pressure ranges.

The outer surface of the tip 208 of the needle 202 may also form an angle, which is more acute than the angles of the tapered sections of the sealing element 10.

Figure 10:
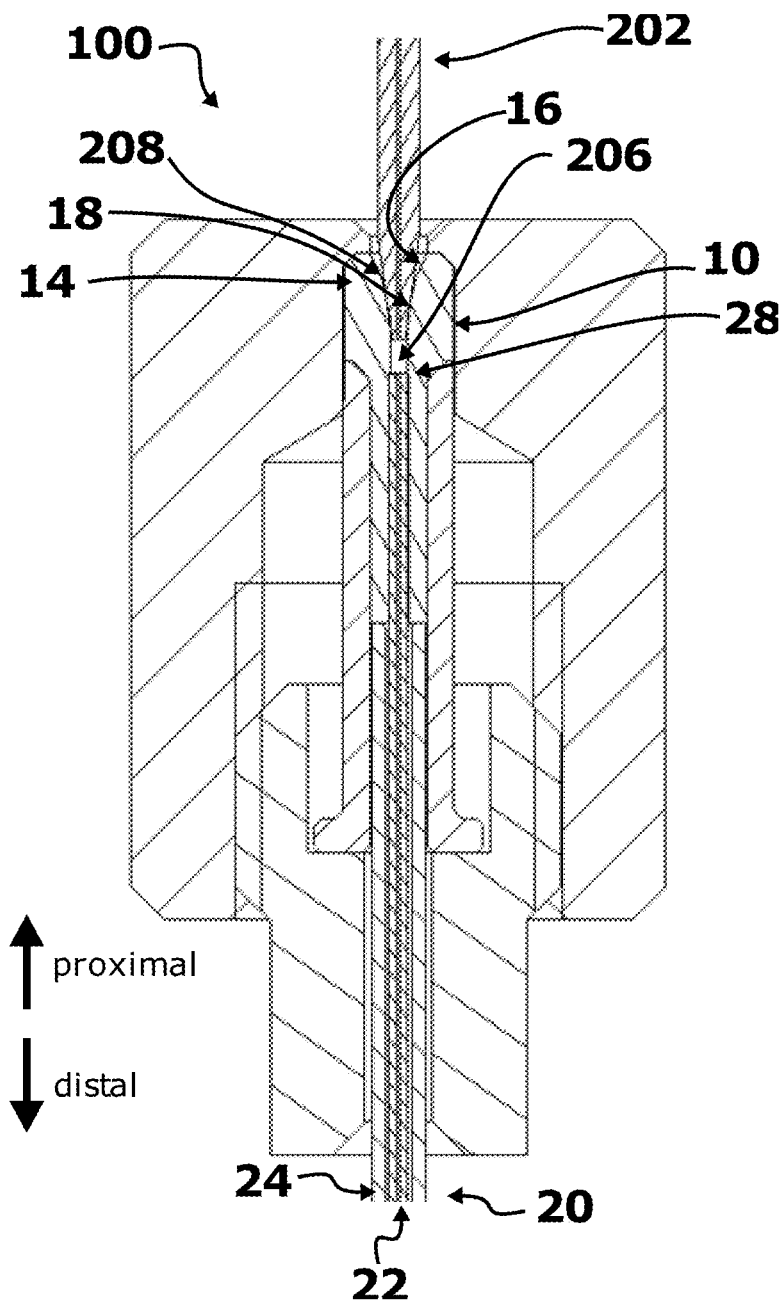
FIG. 10 depicts a longitudinal section of an assembly for receiving a fluid from a needle with a needle accommodated in the assembly according to embodiments of the present invention.

FIG. 10 depicts a longitudinal section of the assembly 100 for receiving a fluid from the needle 202 with the needle 202 accommodated in the assembly 100 according to embodiments of the present invention.

The needle 202 may access the assembly 100 and be received by the sealing element 10. On the process of entering the assembly 100, the needle 202 may mechanically deform the inner walls 204 by application of an axial force, which may be advantageous, as it may allow to form a contour in the sealing element 10. This contour may be favorable, as the needle 202 may more perfectly fit in the sealing element 10, which as a result would be "completely" sealed.

In other words, the needle 202 may, for instance, be pressed in the cavity of the sealing element 10, which may also allow the needle 202 to be pressed against the inner walls 204 of the sealing element 10 at the proximal portion 14, e.g. the needle 202 may be pressed against the second slope section 18 of the proximal portion 14. Then, the needle 202 may mechanically deform the inner walls 204 forcing the sealing element 10 to adapt to the dimension and angle of the needle tip 208.

Furthermore, the needle 202 accommodated between the inner walls 204 of the sealing element 10 may, in conjunction with the inner walls 204 and the end section 28 of the fluid conducting element 20, define a confined cavity 206, which may simply be referred to as cavity 206.

Moreover, in embodiments, the sealing element 10 may be a monolithic element, which may, for example, be achieved via injection molding. Therefore, embodiments of the present invention may minimize occurrence of cavities that may allocate volumes of liquid that may not access the analytical device, i.e. it may allow to reduce the dead volume. Thus, the volume of liquid that does not enter to analytical device may drastically be reduced in comparison to the prior art.

Reducing the dead volume in the assembly 100 may be advantageous, as it may allow to improve chromatography separations of analytes as well as contributing to improve separation and quantification of peaks in high-performance liquid chromatography.

As discussed, it will be understood that the needle 202 may be pressed into the sealing element 10, which thus serves as a needle seat. When pressing the needle 202 into the sealing element 10, which may be secured in the assembly 100 by means of the thrust piece 30 and the securing member 60, the sealing element 10 may deform to further improve the sealing effect between the sealing element 10 and the needle 202. By means of this deformation, also a sealing effect between the sealing element 10 and the housing 40 (e.g., between the sealing element 10 and a cavity proximal section 484 (see FIG. 11) of the housing 40) may be improved, as the deformation of the sealing element 10 may also press the sealing element 10 more strongly against the housing 40.

Figure 11:
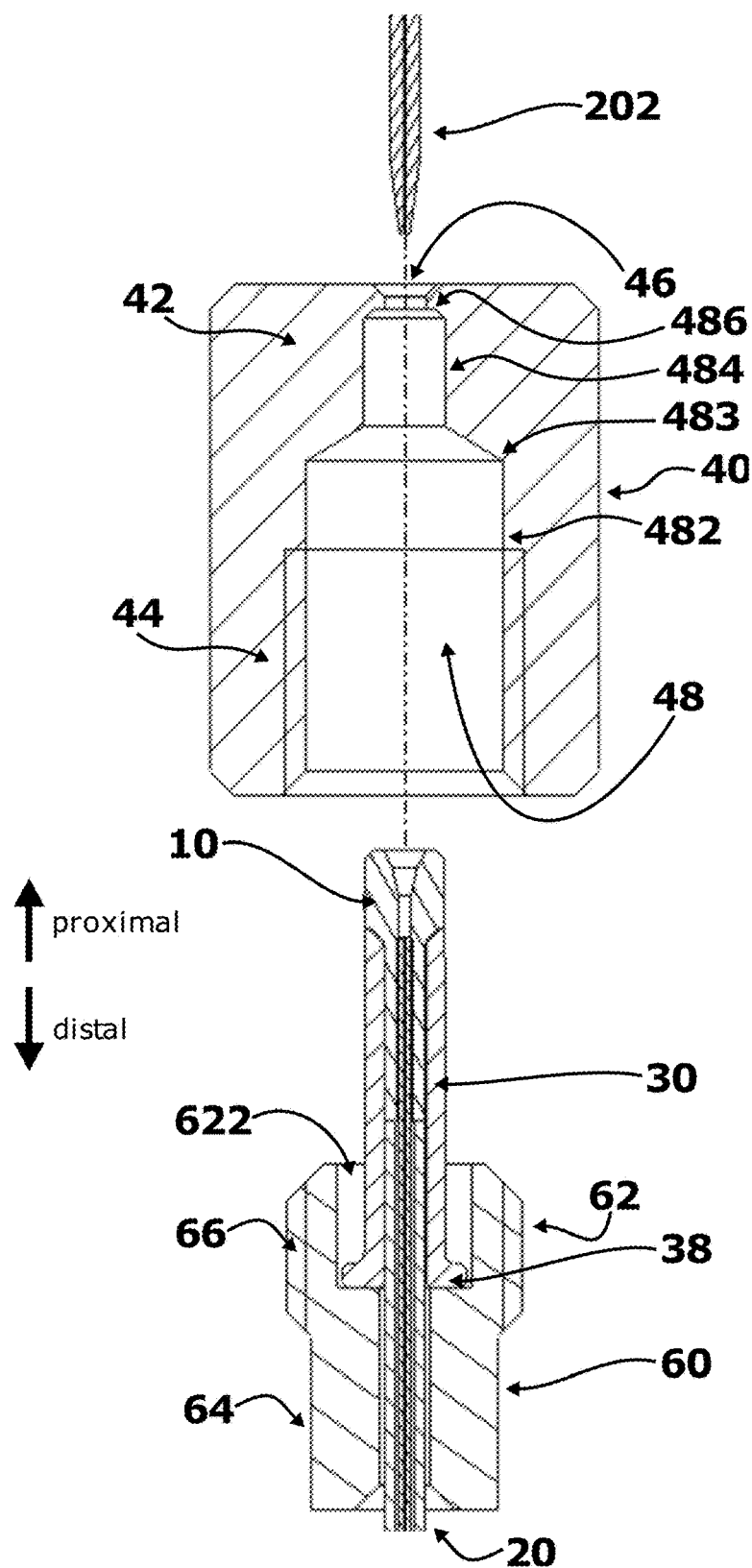
FIG. 11 depicts an exploded longitudinal section of an assembly for receiving a fluid from a needle according to embodiments of the present invention.

FIG. 11 depicts an exploded longitudinal section of the assembly 100 for receiving a fluid from the needle 202 according to embodiments of the present invention.

The assembly 100 may comprise a bushing housing 40, which may be referred simply as housing 40. It will be understood that in the assembled state, the securing member 60 is secured in the housing 40.

Furthermore, the housing 40 may comprise a housing proximal portion 42 and a housing distal portion 44. In one embodiment, the housing 40 may also comprise an opening 46 arranged concentric to the sealing element 10 and the fluid conducting element 20, which may allow the needle 202 accessing to the assembly 100.

The housing 40 may also comprise a hollow body which may form a receptacle for components of the assembly 100, i.e. a cavity to confine a plurality of components of the assembly 100, which may also be referred to as housing cavity 48, housing receptacle 48 or simply as receptacle 48. In simple words, the housing 40 may comprise a housing cavity 48 adapted to contain a plurality of components of the assembly 100 and may further comprise an opening 46 concentrically arranged with the sealing element 10 and the fluid conducting element 20 at the end of the housing proximal portion 42. It will be understood that the opening 46 and the cavity 48 together extend axially through the housing 40.

In one embodiment, the housing 40 may extend on the axial direction proximally beyond the sealing element 10 and distally beyond the thrust piece 30.

In a further embodiment, the housing 40 may also comprise a helical structure engraved on the inner walls of the hosing 40, which may allow applying a screwing-in mechanism to fix the housing 40 to the securing member 60. The helical inner structure may also be referred to as screw thread, and may, for example, extend distally along the axial direction from the center of the housing 40 to the end of the distal section 44 of the housing 40.

In another embodiment, the housing 40 may be devoid of the screw thread, in which case it may be fixed to the securing member 60 via a thrust mechanism, e.g. the cavity of the housing 40 may exhibit a diameter smaller than the securing member 60, which allow to fix the housing 40 via pressing into the securing member 60.

In a further embodiment, the housing 40 may be fixed to the securing member 60 via a sliding mechanism.

The housing 40 may exhibit a plurality of geometries such as, for example, rectangular round, quadrangular, triangular, etc. The housing cavity 48 may comprise a plurality of geometries of diverse dimensions in order to perfectly accommodate the other components of the assembly 100, such as, for example, the sealing element 10, the thrust piece 30, the fluid conducting element 20 and securing member 60.

As described, the housing 40 may comprise a housing cavity 48 for housing further elements of the assembly 100. The housing cavity 48 may comprise a cavity distal section 482 with a distal cavity inner diameter and a cavity proximal section 484 with a proximal cavity inner diameter, wherein the proximal cavity inner diameter is smaller than the distal cavity inner diameter. Further, the proximal cavity inner diameter may also be smaller than an outer diameter of the securing member 60. Thus, the securing member 60 may not be able to extend into the cavity proximal section 484. However, the thrust piece 30 may be configured to extend into the cavity proximal section 484. Furthermore, the housing cavity 48 may comprise an intermediate section 483, which may taper from the cavity distal section 482 to the cavity proximal section 484. As depicted, the cavity proximal section 484 may be connected to the opening 46 through which the needle 202 may be introduced. Furthermore, the housing cavity 48 may also comprise a proximal abutment surface 486. As depicted, e.g., in FIGS. 9 and 10, a proximal end of the sealing element 10 may abut against this proximal abutment surface 486.

It will be understood that when the sealing element 10 is inserted into the housing cavity 48 (and when it is supplied by a pressing force), the sealing element 10 may abut against the proximal abutment surface 486. Further, in some embodiments, the sealing element 10 may also abut against an inner wall of the cavity proximal section 484. Thus, the sealing element 10 may be enclosed in a space defined by the cavity proximal section 486.

It will be understood that there may be hardly any (or in fact) no gaps between the sealing element 10 and the cavity proximal section 484. Thus, a good sealing effect is achieved. As the sealing element 10 may be compressed, wear may be reduced. Generally, by means of this embodiment, a high-pressure tight needle seat with a low dead volume may be generated.

The securing member 60 may comprise a securing member proximal portion 62 and a securing member distal portion 64. The securing member proximal portion 62 may also be referred to as securing member proximal section 62. The securing member distal portion 64 may also be refer to as securing member distal section 64.

The securing member proximal portion 62 may further comprise an outer diameter different from an outer diameter of the securing member distal portion 64. In one embodiment, the outer diameter of the securing member proximal portion 62 may be greater than the outer diameter of the securing member distal portion 64.

Furthermore, the securing member 60 may comprise a protruding section 66 arrange at the securing member proximal section 62. The protruding section 66 may also be referred to as protruding portion 66. In simple words, the protruding section 66 may allow to fix the housing 40 to the securing member 60. For example, the protruding section 66 may be a thread.

In one embodiment, the housing 40 may be fixed to the securing member via pressing the housing 40 into the securing member 60.

In another embodiment, the securing member 60 may comprise an embossed helical structure as the protruding section 66, which may allow screwing the housing 40 on the securing member 60.

The securing member 60 may also comprise a securing member cavity, which may be arranged in the securing member proximal section 62 and which may exhibit a diameter that is larger (or matches) the outer diameter of the thrust distal end 38 to fix the thrust piece 30 to the securing member 60.

Figure 12:
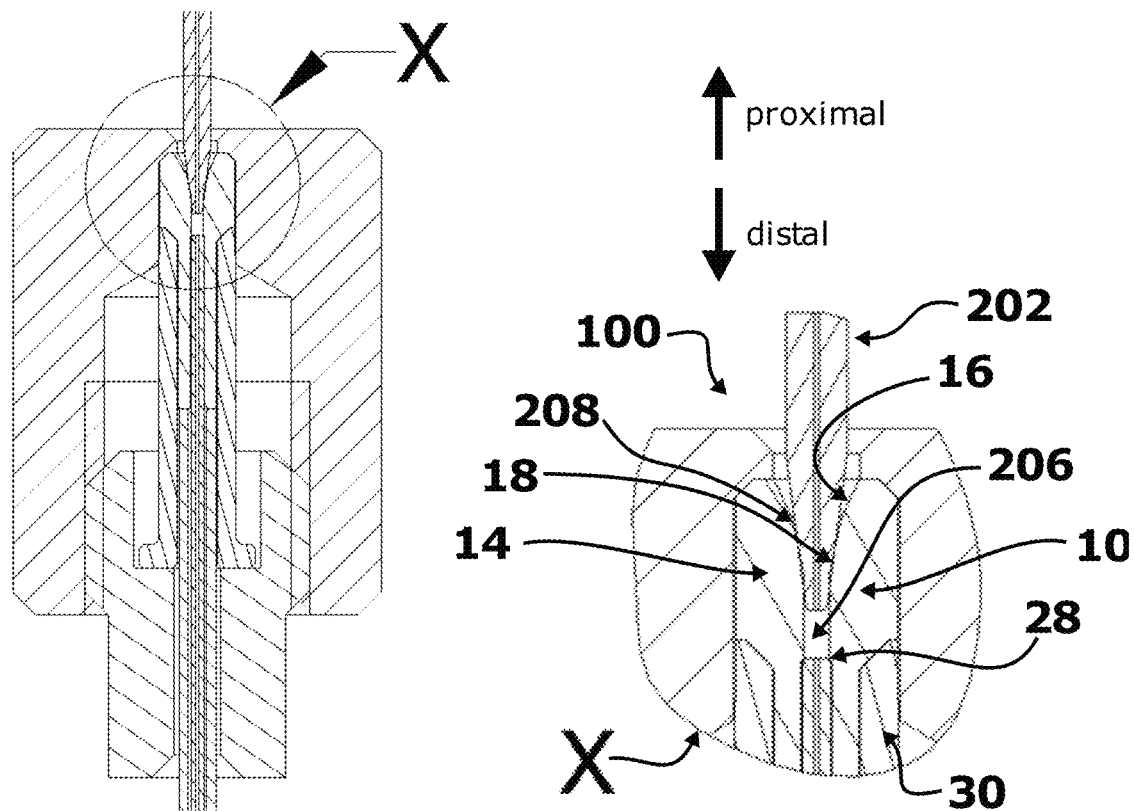
FIG. 12 depicts a detailed section excerpt of a longitudinal section of an assembly for receiving a fluid from a needle according to embodiments of the present invention.

FIG. 12 depicts a detailed section excerpt of an embodiment of the assembly 100 for receiving a fluid from the needle 202 according to embodiments of the present invention.

In simple terms, FIG. 12 depicts a zoomed-in view of the assembly 100, which is identified by reference "X". For the sake of clarity, only the zoomed-in view X carries the reference numerals mentioned below.

As described above, the needle 202 may be introduced in the assembly 100, where the second section 18 of the proximal portion 14 of the sealing element 10 may be deformed by the needle 202 to perfectly fit the needle tip 208 and as a result, the needle 202 may be sealed by the sealing element 10.

Put differently, a fluid conducting element seal may be formed on the inner walls 204 of the proximal portion 14 of sealing element 10, which means that the sealing element 10 of the present invention may fulfill two different functions.

On the one hand, the sealing element 10 may function as a seal towards the fluid conducting element 20, and on the other hand, the sealing element 10 may adopt a shape suitable to receive the needle 202, i.e. it may function as a needle seat. In still other words, the sealing element 10 may seal both against the needle 202 and the fluid conducting element 20. That is, different to the prior art, embodiments of the present invention merely utilize one element 10 realizing the sealing function both for the fluid conducting element 20 and for the needle 202.

Furthermore, as depicted in the zoomed-in view X, the sealing element 10 may also allow the needle 202 to closer approach the proximal end 28 of the fluid conducting element 20, and thus a volume 206 formed between the tip 208 of the needle 202 and the fluid conducting element 20 may be relatively small.

Moreover, the first section 16 of the proximal portion 14 of the sealing element 14 may be angled (as discussed before), which may render the space between the inner walls 204 at the section 16 larger than the inner diameter of the sealing element 10. This may be advantageous, as it may allow the entry of needle 202 of larger diameters, making the sealing element 10, and as a result the assembly 100, suitable for analytical procedures or analytical devices where the use of a needle 202 of larger diameter may be required.

With general reference to, e.g., FIG. 9, it will be appreciated that at the exit of the needle seat 10, the needle seat 10 is limited by the housing 40, the thrust piece 30 (also referred to as crimp sleeve) and the fluid conducting element 20. The needle seat 10 may be plastically deformed during assembly so that the cavities fill (free of dead volume) and the needle seat 10 (which may be formed of PEEK) may be under a high internal pressure.

Figure 13:
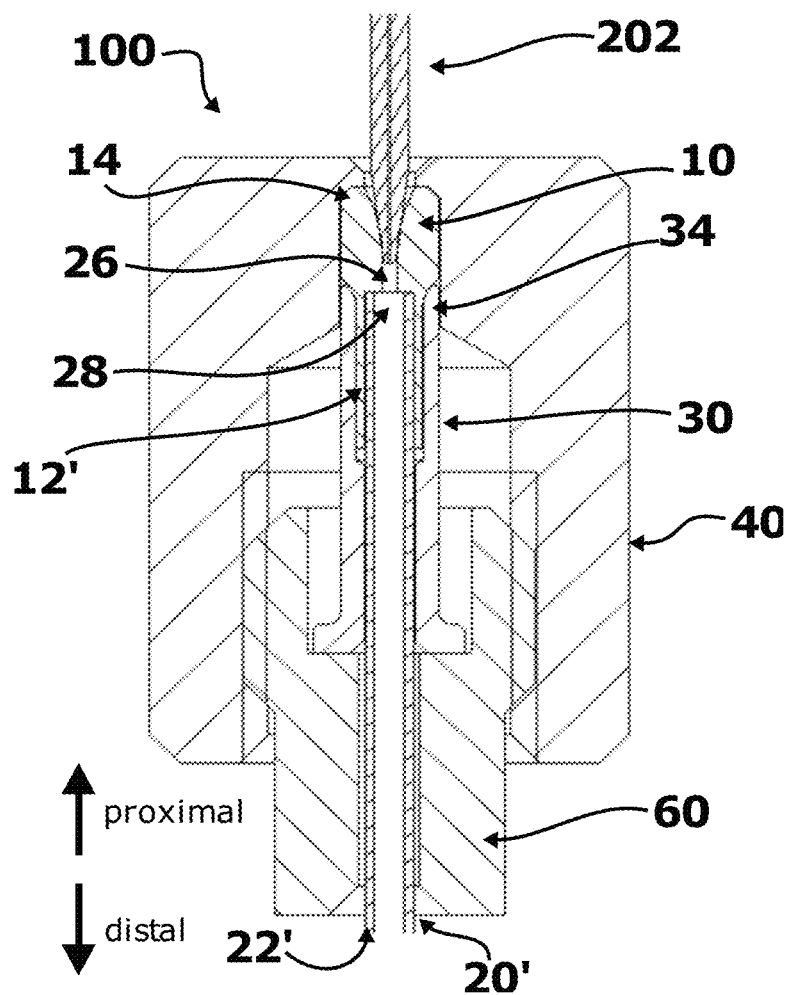
FIG. 13 depicts a longitudinal section of an assembly for receiving a fluid from a needle comprising a metal or polymer fluid conducting element according to embodiments of the present invention.
Figure 14:
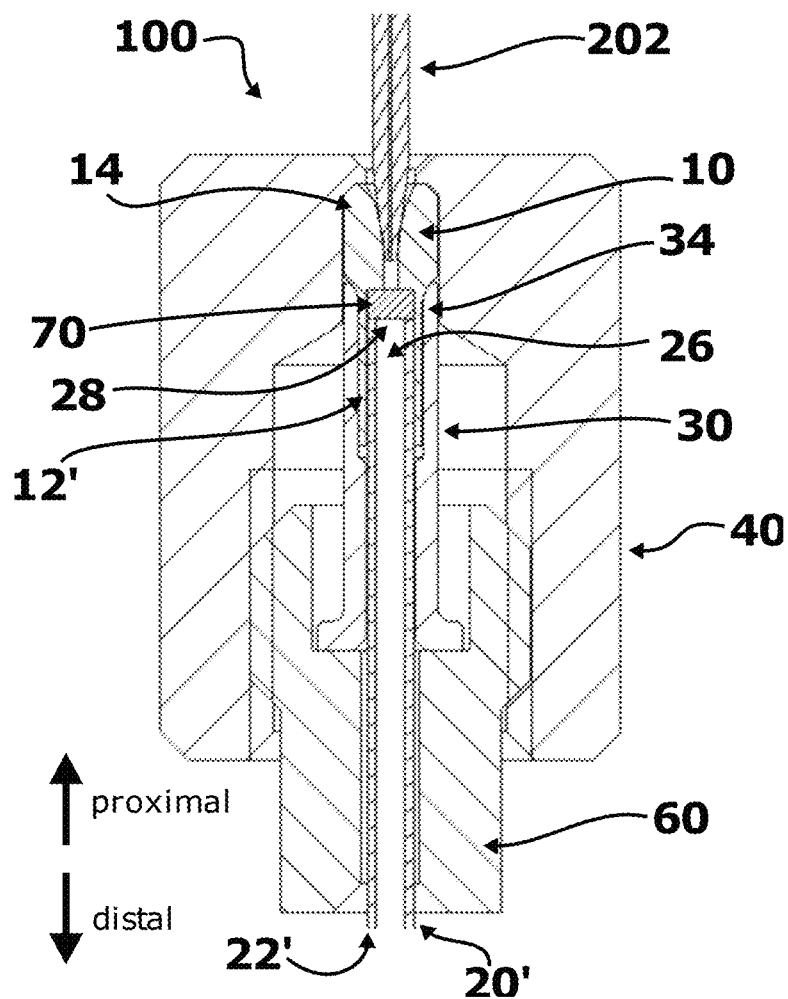
FIG. 14 depicts a longitudinal section of an assembly for receiving a fluid from a needle comprising a metal or polymer fluid conducting element and a filtering element according to embodiments of the present invention.
Figure 15:
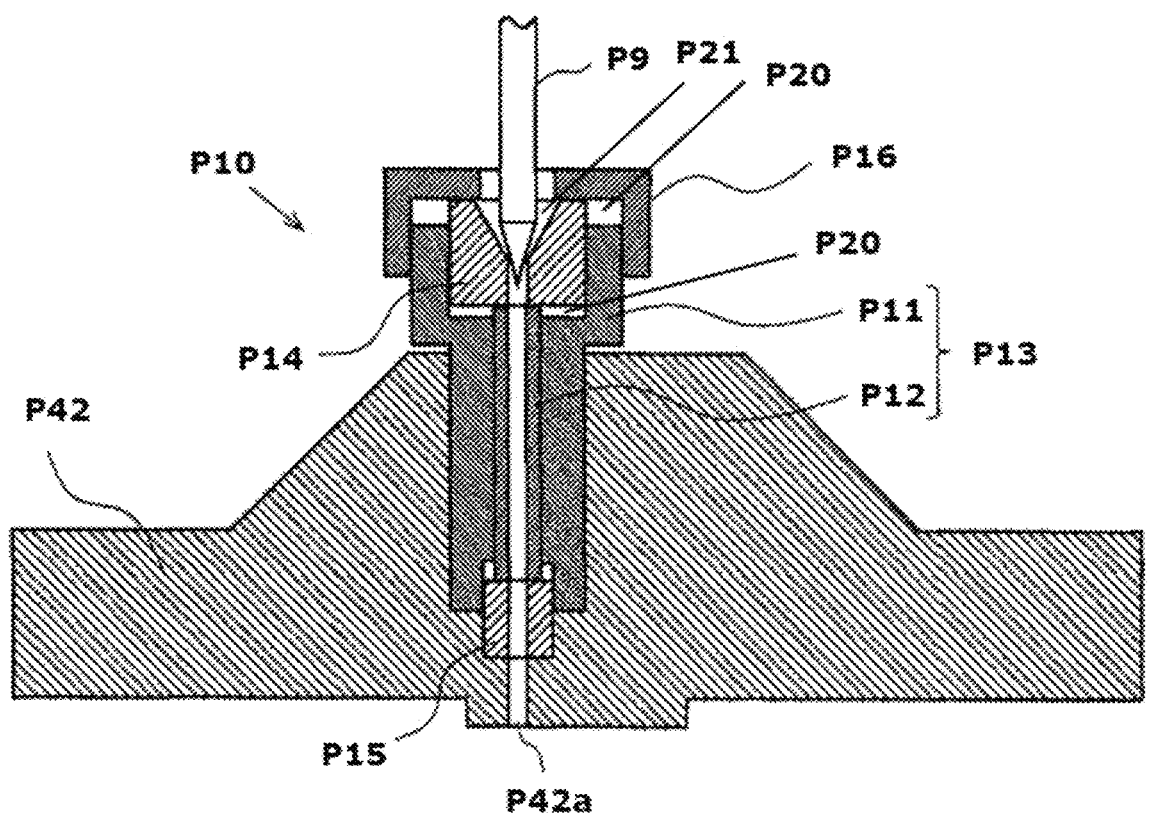
FIGS. 15 and 16 depicts prior art assemblies.
Figure 16:
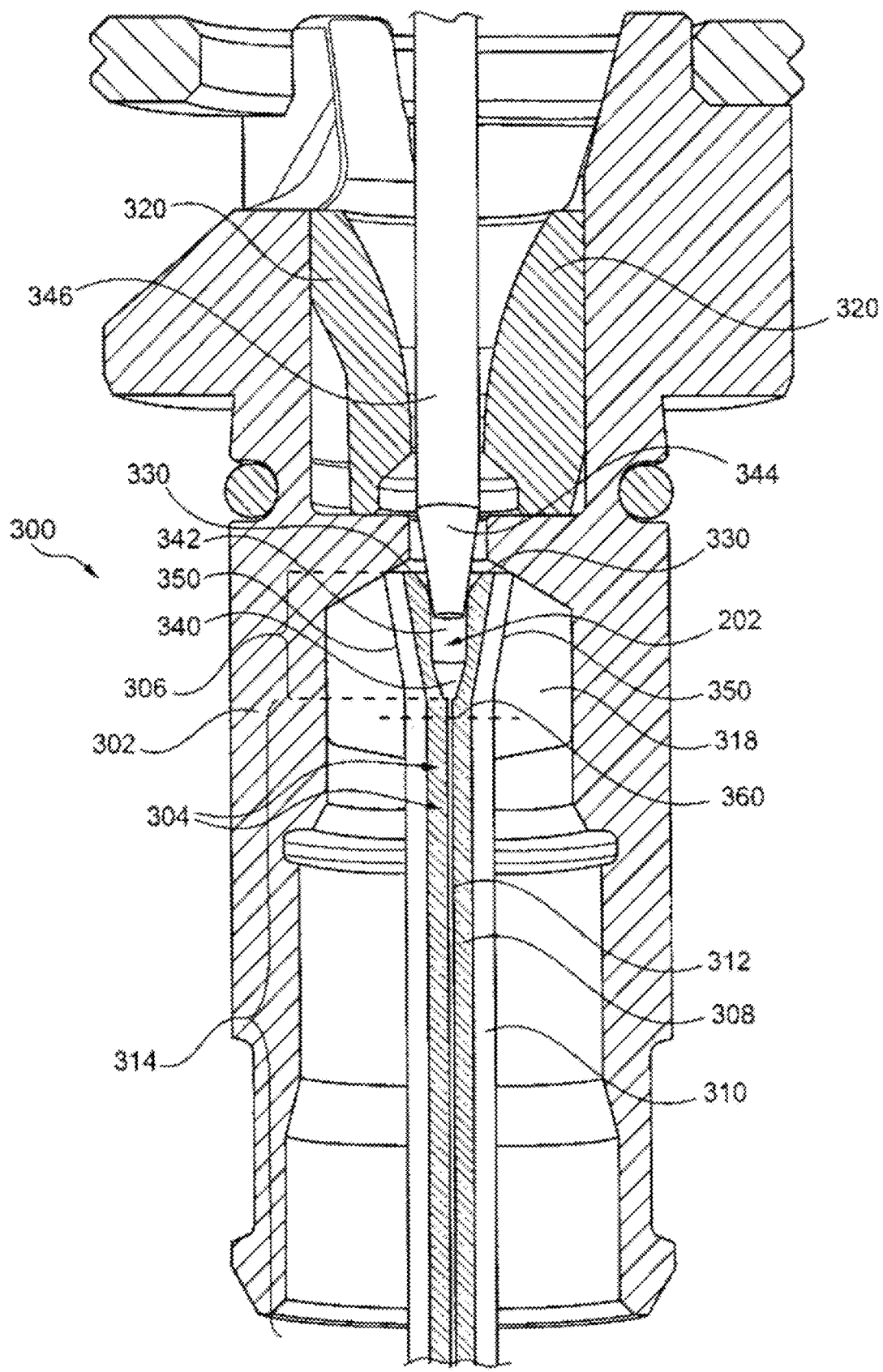

FIG. 13 and FIG. 14 depict further embodiments of the present invention comprising a metal or plastic fluid conducting element 20'. For the sake of simplicity, however, only the differentiating features are detailed below, while features that are identical to the features described above are not further explained.

FIG. 13 depicts a longitudinal section of the assembly 100 for receiving a fluid from the needle 202 comprising a metal or plastic fluid conducting element 20' according to embodiments of the present invention.

In one embodiment, the fluid conducting element 20' may comprise a metal structure comprising alloys that may exhibit resistance to high pressures, such as, for example, steel alloys, nickel alloys, etc. However, alternatively, the fluid conducting element 20' can also be formed of a plastic material, i.e., of a synthetic material.

In simple terms, the fluid conducting element 20' comprises the tubing 22', which may be formed of a plastics material or of a metal. In some embodiments the fluid conducing element 20' may be a capillary 20'. In such embodiments, the tubing 22' is "empty", thus, allowing a fluid to flow therein uninterrupted. In such embodiments, the tubing 22' may comprise an inner diameter in the range of 350 µm to 500 µm, such as 400 µm to 450 µm. The fluid conducting element 20' realized as a capillary 20' may comprise an outer diameter, which may be in the range of 0.5 mm to 1.2 mm, preferably 0.75 mm to 0.85 mm, such as 0.79 mm. Alternatively, the fluid conducting element 20' can be a chromatographic column 20. In such embodiments, the tubing 22' can be packed with the stationary phase, thus, forming a chromatographic column 20' for realizing the separation of the sample. In such embodiments, the tubing 22' may comprise an inner diameter in the range of 350 µm to 10 mm, such as 400 µm to 1 mm. Alternatively, in such embodiments, the tubing 22' may comprise an inner diameter in the range of 20 µm to 10 mm, such as 50 µm to 5 mm, and more particularly 50 µm to 2.1 mm.

In the depicted embodiment, the thrust piece 30 may comprise different portions having different inner diameters. Further, it will be understood that in the depicted embodiments, the thrust piece 30 may be crimpled directly onto the fluid conducting element 20, e.g., onto the metal of the fluid conducting element 20.

Moreover, the assembly 100 depicted in FIG. 13 may comprise a housing 40 and a securing member 60 as described above. The sealing element 10 may comprise a proximal portion 14 and a distal portion 12'. The distal portion 12' may be thinner than the distal portion 12 depicted in FIG. 9. It will be understood that the fluid conducting element 20' (formed of metal or plastics material) depicted in FIGS. 13 and 14 may be thicker than the fluid conducting element 20 depicted in FIGS. 9 to 12. Further, it will also be understood that the metal or plastic fluid conducting element 20' may be less prone to break than the fused silica fluid conducting element 20. This may allow for the distal portion 12' of the sealing element 10 to be thinner.

In simple terms, the assembly 100 depicted in FIG. 13 comprises a metal or plastic fluid conducting element 20 that extends along the axial direction proximally beyond the securing member 60, through the thrust piece 30 and until the distal portion 12 of the sealing element 10 nearly parallel to end of the proximal section 34.

FIG. 14 depicts a longitudinal section of an assembly 100 for receiving a fluid from the needle 202 comprising a metal- or polymer fluid conducting element 20' and a filtering element 70 according to embodiments of the present invention. The filtering element 70 may also be referred to as filter unit 70, filtering piece 70, filtering member 70 or simply as filter 70.

In simple words, the filter 70 may be conceived in such a way that a fluid, e.g. a liquid sample to be analyzed, may flow through the filter 70 and may be filtrated before entering the fluid conducting element 20'.

Put differently, the filter 70 may comprise a permeable surface with a porous structure whereby a feed, e.g. a liquid, may pass through and due to the lattice structure of the filter 70, particles contained in the liquid exceeding the porous size of the filter 70 may be retained, while the liquid and smaller particles may continue.

Furthermore, the use of the filter 70 may be advantageous, as it may allow, for instance, reducing potential contaminations of an analytical fluid and avoid blocking of the fluid conducting element 20'. A consequent advantage of using the filter 70 may comprise an extended service life of individual parts of an analytical device, e.g. the fluid conducting element 20'.

In one embodiment, for instance as depicted in FIG. 14, the filter element may be arranged at the proximal end 28 of the fluid conducting element 20'.

The filter 70 may comprise chemically inert materials such as, but not limited to, polymeric structures e.g. polyether ether ketone (PEK) and polyether ether ketone (PEEK), or sintered materials e.g. a fritted glass and a sintered metal frit.

While the filter 70 is described in conjunction with a metal or glass fluid conducting element, it should be understood that this is not critical and that the filter may be used independent of the employed fluid conducting element.

Whenever a relative term, such as "about", "substantially" or "approximately" is used in this specification, such a term should also be construed to also include the exact term. That is, e.g., "substantially straight" should be construed to also include "(exactly) straight".

It should also be understood that whenever reference is made to an element this does not exclude a plurality of said elements. For example, if something is said to comprise an element it may comprise a single element but also a plurality of elements.

Whenever steps were recited in the above or also in the appended claims, it should be noted that the order in which the steps are recited in this text may be accidental. That is, unless otherwise specified or unless clear to the skilled person, the order in which steps are recited may be accidental. That is, when the present document states, e.g., that a method comprises steps (A) and (B), this does not necessarily mean that step (A) precedes step (B), but it is also possible that step (A) is performed (at least partly) simultaneously with step (B) or that step (B) precedes step (A). Furthermore, when a step (X) is said to precede another step (Z), this does not imply that there is no step between steps (X) and (Z). That is, step (X) preceding step (Z) encompasses the situation that step (X) is performed directly before step (Z), but also the situation that (X) is performed before one or more steps (Y1), . . . , followed by step (Z). Corresponding considerations apply when terms like "after" or "before" are used.

While in the above, a preferred embodiment has been described with reference to the accompanying drawings, the skilled person will understand that this embodiment was provided for illustrative purpose only and should by no means be construed to limit the scope of the present invention, which is defined by the claims.

Furthermore, reference numbers and letters appearing between parentheses in the claims, identifying features described in the embodiments and illustrated in the accompanying drawings, are provided as an aid to the reader as an exemplification of the matter claimed. The inclusion of such reference numbers and letters is not to be interpreted as placing any limitations on the scope of the claims.

What is claimed is:

1. A needle receiving assembly configured to receive a fluid from a needle, the needle receiving assembly comprising:
   a fluid conducting element comprising: a fluid conducting element proximal section and a fluid conducting element proximal end; and
   a sealing element, wherein the sealing element is configured to receive the needle,
   wherein the fluid conducting element includes an axial direction, and a radial direction perpendicular to the axial direction,
   wherein the needle receiving assembly comprises a fluid conducting element housing,
   wherein the needle receiving assembly is configured to connect to a needle of a needle assembly, and
   wherein the fluid conducting element housing comprises an aligning component configured to contact a needle housing of the needle assembly and to increase alignment in the radial direction between the needle and the needle receiving assembly upon contact between the aligning component and the needle housing of the needle assembly;
   wherein the fluid conducting element housing comprises a lateral protruding portion, and wherein the lateral protruding portion comprises an inner lateral surface that laterally surrounds a cavity of the fluid conducting element housing;

wherein the aligning component comprises an aligning inner surface formed by at least a portion of the inner lateral surface of the lateral protruding portion;

wherein the fluid conducting element housing comprises a central protruding portion, and wherein the central protruding portion protrudes proximally beyond a base of the fluid conducting element housing; and wherein the lateral protruding portion protrudes proximally beyond the central protruding portion.

2. The needle receiving assembly according to claim 1, wherein the fluid conducting element housing comprises an outer lateral surface and wherein the aligning component comprises: an aligning outer surface formed by at least a portion of the outer lateral surface of the fluid conducting element housing.

3. The needle receiving assembly according to claim 1, wherein the central protruding portion comprises an outer lateral surface, and wherein the aligning outer surface comprises a portion of the outer lateral surface of the central protruding portion of the fluid conducting element housing.

4. The needle receiving assembly according to claim 1, wherein the fluid conducting element contains a packed stationary phase, and wherein the packed stationary phase is configured to separate a sample.

5. The needle receiving assembly according to claim 1, wherein the sealing element comprises a polymeric material, the polymeric material selected from the group consisting of a poly-ether-ether-ketone, a poly-ether-ketone, a poly-ketone, a poly-ether-ketone-ether-ether-ketone, and a polyphenylene sulfide, and a combination thereof.

6. A connection assembly configured to introduce a fluid from a needle to a fluid conducting element, the connection assembly comprising:

a) a needle assembly configured to connect the needle to a needle receiving assembly, wherein the needle assembly comprises:

the needle, wherein the needle includes an axial direction along a length of the needle, a radial direction, and a tip, wherein the radial direction is perpendicular to the axial direction;

a needle housing, wherein the needle occupies a part of a cavity of the needle housing, the needle housing comprising an aligning component configured to increase alignment in the radial direction between the needle and the needle receiving assembly upon contact between the aligning component and the needle receiving assembly; and b) the needle receiving assembly configured to receive the fluid from the needle, the needle receiving assembly comprising:

the fluid conducting element comprising: a fluid conducting element proximal section and a fluid conducting element proximal end; and a sealing element, wherein the sealing element is configured to receive the needle;

wherein the fluid conducting element housing comprises a lateral protruding portion, and wherein the lateral protruding portion comprises an inner lateral surface that laterally surrounds a cavity of the fluid conducting element housing;

wherein the aligning component comprises an aligning inner surface formed by at least a portion of the inner lateral surface of the lateral protruding portion;

wherein the fluid conducting element housing comprises a central protruding portion, and wherein the central protruding portion protrudes proximally beyond a base of the fluid conducting element housing; and wherein the lateral protruding portion protrudes proximally beyond the central protruding portion.

7. The connection assembly according to claim 6, wherein the needle housing further comprises an outer lateral surface, and wherein the aligning component comprises an aligning outer surface formed by at least a portion of the outer lateral surface of the needle housing.

8. The connection assembly according to claim 6, wherein the needle housing comprises an inner surface that laterally encloses the cavity, and wherein the aligning component comprises an aligning inner surface formed by at least a portion of the inner surface that laterally encloses the cavity.

9. The connection assembly according to claim 6, wherein the needle is unreleasably mounted on the needle housing.

10. The connection assembly according to claim 6, wherein the aligning component is configured to increase alignment in the radial direction between the needle and the needle receiving assembly by contact between the aligning component and the needle receiving assembly where there is a misalignment of up to 1 mm in the radial direction between the needle and the needle receiving assembly.

11. A sampler configured to pick up a fluid, wherein the sampler comprises a fluid conducting element and a needle, wherein the sampler comprises a needle receiving assembly and a needle assembly, a) the needle assembly configured to connect the needle to the needle receiving assembly, wherein the needle assembly comprises:

the needle, wherein the needle includes an axial direction along a length of the needle, a radial direction, and a tip, wherein the radial direction is perpendicular to the axial direction;

a needle housing, wherein the needle occupies a part of a cavity of the needle housing, the needle housing comprising an aligning component configured to increase alignment in the radial direction between the needle and the needle receiving assembly upon contact between the aligning component and the needle receiving assembly; and b) the needle receiving assembly configured to receive the fluid from the needle, the needle receiving assembly comprising:

the fluid conducting element comprising: a fluid conducting element proximal section and a fluid conducting element proximal end; and a sealing element, wherein the sealing element is configured to receive the needle;

wherein the fluid conducting element housing comprises a lateral protruding portion, and wherein the lateral protruding portion comprises an inner lateral surface that laterally surrounds a cavity of the fluid conducting element housing;

wherein the aligning component comprises an aligning inner surface formed by at least a portion of the inner lateral surface of the lateral protruding portion;

wherein the fluid conducting element housing comprises a central protruding portion, and wherein the central protruding portion protrudes proximally beyond a base of the fluid conducting element housing; and wherein the lateral protruding portion protrudes proximally beyond the central protruding portion.

12. A system for analyzing a liquid, the system comprising
a) a liquid chromatography to analyze the liquid, and
b) a sampler configured to pick up a fluid, wherein the sampler comprises a fluid conducting element and a needle, wherein the sampler comprises a needle receiving assembly and a needle assembly,
i) the needle assembly configured to connect the needle to the needle receiving assembly, wherein the needle assembly comprises:
the needle, wherein the needle includes an axial direction along a length of the needle, a radial direction, and a tip, wherein the radial direction is perpendicular to the axial direction;
a needle housing, wherein the needle occupies a part of a cavity of the needle housing, the needle housing comprising an aligning component configured to increase alignment in the radial direction between the needle and the needle receiving assembly upon contact between the aligning component and the needle receiving assembly; and
ii) the needle receiving assembly configured to receive the fluid from the needle, the needle receiving assembly comprising:
the fluid conducting element comprising: a fluid conducting element proximal section and a fluid conducting element proximal end; and
a sealing element, wherein the sealing element is configured to receive the needle;
wherein the fluid conducting element housing comprises a lateral protruding portion, and wherein the lateral protruding portion comprises an inner lateral surface that laterally surrounds a cavity of the fluid conducting element housing;
wherein the aligning component comprises an aligning inner surface formed by at least a portion of the inner lateral surface of the lateral protruding portion;
wherein the fluid conducting element housing comprises a central protruding portion, and wherein the central protruding portion protrudes proximally beyond a base of the fluid conducting element housing; and
wherein the lateral protruding portion protrudes proximally beyond the central protruding portion.

* * * * *